(12) United States Patent
Kelly et al.

(10) Patent No.: US 10,124,077 B2
(45) Date of Patent: *Nov. 13, 2018

(54) PLECTIN-1 TARGETED AGENTS FOR DETECTION AND TREATMENT OF PANCREATIC DUCTAL ADENOCARCINOMA

(71) Applicant: The General Hospital Corporation, Boston, MA (US)

(72) Inventors: Kimberly Kelly, Crozet, VA (US); Ralph Weissleder, Peabody, MA (US); Nabeel Bardeesy, Framingham, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/176,920

(22) Filed: Jun. 8, 2016

(65) Prior Publication Data

US 2017/0087257 A1    Mar. 30, 2017

Related U.S. Application Data

(63) Continuation of application No. 14/479,558, filed on Sep. 8, 2014, now Pat. No. 9,387,265, which is a continuation of application No. 12/937,777, filed as application No. PCT/US2009/040480 on Apr. 14, 2009, now Pat. No. 8,829,159.

(60) Provisional application No. 61/044,818, filed on Apr. 14, 2008.

(51) Int. Cl.
*A61K 49/14* (2006.01)
*A61K 49/00* (2006.01)
*A61K 49/18* (2006.01)
*B82Y 5/00* (2011.01)
*C07K 7/06* (2006.01)
*G01N 33/531* (2006.01)
*G01N 33/533* (2006.01)
*G01N 33/574* (2006.01)
*C07K 16/18* (2006.01)
*A61K 38/08* (2006.01)
*G01N 33/543* (2006.01)
*A61K 47/64* (2017.01)
*A61K 38/00* (2006.01)

(52) U.S. Cl.
CPC .............. *A61K 49/14* (2013.01); *A61K 38/08* (2013.01); *A61K 47/64* (2017.08); *A61K 49/0002* (2013.01); *A61K 49/0032* (2013.01); *A61K 49/0056* (2013.01); *A61K 49/1818* (2013.01); *B82Y 5/00* (2013.01); *C07K 7/06* (2013.01); *C07K 16/18* (2013.01); *G01N 33/531* (2013.01); *G01N 33/533* (2013.01); *G01N 33/54326* (2013.01); *G01N 33/54346* (2013.01); *G01N 33/57438* (2013.01); *A61K 38/00* (2013.01)

(58) Field of Classification Search
CPC ...................................................... A61K 49/14
See application file for complete search history.

(56) References Cited

U.S. PATENT DOCUMENTS

| | | |
|---|---|---|
| 5,208,020 A | 5/1993 | Chari et al. |
| 5,574,010 A | 11/1996 | McFadden |
| 5,604,203 A | 2/1997 | Balasubramaniam |
| 5,696,093 A | 12/1997 | Tseng et al. |
| 5,968,479 A | 10/1999 | Ito et al. |
| 6,046,167 A | 4/2000 | Balasubramaniam |
| 8,802,738 B2 * | 8/2014 | Emrick ............ A61K 47/48176 514/772.1 |
| 2002/0177207 A1 * | 11/2002 | Sugiyama ............... C07K 14/47 506/3 |
| 2003/0092029 A1 | 5/2003 | Josephson et al. |
| 2003/0100051 A1 * | 5/2003 | Ruben .................... C07K 14/47 435/69.1 |
| 2003/0103975 A1 * | 6/2003 | Jones .................... C07K 16/18 424/145.1 |
| 2003/0180747 A1 | 9/2003 | Hruban et al. |
| 2005/0079503 A1 | 4/2005 | Bowtell et al. |
| 2005/0095611 A1 | 5/2005 | Chan et al. |
| 2005/0249668 A1 | 11/2005 | Weissleder et al. |
| 2005/0260639 A1 | 11/2005 | Nakamura et al. |
| 2006/0024231 A1 | 2/2006 | Schnitzer et al. |

(Continued)

FOREIGN PATENT DOCUMENTS

| | | |
|---|---|---|
| JP | 2005532815 | 11/2005 |
| WO | 2002062838 | 8/2002 |
| WO | 2003030725 | 4/2003 |

(Continued)

OTHER PUBLICATIONS

European Office Action in Application No. 14190585.1, dated Sep. 12, 2017, 7 pages.
Aguirre et al., "Activated Kras and Ink4a/Arf deficiency cooperate to produce metastatic pancreatic ductal adenocarcinoma," Genes Dev 17: 3112-3126 (2003).
Aho et al., "Plectin Serves as an Autoantigen in Paraneoplastic Pemphigus," J Invest Dermatol 113: 422-423 (1999).
Alencar et al., "A novel mouse model for segmental orthotopic colon cancer," Int. J. Cancer 117:335-339 (2005).

(Continued)

*Primary Examiner* — Amber D Steele
(74) *Attorney, Agent, or Firm* — Fish & Richardson P.C.

(57) ABSTRACT

Described herein are compositions and methods for cancer cell biomarkers, such as pancreatic ductal adenocarcinoma (PDAC) cell biomarkers, and binding molecules for diagnosis and treatment of cancer, e.g., PDAC. Methods of identifying "accessible" proteomes are disclosed for identifying cancer biomarkers, such as plectin-1, a PDAC biomarker. Additionally, imaging compositions are provided comprising magnetofluorescent nanoparticles conjugated to peptide ligands for identifying PDACs.

10 Claims, 12 Drawing Sheets

Specification includes a Sequence Listing.

(56) References Cited

U.S. PATENT DOCUMENTS

2007/0054268 A1\* 3/2007 Sutherland ........... C12Q 1/6886
435/6.14
2007/0161034 A1 7/2007 Jiang et al.

FOREIGN PATENT DOCUMENTS

| WO | 2004056314 | 7/2004 |
|---|---|---|
| WO | 2006115633 | 11/2006 |
| WO | 2007109809 | 9/2007 |

OTHER PUBLICATIONS

Allport et al., "Neutrophils from MMP-9- or neutrophil elastase-cleficient mice show no defect in transendothelial migration under flow in vitro,"J Leukoc Biol 71:821-828 (2002).
Andra et al., "Not just scaffolding: plectin regulates actin dynamics in cultured cells," Genes Dev 12: 3442-3451 (1998).
Bardeesy et al., "Both p16(Ink4a) and the p19(Arf)-p53 pathway constrain progression of pancreatic adenocarcinoma in the mouse," Proc Natl Acad Sci U.S.A. 103:5947-5952 (2006).
Bausch et al., "Plectin-1 as a Novel Biomarker for Pancreatic Cancer," Clinical Cancer Research, 17(2):302-309 (2011).
Bloomston, et al., "Fibrinogen gamma overexpression in pancreatic cancer identified by large-scale proteomic analysis of serum samples," Cancer Res 66:2592-2599 (2006).
Boczonadi et al., Experimental Cell Research 313(16):3579-3591 (2007).
Brentnall et al., Ann. Intern. Med. 131:247-255 (1999).
Canadian Office Action in Canadian Application No. 2,758,415, dated Dec. 16, 2015, 4 pages.
Canto et al., "Screening for pancreatic neoplasia in high-risk individuals: an EUS-based approach," Clin. Gastroenterol. Hepatol. 2:606-621 (2004).
Carrière et al., "The Nestin progenitor lineage is the compartment of origin for pancreatic intraepithelial neoplasia," Proc Natl Acad Sci U S A. 104(11):4437-42 (2007).
Chari, "Detecting early pancreatic cancer: problems and prospects," Semin Oncol 34:284-294 (2007).
Cheng et al., "The influence of plectin deficiency on stability of cytokeratin18 in hepatocellular carcinoma," Journal of Molecular Histology, 39(2):209-216 (2007).
Ding et al., "Plectin regulates the signaling and trafficking of the HIV-1 co-receptor CXCR4 and plays a role in HIV-1 infection," Experimental Cell Research, 314(3):590-602 (2007).
European Search Report issued in EP14190585 dated Mar. 16, 2015 (11 pages).
Folli, et al., "Antibody-indocyanin conjugates for immunophotodetection of human squamous cell carcinoma in nude mice," Cancer Res 54:2643-2649 (1994).
Fontao et al., "The interaction of plectin with actin: Evidence for cross-linking of actin filaments by dimerization of the actin-binding domain of plectin," Journal of Cell Science, 114(11):2065-2076 (2001).
Fournier et al., "Conformational and biological studies of neuropeptide Y analogs containing structural alterations," Mol. Pharmacol. 45:93-101 (1994).
Gehlert et. al., "Multiple receptors for the pancreatic polypeptide (PP-fold) family: physiological implications," Proc Soc Exp Biol Med 218:7-22 (1998).
Goggins, "Molecular markers of early pancreatic cancer," J. Clin. Oncol. 23:4524-4531 (2005).
Gregor et al., "Plectin scaffolds recruit energy-controlling AMP-activated protein kinase (AMPK) in differentiated myofibres," J Cell Sci 119: 1864-1875 (2006).
Grundemar et al., "Ligand binding and functional effects of systematic double D-amino acid residue substituted neuropeptide Y analogs on Y1 and Y2 receptor types," Regulatory Peptides 62:131-136 (1996).

Hansel et al., "Molecular pathogenesis of pancreatic cancer," Annu Rev Genomics Hum Genet 4:237-256 (2003).
House et al., "A binding motif for Siah ubiquitin ligase," PNAS, 100(6):3101-3106 (2003).
Iacobuzio-Donahue et al., "Discovery of novel tumor markers of pancreatic cancer using global gene expression technology," Am J Pathol. 160(4):1239-1249 (2002).
International Preliminary Report on Patentability in International Application No. PCT/US2009/040480, dated Oct. 19, 2010, 8 pages.
International Search Report and Written Opinion in International Application No. PCT/US2009/040480, dated Nov. 30, 2009, 13 pages.
Johnson et al., "Differential expression of insulin-like growth factor binding protein-5 in pancreatic adenocarcinomas: identification using DNA microarray," Molecular Carcinogenesis 45:814-827 (2006).
Joyce et al., "Stage-specific vascular markers revealed by phage display in a mouse model of pancreatic islet tumorigenesis," Cancer Cell 4:393-403 (2003).
Kelly et al., "Detection of vascular adhesion molecule-1 expression using a novel multimodal nanoparticle," Circ Res 96: 327-336 (2005).
Kelly et al., "In vivo imaging of molecularly targeted phage," Neoplasia 8:1011-1018 (2006).
Kelly et al., "Isolation of a colon tumor specific binding peptide using phage display selection," Neoplasia 5: 437-444 (2003).
Kelly et al., "Targeted nanoparticles for imaging incipient pancreatic ductal adenocarcinoma," PLOS Medicine, 5(4):657-668 (2008).
Kelly et al., "High-throughput identification of phage-derived imaging agents," Mol Imaging, Jan.-Mar. 2006, 5:24-30.
Kim et al., "Comparative oncogenomics identifies NEDD9 as a melanoma metastasis gene," Cell 125:1269-1281 (2006).
Kirby et al., "Neuropeptide Y: Y1 and Y2 affinities of the complete series of analogues with single D-residue substitutions," J Med Chem, 36:3802-3808 (1993).
Kirby et al., "Y1 and Y2 receptor selective neuropeptide Y analogues: evidence for a Y1 receptor subclass," J Med Chem 38:4579-4586 (1995).
Lee et al., "An early evaluation of malignant tendency with plectin expression in human colorectal adenoma and adenocarcinoma," Journal of Medicine, 35(1-6):141-149 (2004).
Lee et al., "Gene Expression in Temporal Lobe Epilepsy is Consisten with Increased Release of Glutamate by Astrocytes," Mol. Med., 13:1-13 (2007).
Leung, "Lys-Thr-Leu-Leu-Pro-Thr-Pro-cross-linked iron oxide-Cy5.5 [PTP-CLIO-Cy5.5]," Retrieved from the internet: URL:http://www.ncbi.nlm.nih.gov/bookshelf/br.fcgi?book=micad&part=KTLLPTP-CLIO-Cy55 [retrieved on Sep. 29, 2011].
Li et al., "Pancreatic cancer," Lancet 363:1049-1057 (2004).
Maser et al., "Chromosomally unstable mouse tumours have genomic alterations similar to diverse human cancers," Nature 447:966-971 (2007).
Misek et al., "Oligonucleotide-directed microarray gene profiling of pancreatic adenocarcinoma," Methods Mol Med 103:175-187 (2005).
Montet et al., "Imaging pancreatic cancer with a peptide-nanoparticle conjugate targeted to normal pancreas," Bioconjug Chem 17:905-911 (2006).
Murtaugh et al., "A case of mistaken identity? Nonductal origins of pancreatic "ductal" cancers," Cancer Cell 11: 211-213 (2007).
Neri et al., "Targeting by affinity-matured recombinant antibody fragments of an angiogenesis associated fibronectin isoform," Nat Biotechnol 15:1271-1275 (1997).
Newton et al., "In vivo selection of phage for the optical imaging of PC-3 human prostate carcinoma in mice," Neoplasia 8:772-780 (2006).
Office Action issued in Japanese Patent Application No. 2011-505127 dated Oct. 1, 2013 (11 pages, with translation).
Office Action issued in Japanese Patent Application No. 2014-042379, dated Jun. 9, 2015, 3 pages (English translation).
Office Action issued in Japanese Patent Application No. 2014-042379, dated Apr. 12, 2016, 15 pages (with English translation).

(56) References Cited

OTHER PUBLICATIONS

Osmanagic-Myers et al., "Plectin-RACK1 (receptor for activated C kinase 1) scaffolding: a novel mechanism to regulate protein kinase C activity," J Biol Chem 279: 18701-18710 (2004).

Pelaez-Luna et al., "Resectability of presymptomatic pancreatic cancer and its relationship to onset of diabetes: a retrospective review of CT scans and fasting glucose values prior to diagnosis," Am J Gastroenterol 102:2157-2163 (2007).

Raymond et al., "Dual Role of alpha6beta4 integrin in epidermal tumor growth: tumor-suppressive versus tumor-promoting function," Mol Biol Cell 18: 4210-4221 (2007).

Reynolds et al., "Protamine as an efficient membrane-translocating peptide," Bioconjug Chem 16:1240-1245 (2005).

Rist et al., "The bioactive conformation of neuropeptide Y analogues at the human Y2-receptor," Eur. J. Biochena 247:1019-1028 (1997).

Sato et al., "Gene expression profiling identifies genes associated with invasive intraductal papillary mucinous neoplasms of the pancreas," Am J Pathol. 164(3):903-914 (2004).

Schellenberger et al., "Magneto/optical annexin V, a multimodal protein," Bioconjug Chem 15:1062-1067 (2004).

Schreiber et al., "Successful growth and characterization of mouse pancreatic ductal cells: functional properties of the Ki-RAS(G12V) oncogene," Gastroenterology 127:250-260 (2004).

Sheikh et al. Am J Physiol, 261:701-15 (1991).

Silva et al., "Comparison of the genomes of two Xanthomonas pathogens with differing host specificities," Nature: International Weekly Journal of Science, 417(6887):459-463 (2002).

Sonnenberg et al., "Plakins in development and disease," Exp Cell Res 313: 2189-2203 (2007).

Supplementary European Search Report issued in European Application No. 09 73 3422 dated Nov. 8, 2012 (17 pages).

Wunderbaldinger et al., "Crosslinked iron oxides (CLIO): a new platform for the development of targeted MR contrast agents," Acad Radiol 9 Suppl 2:S304-S306 (2002).

Yates et al., "Method to correlate tandem mass spectra of modified peptides to amino acid sequences in the protein database," Anal Chem 67: 1426-1436 (1995).

Yeo et al., "A prospective randomized trial of pancreaticogastrostomy versus pancreaticojejunostomy after pancreaticoduodenectomy," Ann Surg, Oct. 1995, 222:580-588.

Office Action in Canadian Application No. 2,758,415, dated Jan. 18, 2018, 4 pages.

\* cited by examiner

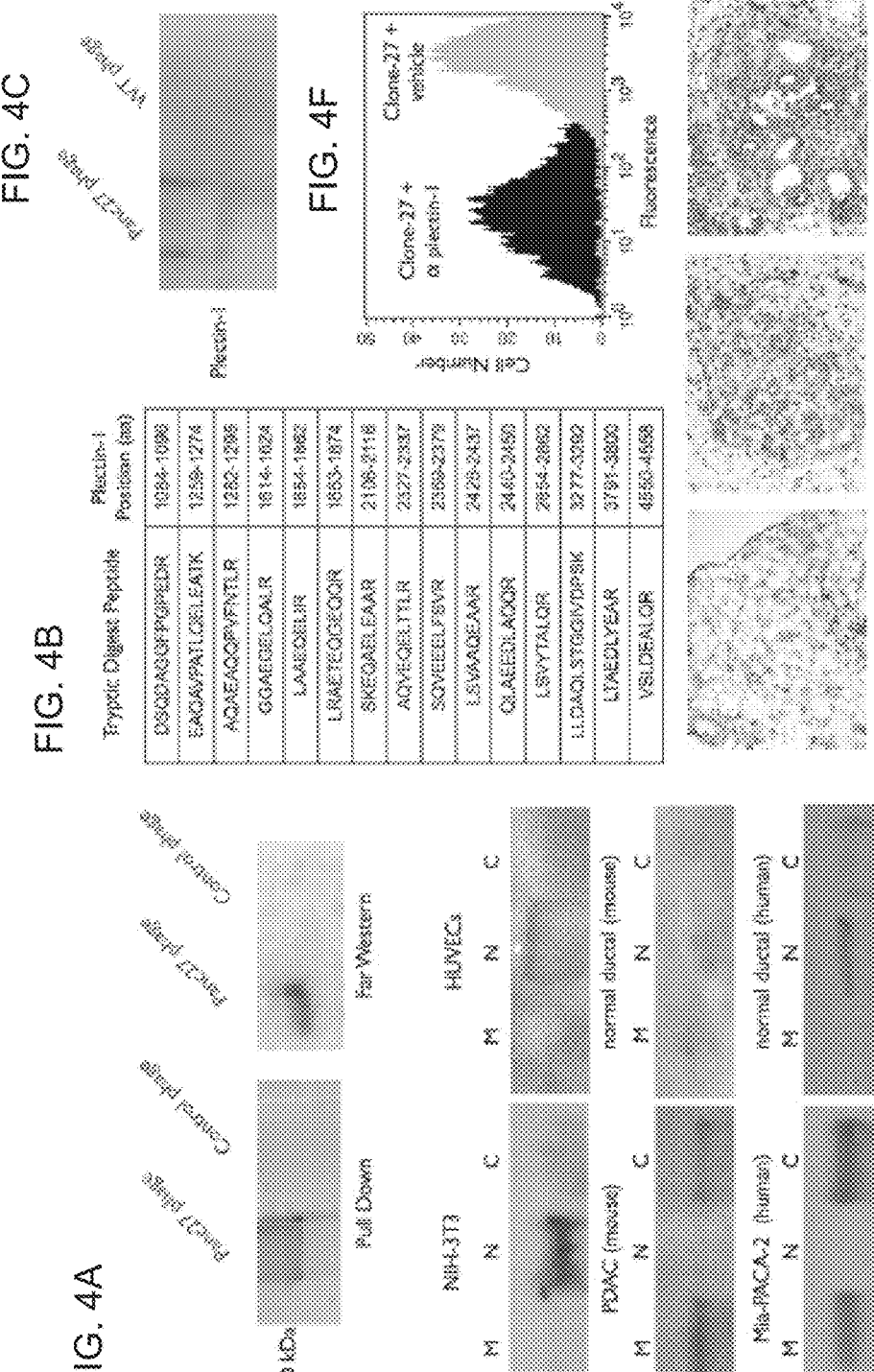

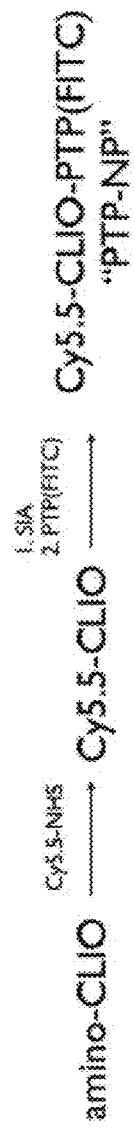
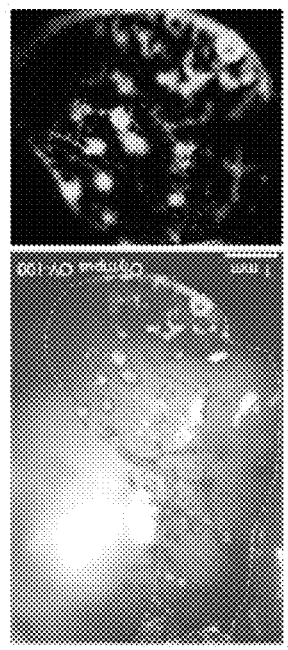
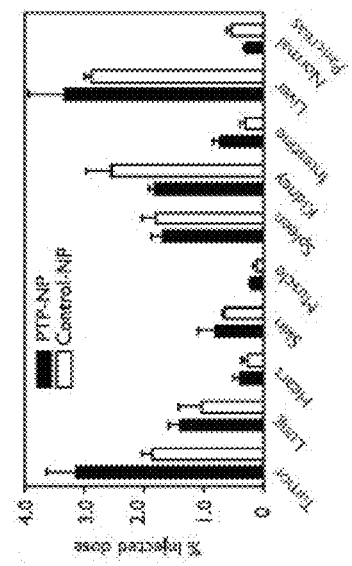
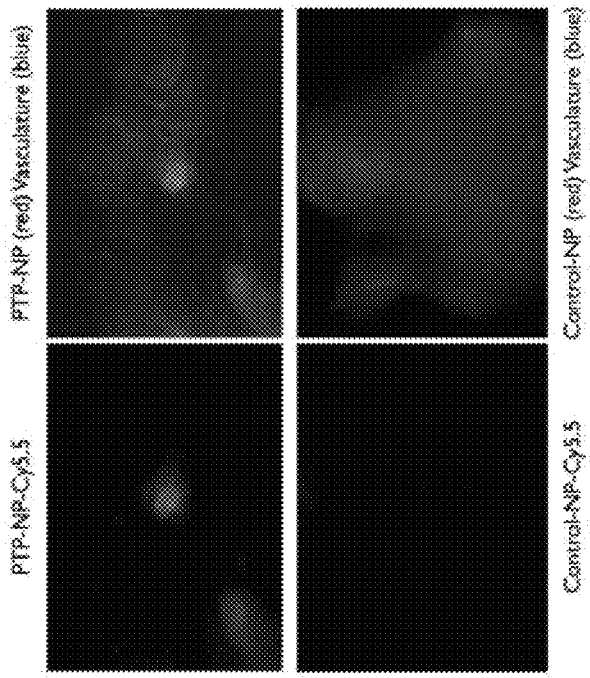
FIGURE 5A
FIGURE 5C
FIGURE 5B
FIGURE 5D

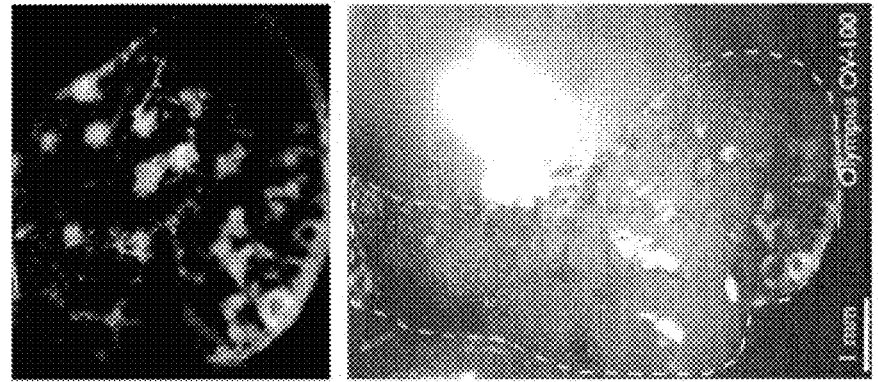
FIGURE 6C
FIGURE 6D
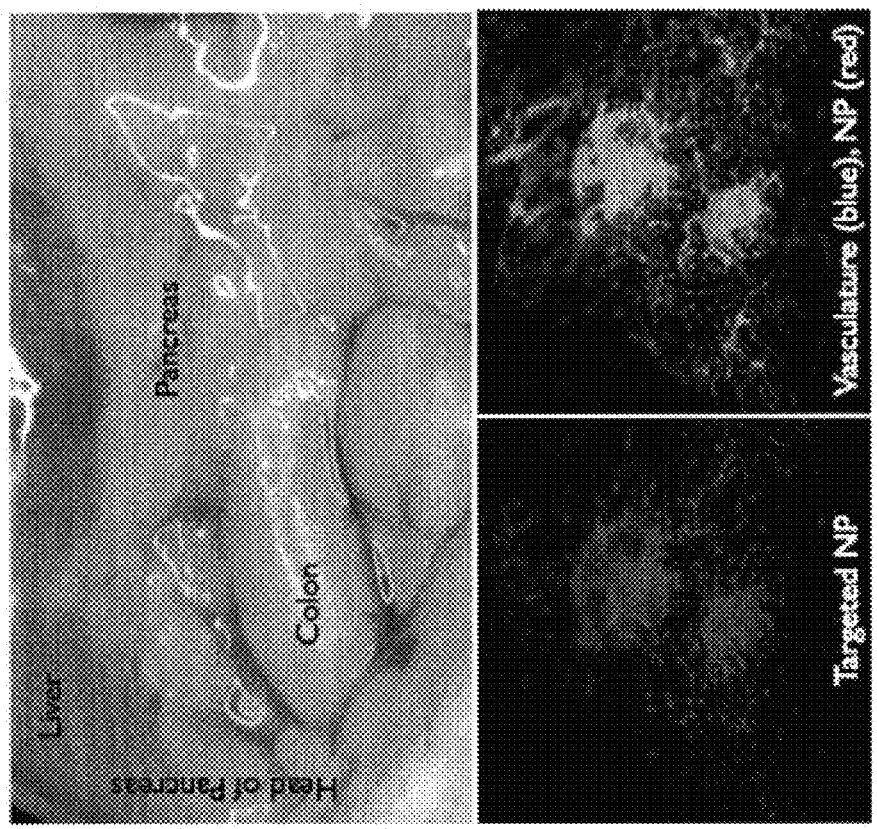
FIGURE 6A
FIGURE 6B

FIGURE 10A
Kras p53L/L Mouse
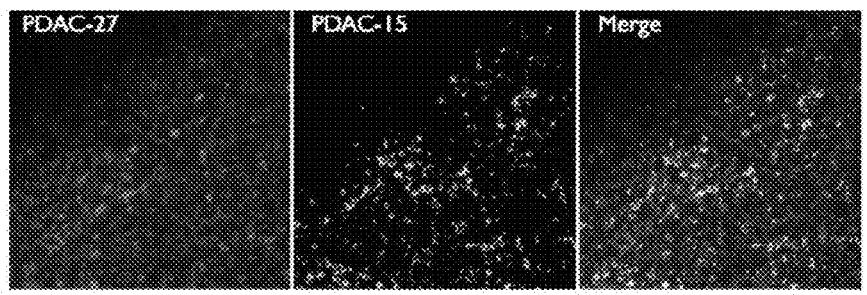
Kras p53L/L Mouse
FIGURE 10B
Wild Type Mouse
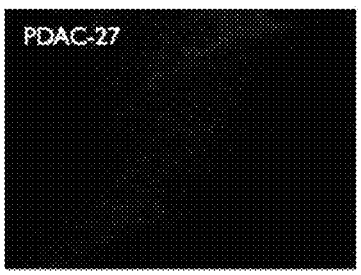
FIGURE 10C

FIGURE 11A

SEQ ID NO:24

```
MVAGMLMPRD QLPAIYEVLF REGVMVAKKD RRPRSLHPHV PGVINLQVMR   50
AMASLRARGL VRSTFAWCHF FWYLTNEGIA HLEQYLHLPP SIVAASLQRV  100
RRPVAMVMPA RRTPHVQAVQ GPLGSPPKRG PLPTEEQRLY RRKELESVSP  150
ETPVVPATTQ RTLARPGPSP APATDERDRV QKKTFTKWVN KHLIKAQRHI  200
SDLYEDLRDG HNLISLLEVL SGDSLPREKG RMRFHKLQNV QIALDYLRHR  250
QVKLVNIRRD DIADGNPKLT LGLIWTIILH FQISDIQVSG QSEDMTAKEK  300
LLLWSQRMVE GYQGLRCDNF TSSWRDGRLF NAIIHRHKPL LIDMNKVYRQ  350
TNLERLDQAF SVAERDLGVT RLLDPEDVDV FQPDEKSIIT YVSSLYDAMP  400
RVPDVQDGVR ANELQLRWQE YRELVLLLLQ WMRHHTAAFE ERRFPSSFEE  450
IEILWSQFLK FKEMELPAKE ADKNRSKGIY QSLEGAVQAG QLKVPPGYHP  500
LDVEKEWGKL HVAILEREKQ LRSEFERLEC LQRIVTKLQM EAGLCSEQLN  550
QADALLQSDV RLLAAGKVPQ RAGEVERDLD KADSMIRLLF NDVQTLRDGR  600
HPQGEQMYRR VYRLHERLVA IRTEYNLRLK AGVAAPATQV AQVTLQSVQR  650
RPELEDSTLR YLQDLLANVE ENQHRVDGAE WGVDLPSVEA QLGSHRGLHQ  700
SIEEFRAKIR RARSDEGQLS PATRGAYRDC LGRLDLQYAR LLNSSKARLR  750
SLESLHSFVA AATKELMWLN EKEEBEVGFD WSDRNTNMTA KKESYSALMR  800
ELELKEKKIK ELQNAGDRLL REDHPARPTV ESFQAALQTQ WSWMLQLCCC  850
IEAHLKENAA YFQFFSDVRE AEGQLQKLQE ALRRKYSCDR SATVTRLEDL  900
LQDAQDEKEQ LNEYKGHLEG LAKRAKAVVQ LKPRHFAHPM RGRLPLLAVC  950
DYKQVEVTVH KGDECQLVGP AQFSHWKVLS SSGSEAAVPS VCFLVPPPNQ 1000
SAQEAVTRLE AQHQALVTLN HQLHVDMKSL LAWQSLRRDV QLIRSWSLAT 1050
FRTLKPEEQR QALHSLELHY QAFLRDSQDA GGFGFEDRLM AERSYGSCSH 1100
HYQQLLQSLE QGAQEESRCQ RCISELKDIR LQLEACETRT VHRLRLPLDR 1150
RPARECAQRI AEQQKAQAEV EGLGKGVARL SAEAEKVLAL PEPSPAAPTL 1200
RSELELTLGK LEQVRSLSAI YLEKLKTISL VIRGTQGAEE VLRAHEEQLK 1250
EAQAVPATLP ELEATKASLK KLRAQAEAQQ PTFDALRDEL RGAQEVGERL 1300
QQRHGERDVE VERWRERVAQ LLERWQAVLA QTDVRQRELE QLGRQLRYYR 1350
ESADPLGAWL QDARRRQEQI QAMPLADSQA VREQLRQEQA LLEEIERHGE 1400
KVEECQRFAK QYINAIKDYE LQLVTYKAQL EPVASPAKKP KVQSGSESVI 1450
QEYVDLRTHY SELTTLTSQY IKFISETLRR MEEEERLAEQ QRAEERERLA 1500
EVEAALEKQR QLAEAHAQAK AQAEREAKEL QQRMQEEVVR REEAAVDAQQ 1550
QKRSIQEELQ QLRQSSEAEI QAKARQAEAA ERSRLRIEEE IRVVRLQLEA 1600
TERQRGGAEG ELQALRARAE EAEAQKRQAQ EEAERLRRQV QDESQRKRQA 1650
EVELASRVKA EAEAAREKQR ALQALEELRL QAEEAERRLR QAEVERARQV 1700
QVALETAQRS AEAELQSKRA SFASKTAQLE RSLQEEHVAV AQLREEAERR 1750
AQQQAEAERA REEAERELER WQLKANEALR LRLQAEEVAQ QRSLAQAEAE 1800
KQKEEAEREA RRRGKAEEQA VRQRELAEQE LEKQRQLAEG TAQQRLAAEQ 1850
ELIRLRAETE QQEQQRQLLE EELAPLQREA AAATQKRQEL EAELAKVRAE 1900
MEVLLASKAR AEEESRSTSE KSKQRLEAEA GRFRELASEA ARLRALAEEA 1950
KRQRQLAEED AARQRAEAER VLAEKLAAIG EATRLKTSAE IALKEKEAEN 2000
ERLRRLAEDE APQRRRLEEQ AAQHKADIEE RLAQLRKASD SELERQKGLV 2050
EDTLRQRBQV EEEILALKAS FEKAAAGKAE LELELQRIRE NAEDTLRSKE 2100
QAELEAARQR QLAAEEERRR REAEERVQKS LAAEEEAARQ RKAALEEVER 2150
LKANVEEARR LREBAEQESA RQLQLAQEAA QKRLQAEEKA HAFAVQQKEQ 2200
ELQQTLQQEQ SVLDQLRGEA EAARRAAEEA EEARVQAERE AAQARRQVEE 2250
AERLKQSAEE QAQARAQAQA AAEKLRKEAE QEAARRAQAE QAALRQKQAA 2300
DAEMEKHKKF AEQTLRQKAQ VEQELTTLRL QLEETDHQKN LLDEELQRLK 2350
AEATEAARQR SQVEEELFSV RVQMEELSKL KARIEAERRA LILRDKDNTQ 2400
RFLQEEAERM KQVAEEAARL SVAAQEAARL RQLAEEDLAQ QRALAEKMLK 2450
EKMQAVQEAT RLKAEAELLQ QQKELAQEQA RRLQEDKEQM AQQLAEETQG 2500
FQRTLEAERQ RQLEMSAEAE RLKLRVAEMS RAQARAEEDA QRFRKQAEEI 2550
QEKLHRTELA TQEKVTLVQT LEIQRQQSDH DAERLREAIA KLERELEKLQ 2600
QEAKLLQLKS EEMQTVQQEQ LLQETQALQQ SFLSEKDSLL QRERFIEQEK 2650
AKLEQLFQDE VAKAQQLREE QQRQQQQMEQ ERQRLVASME EARRQHEAE  2700
```

FIGURE 11B

```
EGVRRKQEEL QQLEQQRRQQ EELLAEENQR LREQLQLLEE QHRAALAHSE 2750
EVTASQVAAT KTLPNGRDAL DGPAAEAEPE HSFDGLRRKV SAQRLQEAGI 2800
LSAEELQRLA QGHTTVDELA RREDVRHYLQ GRSSIAGLLL KATNEKLSVY 2850
AALQRQLLSP GTALILLEAQ AASGFLLDPV RNRRLTVNEA VKEGVVGPEL 2900
HHKLLSAERA VTGYKDPYTG QQISLFQAMQ KGLIVREHGI RLLEAQIATG 2950
GVIDPVHSHR VPVDVAYRRG YFDEEMNRVL ADPSDDTKGF FDPNTHENLT 3000
YLQLLERCVE DPETGLCLLP LTDKAAKGGE LVYTDSEARD VFEKATVSAP 3050
FGKFQGKTVT IWEIINSEYF TAEQRRDLLR QFRTGRITVE KIIKIIITVV 3100
EEQEQKGRLC FEGLRSLVPA AELLESRVID RELYQQLQRG ERSVRDVAEV 3150
DTVRRALRGA NVIAGVWLEE AGQKLSIYNA LKKDLLPSDM AVALLEAQAG 3200
TGHIIDPATS ARLTVDEAVR AGLVGPEFHE KLLSAEKAVT GYRDPYTGQS 3250
VSLPQALKKG LIPREQGLRL LDAQLSTGGI VDPSKSHRVP LDVACARGCL 3300
DEETSRALSA PRADAKAYSD PSTGEPATYG ELQQRCRPDQ LTGLSLLPLS 3350
EKAARARQEE LYSELQARET FEKTPVEVPV GGFKGRTVTV WELISSEYFT 3400
AEQRQELLRQ FRTGKVTVEK VIKILITIVE EVETLRQERL SFSGLRAPVP 3450
ASELLASGVL SRAQFEQLKD GKTTVKDLSE LGSVRTLLQG SGCLAGIYLE 3500
DTKEKVSIYE AMRRGLLRAT TAALLLEAQA ATGFLVDPVR NQRLYVHEAV 3550
KAGVVGPELH EQLLSAEKAV TGYRDPYSGS TISLFQAMQK GLVLRQHGIR 3600
LLEAQIATGG IIDPVHSHRV PVDVAYQRGY FSEEMNRVLA DPSDDTKGFF 3650
DPNTHENLTY RQLLERCVED PETGLRLLPL KGAEKAEVVE TTQVYTEEET 3700
RRAFEETQID IPGGGSHGGS TMSLWEVMQS DLIPEEQRAQ LMADFQAGRV 3750
TKERMIIIII EIIEKTEIIR QQGLASYDYV RRRLTAEDLF EARIISLETY 3800
NLLREGTRSL REALEAESAW CYLYGTGSVA GVYLPGSRQT LGIYQALKKG 3850
LLSAEVARLL LEAQAATGFL LDPVKGERLT VDEAVRKGLV GPELHDRLLS 3900
AERAVTGYRD PYTEQTISLF QAMKKELIPT EEALRLLDAQ LATGGIVDPR 3950
LGFHLPLEVA YQRGYLNKDT HDQLSEPSEV RSYVDPSTDE RLSYTQLLRR 4000
CRRDDGTGQL LLPLSDARKL TFRGLRKQIT MEELVRSQVM DEATALQLRE 4050
GLTSIEEVTK NLQKFLEGTS CIAGVFVDAT KERLSVYQAM KKGIIRPGTA 4100
FELLEAQAAT GYVIDPIKGL KLTVEEAVRM GIVGPEFKDK LLSAERAVTG 4150
YKDPYSGKLI SLFQAMKKGL ILKDHGIRLL EAQIATGGII DPEESHRLPV 4200
EVAYKRGLFD EEMNEILTDP SDDTKGFFDP NTEENLTYLQ LMERCITDPQ 4250
TGLCLLPLKE KKRERKTSSK SSVRKRRVVI VDPETGKEMS VYEAYRKGLI 4300
DHQTYLELSE QECEWEEITI SSSDGVVKSM IIDRRSGRQY DIDDAIAKNL 4350
IDRSALDQYR AGTLSITEFA DMLSGNAGGF RSRSSSVGSS SSYPISPAVS 4400
RTQLASWSDP TEETGPVAGI LDTETLEKVS ITEAMHRNLV DNITGQRLLE 4450
AQACTGGIID PSTGERFPVT DAVNKGLVDK IMVDRINLAQ KAFCGFEDPR 4500
TKTKMSAAQA LKKGWLYYEA GQRFLEVQYL TGGLIEPDTP GRVPLDEALQ 4550
RGTVDARTAQ KLRDVGAYSK YLTCPKTKLK ISYKDALDRS MVEEGTGLRL 4600
LEAAAQSTKG YYSPYSVSGS GSTAGSRTGS RTGSRAGSRR GSFDATGSGF 4650
SMTFSSSSYS SSGYGRRYAS GSSASLGGPE SAVA 4684
```

PLECTIN-1 TARGETED AGENTS FOR DETECTION AND TREATMENT OF PANCREATIC DUCTAL ADENOCARCINOMA

CLAIM OF PRIORITY

This application is a continuation of U.S. patent application Ser. No. 14/479,558, filed on Sep. 8, 2014, now U.S. Pat. No. 9,387,265; which is a continuation of U.S. patent application Ser. No. 12/937,777, filed Oct. 14, 2010, now U.S. Pat. No. 8,829,159; which is a National Stage Application under 35 USC § 371 of PCT/US2009/040480, filed on Apr. 14, 2009, which claims the benefit of U.S. Provisional Patent Application Ser. No. 61/044,818, filed on Apr. 14, 2008. The entire contents of the foregoing are hereby incorporated by reference.

GOVERNMENT SUPPORT

This invention was made with government support from the United States National Institutes of Health (NIH) under grant numbers P50-CA86355, PO1-CA117969-01, K01 CA104647-03, EB004626, ROI-HL078641, ROI-HL36436, HL080731, and P01-AI 054904. The United States Government may have certain rights in the invention.

FIELD OF THE INVENTION

The present invention relates to compositions and methods for providing cancer cell biomarkers, such as pancreatic ductal adenocarcinoma (PDAC) cell biomarkers, and binding molecules for diagnosis and treatment. Specifically, methods of identifying "accessible" proteomes are disclosed for providing biomarkers, such as plectin-1, for identifying PDACs. Additionally, imaging compositions are provided comprising magnetofluorescent nanoparticles conjugated to peptide ligands for identifying PDACs. Finally, methods of treating PDAC are also discussed.

BACKGROUND OF THE INVENTION

Pancreatic ductal adenocarcinoma (PDAC) is the 4$^{th}$ leading cause of cancer death in the United States showing a rapid clinical course leading to death. Once diagnosed, PDAC has a median survival of 6 months and a 5-year survival rate of only 3 percent (Li et al., Lancet 363:1049-1057 (2004)).

As chemotherapy and radiotherapy have only modest benefits, and surgery is only possible in 20% of patients, early detection that allows surgical resection offers the best hope for longer survival (Yeo et al., Ann Surg 222:580-588 (1995); discussion 588-592). Indeed, the detection of PDAC or high-grade precursors in high-risk patient groups (e.g., hereditary cancer syndromes, chronic pancreatitis, and new-onset diabetes) represents a critical unmet need in the cancer diagnostic portfolio (Brentnall et al., Ann. Intern. Med. 131:247-255 (1999); Canto et al., Clin. Gastroenterol. Hepatol. 2:606-621 (2004)).

Currently, serum CA-19-9 is the clinically used biomarker; however, it lacks the sensitivity needed to detect early-stage PDAC (Goggins, J. Clin. Oncol. 23:4524-4531 (2005)). In addition, cross-sectional abdominal imaging has proven to be unreliable to detect early-stage PDAC in high-risk patients (Pelaez-Luna et al., Am J Gastroenterol 102:2157-2163 (2007)).

Thus a high priority in this field of medicine is the identification of biomarkers for the development of binding ligands as diagnostics, such as imaging probes for detecting pre-neoplastic/early invasive lesions and for use in treatments.

SUMMARY OF THE INVENTION

The present invention relates, at least in part, to compositions and methods for providing cancer cell biomarkers, such as pancreatic ductal adenocarcinoma (PDAC) cell biomarkers, and binding molecules for diagnosis and treatment. Specifically, methods of identifying "accessible" proteomes are disclosed for providing biomarkers, such as plectin-1, for identifying PDACs. Additionally, imaging compositions are provided comprising magnetofluorescent nanoparticles conjugated to peptide ligands for identifying PDACs.

Described herein are biomarkers for identifying cancer cells, as opposed to noncancer cells, for use in diagnostics and treatments, such as for providing binding partners (i.e., ligands) such as peptides, small molecules, peptide mimetics, nonpeptide mimetics, antibodies and the like.

In one aspect, the invention provides biomarkers of cancer cells, wherein the biomarker comprises a plectin-1 fragment and is located on the external membrane of the cancer cell. In some embodiments, the biomarker fragment includes any one of the sequences set forth in SEQ ID NOs: 9-23. Further, the present inventions are not limited by the type of cancer cell. Indeed a variety of cancer cell types are contemplated, including but not limited to a gastrointestinal cancer cell, a hepatobiliary cancer cell, a gall bladder cancer cell, a pancreatic cancer cell, a lung cancer cell, a mesothelioma cancer cell, a bladder cancer cell, a prostate cancer cell, a breast cancer cell, a head cancer cell, a neck cancer cell, a thyroid cancer cell, a uterine cancer cell, a cervix cancer cell, a uterine-cervix cancer cell, a blood cancer cell, a white blood cancer cell, a bone marrow cancer cell, a pleura cancer cell, a pleural fluid cancer cell, a prostate cancer cell, and the like. In some embodiments, the cancer cell is selected from the group consisting of a pancreatic cancer cell and a pancreatic ductal adenocarcinoma cell (PDAC). In some embodiments, the biomarker comprises SEQ ID NO:24 or an isoform thereof. In some embodiments, the biomarker comprises a peptide or fragment thereof encoded by human mRNA sequences, such as those described in the GenBank Database at Acc. Nos. NM_000445.2; NM_201378.1; NM_201379.1; NM_201380.2; NM_201381.1; NM_201382.1; NM_201383.1; and/or NM_201384.1. In some embodiments, the biomarker binds to a phage-displayed peptide.

In an additional aspect, the present invention features plectin-1 ligands including a first portion including a plectin-1 binding moiety, coupled to a second portion that includes a detectable moiety or a therapeutic agent. In some embodiments, the plectin-1 binding moiety is an amino acid sequence selected from the group consisting of SEQ ID NOs: 1, 2, or 4-8, or a peptidomimetic thereof. In some embodiments, the plectin-1 binding moiety is an anti-plectin-1 antibody or antigen-binding fragment thereof, a small molecule, or an aptamer. In some embodiments, the plectin-1 binding moiety is coupled to a nanoparticle, a microparticle, or a solid phase reagent. The detectable moiety can be selected from the group consisting of a radioactive isotope, a magnetic compound, an x-ray absorber, a chemical compound, a biological tag, and a fluorescent molecule. The therapeutic agent can be, e.g., a cytotoxic moiety or an immunomodulatory moiety (e.g., a compound that enhances the immune response to the tumor, e.g., an inflammatory cytokine such as interleukin-1 (IL-1), and tumour necrosis factor-alpha (TNF-a).

In some embodiments, there is a linker between the first portion and the second portion, e.g., a flexible amino acid sequence, e.g., a photolinker.

In some embodiments, the second portion includes a physiologically inert nanoparticle, e.g., in addition to or as the detectable moiety or therapeutic agent.

The peptide ligand of claim 8, wherein the nanoparticle is magnetic, fluorescent, or radioactive. Exemplary nanoparticles include crosslinked iron oxide nanoparticles (CLIOs), superparamagnetic iron oxide nanoparticles (SPIONs), and cross-linked superparamagnetic iron oxide nanoparticles.

In some embodiments, the second portion comprises a fluorochrome, e.g., with an excitation maxima range of 500 nm-1000 nm. Ins some embodiments, the fluorochrome is a near infrared fluorochrome, e.g., with an excitation maxima range of 650-680 nm, e.g., a cyanine derivative such as cyanine 5.5.

In some, the second portion comprises a crosslinked iron oxide nanoparticle conjugated to a NIRF, e.g., cyanine 5.5 (CLIO-Cy5.5).

In some embodiments, the invention features peptide ligands including or consisting essentially of SEQ ID NO:1 coupled to a nanoparticle, optionally with a linker, e.g., a fluorescently labeled linker, and a nanoparticle, e.g., a magnetofluorescent nanoparticle. In some embodiments, one or both of the linker and the particle is fluorescent. In some embodiments, the magnetofluorescent nanoparticle comprises a near infrared (NIR) fluorochrome (NIRF).

In another aspect, plectin-1 binding moiety is the invention provides ligands for a biomarker, wherein the ligand is selected from the group consisting of a peptide ligand, a mimetic, a small molecule, and an antibody. In some embodiments, the ligand is a peptide. Thus, in some embodiments, the invention provides a peptide ligand including any one of amino acid SEQ ID NOs:1-8, for binding to a pancreatic ductal adenocarcinoma cell. In some embodiments, the peptide ligand binds to a biomarker for a pancreatic ductal adenocarcinoma cell molecule, such as plectin-1. Thus, in some embodiments, the invention provides a peptide ligand including amino acid SEQ ID NO:1, for binding to a pancreatic ductal adenocarcinoma cell. In some embodiments, the ligand binds to a receptor on a pancreatic cancer cell. In some embodiments, the ligand binds to a biomarker of a pancreatic cancer cell. In some embodiments, the biomarker is expressed differently in a cancer cell than in a noncancer cell. In some embodiments, the ligand has a different binding pattern to receptors of a cancer cell compared to a noncancer cell. In some embodiments, the ligand binds to biomarkers in a different location in a cancer cell than in a noncancer cell. In some embodiments, the ligand binds to a greater number of receptors of a cancer cell than of a noncancer cell. In some embodiments, the ligand binds to a greater number of cancer cells than to noncancer cells. In some embodiments, the ligand identifies a biomarker of a cancer cell. In some embodiments, the ligand binds to a biomarker of a cancer cell. In some embodiments, the biomarker is plectin-1. In some embodiments, the ligand derives from a random phage-displayed peptide library. In some embodiments, the peptide ligand derives from a random phage-displayed peptide library. In some embodiments, the ligand derives from a phage-displayed peptide. In some embodiments, the ligand is synthetic.

In another aspect, the invention provides bacteriophage displaying a peptide ligand bound to a pancreatic ductal adenocarcinoma cell. In some embodiments, the bacteriophage includes a fluorescent molecule, e.g., a fluorescein isothiocyanate.

In yet another aspect, the invention features isolated bacteriophage displaying a peptide ligand eluted from a pancreatic ductal adenocarcinoma cell, e.g., an isolated bacteriophage displaying a peptide ligand comprising SEQ ID NO:1.

In a further aspect, the invention provides diagnostic peptides, e.g., a peptide including SEQ ID NO:1. In some embodiments, the diagnostic peptides are coupled to a label, e.g., a label selected from the group consisting of a radioactive isotope, a chemical compound, a biological tag, and a fluorescent molecule. In some embodiments, the label is selected from the group consisting of $I^{125}$, biotin, histadine tag, a fluorochrome derived from a fluorochrome-hydrosuccinimide ester, and a fluorescein isothiocyanate. In some embodiments, the diagnostic peptide further comprises a linker. In some embodiments, the linker is a photolinker. In some embodiments, the photolinker is sulfosuccinimidyl 2-[7-amino-4-methylcoumarin-3-acetamido]ethyl-1,3 dithiopropionate. In some embodiments, the linker is labeled, e.g., is fluorescently labeled. In some embodiments, the fluorescently labeled linker is a GGSK(Fluorescein isothiocyanate (FITC))C (SEQ ID NO:27) linker.

In some embodiments, the peptide is conjugated to a physiologically inert nanoparticle. In some embodiments, the nanoparticle is selected from the group consisting of a crosslinked iron oxide nanoparticle (CLIO), a superparamagnetic iron oxide nanoparticle (SPIONs), a cross-linked superparamagnetic iron oxide nanoparticle, et cetera. In some embodiments, the nanoparticle further comprises a fluorophore, e.g., a near infrared (NIR) fluorochrome, e.g., with an excitation/emission maxima at 785 nm/810 nm or an excitation/emission maxima at 675 nm/694 nm. In some embodiments, the near infrared (NIR) fluorochrome is cyanine 5.5 or a derivative thereof.

In some embodiments, the diagnostic peptide is linked to a magnetofluorescent nanoparticle, e.g., a crosslinked iron oxide nanoparticle conjugated to cyanine 5.5 (CLIO-Cy5.5).

In another aspect, the invention provides diagnostic compositions including peptides including SEQ ID NO:1, and optionally one or both of a fluorescently labeled linker and a magnetofluorescent nanoparticle. In some embodiments, the diagnostic compositions include a peptide ligand including SEQ ID NO:1 coupled to a fluorescently labeled linker molecule conjugated to a crosslinked iron oxide nanoparticle, wherein the nanoparticle is conjugated to a near infrared (NIR) fluorochrome (NIRF).

In a further aspect, the invention provides diagnostic compositions including a peptide, e.g., SEQ ID NO:2 (i.e., KTLLPTPGGSK), e.g., a FITC-labeled peptide including SEQ ID NO:2 (i.e., KTLLPTPGGSK(Fluorescein isothiocyanate (FITC))C), conjugated to a crosslinked iron oxide nanoparticle, wherein the nanoparticle is further conjugated to a fluorochrome, e.g., a NIRF, e.g., a cyanine derivative such as cyanine 5.5 (CLIO-Cy5.5).

Also provided herein is the use of the plectin-1 binding compounds described herein for the diagnosis or treatment of pancreatic ductal adenocarcinoma, and in the manufacture of a medicament for the diagnosis or treatment of pancreatic ductal adenocarcinoma.

In another aspect, the invention provides methods for detecting a cancer cell in a subject. The methods include providing cells or tissue from the subject (e.g., from a biopsy, or from plasma or blood, i.e., circulating tumor cells from the subject); and detecting the presence or subcellular localization of plectin-1 protein in the cells or tissue, wherein the presence of cell membrane expression of plectin-1 indicates the presence of a cancer cell. In some embodiments, the absence of plectin-1, or the presence of only cytoplasmic and/or nuclear expression of plectin-1, indicates that there are no cancer cells in the cells or tissue.

In some embodiments, detecting subcellular localization of plectin-1 expression in the sample includes contacting the sample with an agent that binds to plectin-1 protein, optionally comprising a detectable moiety; and detecting subcellular localization of the agent; wherein the subcellular localization of the agent indicates the subcellular localization of plectin-1 expression. In some embodiments, the agent that binds to plectin-1 protein is a peptide ligand as described herein, or an antibody or antigen-binding portion thereof that is specific for plectin-1. In some embodiments, subcellular localization is detected using laser scanning microscopy, immunohistochemistry, fluorescent microscopy, and/or radiography. Other methods, including Raman spectroscopy, optical coherence tomography (OCT), detection of radiation (e.g., x-ray) scattering or absorption, ultrasound, and isotope detection, can also be used.

In yet another aspect, the invention provides methods for detecting pancreatic ductal adenocarcinoma (PDAC) or precursor pancreatic intraepithelial neoplasis (PanINs) in a subject in vivo. The methods include identifying a subject who is at risk for, or suspected of having, PDAC; administering to the subject a diagnostic composition as described herein; and detecting the presence of the peptide ligand in the pancreas of the subject using an in vivo imaging device. The presence of the peptide ligand in the pancreas indicates that the subject has PDAC. In some embodiments, the peptide ligand is administered via intradermal, intramuscular, intraperitoneal, intravenous, subcutaneous, oral, and/or gastric routes. In some embodiments, the in vivo imaging device is selected from the group consisting of magnetic resonance imagers (MRI), intravital laser scanning microscopes, endoscopes, and radiographic imagers.

Also provided herein are methods for treating pancreatic ductal adenocarcinoma (PDAC) in a subject. The methods include identifying a subject who is at risk for, or suspected of having, PDAC; administering to the subject a diagnostic composition comprising a diagnostic composition as described herein; detecting localization of the peptide ligand in the pancreas of the subject using an in vivo imaging device, wherein the localization of the peptide ligand indicates the localization of PDAC cells; and surgically removing the PDAC cells.

In a further aspect, the invention provides methods for treating pancreatic ductal adenocarcinoma (PDAC) in a subject. The methods include identifying a subject who is at risk for, or suspected of having, PDAC; and administering to the subject a therapeutically effective amount of a therapeutic composition as described herein, e.g., comprising a plectin-1 binding moiety coupled to a therapeutic agent. In some embodiments, the composition is administered by intradermal, intramuscular, intraperitoneal, intravenous, subcutaneous, oral, and/or gastric routes.

In some embodiments, the therapeutic agent is a cytotoxic or cytostatic moiety selected from the group consisting of a therapeutic drug, a radioisotope, molecules of plant, fungal, or bacterial origin, and biological proteins. In some embodiments, the therapeutic agent is a phototoxic or immunomodulatory compound.

Also provided herein are peptides consisting essentially of an amino acid sequence selected from the group consisting of any of SEQ ID NOs: 9-23.

In yet another aspect, the invention provides methods for identifying a pancreatic cancer cell peptide ligand. The methods include a) providing i) a phage-displayed random combinatorial peptide library, wherein the peptide ranges from 7-12 mer, ii) a receptor for the peptide, wherein the receptor derives from a pancreatic cancer cell's "accessible" proteome, and iii) a phage-displayed peptide-receptor binding assay; b) performing a phage-displayed peptide-receptor binding assay, and c) identifying a pancreatic cancer cell biomarker. In some embodiments, the cancer cell is a pancreatic ductal adenocarcinoma cell. In some embodiments, the phage-displayed random combinatorial peptide library comprises amino acid SEQ ID NO:1. In some embodiments, the phage further comprises a fluorochrome-label. In some embodiments, the label is selected from the group consisting of a fluorochrome-hydrosuccinimide ester, cyanine 5.5, and fluorescein isothiocyanate. In some embodiments, the pancreatic cancer cell's "accessible" proteome includes components selected from the group consisting of proteins, subcellular fractions, cell lysate, and whole cells. In some embodiments, the receptor is plectin-1. In some embodiments, the peptide-receptor binding assay is selected from the group consisting of Enzyme-Linked ImmunoSorbent Assay (ELISA), a High Performance Liquid Chromatography (HPLC) assay, a competitive binding assay, an immunofluorescence assay, a radioactive assay, an intact cell binding assay, an SDS/PAGE gel assay, a fluorescent Microscopy assay and flow Cytometry assay. In some embodiments, the identifying step includes but is not limited to detecting differential gene expression, protein processing, carbohydrate processing, trafficking, intracellular location, cell surface expression, binding pattern, and binding amount.

In an additional aspect, the invention provides methods for identifying a peptide ligand for a pancreatic cancer cell. The methods include a) providing i) a pancreatic cancer cell, wherein the cancer cell expresses a receptor, ii) a non-cancer cell, iii) a phage-displayed peptide ligand, and, and iv) a peptide ligand-receptor binding assay; b) adding the peptide ligand to a cancer cell and to a non-cancer cell; and c) performing a peptide binding assay to distinguish the cancer cell from the non-cancer cell. In some embodiments, the method further comprises eluting the peptide ligand from the receptor. In some embodiments, the method further comprises sequencing the phage displayed peptide. In some embodiments, the receptor is an immobilized receptor-binding partner. In some embodiments, the immobilized receptor is immobilized on a support material selected from the group consisting of a biopsy specimen, a bead, a membrane, a gel, a membrane, and a plastic.

In another aspect, the invention provides methods for diagnosing a cancer in a subject. The methods include providing a sample, e.g., a biopsy sample, from a patient, and a diagnostic composition including a peptide ligand, wherein the peptide ligand includes SEQ ID NO:1, optionally conjugated to a detectable moiety, adding the peptide to the sample, and detecting the diagnostic composition, e.g., by detecting the detectable moiety in the sample. In some embodiments, the imaging includes but is not limited to laser scanning microscopy, immunohistochemistry, fluorescent microscopy, radiographic imaging and the like.

In a further aspect, the invention provides in vivo methods for diagnosing a cancer. The methods include identifying a subject at risk for or suspected of having pancreatic cell cancer; administering a diagnostic composition comprising a peptide ligand of SEQ ID NO:1 conjugated to an imaging molecule to the subject, and imaging the imaging molecule within the subject using in vivo imaging. In some embodiments, the pancreatic cell cancer is a pancreatic ductal adenocarcinoma. In some embodiments, the imaging molecule is a magnetofluorescent particle. In some embodiments, the magnetofluorescent particle comprises a near infrared (NIR) fluorochrome (NIRF). In some embodiments, the composition is administered via route selected from the group consisting of intradermal, subcutaneous, intraperitoneal, intravenous, intraarterial, oral, and gastric routes. In some embodiments, the in vivo imaging includes but is not limited to magnetic resonance imaging (MRI), intravital laser scanning microscopy, endoscopy, and radiographic imaging.

In another embodiment, the present invention provides methods for surgically removing pancreatic cancer cells. The methods include a) providing, i) a composition comprising a peptide for distinguishing a pancreatic cancer cell from a pancreatic non-cancer cell, wherein the peptide is SEQ ID NO:1, ii) a subject known to have pancreatic cancer, iii) an in vivo imaging device, and b) administering the composition to a subject, c) imaging pancreatic cancer cells in vivo with the imaging device, and d) removing pancreatic cancer cells from the subject. In some embodiments, the administering is an intravenous injection of 30 mg Fe/kg (milligram Iron/kilogram). In some embodiments, the administering is an intravenous injection of 2.6 mg/kg.

The present invention provides a method of treating a patient with cancer, comprising, a) providing, i) a cancer patient in need of treatment, ii) a pharmaceutical composition comprising a ligand, wherein the ligand binds to a biomarker of the present invention, and b) administering the treatment composition to the patient. In some embodiments, the pharmaceutical composition further comprises a therapeutic agent. In some embodiments, the therapeutic agent is selected from the group consisting of a fusion protein, a toxin, a drug. The present inventions are not limited by the type of cancer. Indeed, various types of cancer are contemplated for use with the detection methods of the present inventions including but not limited to lung cancer, bladder cancer, head and/or neck cancer, breast cancer, esophageal cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, stomach cancer, prostate cancer, testicular cancer, ovarian cancer; cervical cancer, endometrial cancer, uterine cancer, pancreatic cancer, colon cancer, colorectal, gastric cancer, kidney cancer, bladder cancer, lymphoma cancer, spleen cancer, thymus cancer, thyroid cancer, brain cancer, neuronal cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, white blood cell cancer (e.g., lymphoma, leukemia, etc.), hereditary non-polyposis cancer (HNPC), colitis-associated cancer, etc. Cancers are further exemplified by sarcomas (such as osteosarcoma and Kaposi's sarcoma).

The present invention provides a method of treating a patient with pancreatic cancer, comprising, a) providing, i) a cancer patient in need of treatment, ii) a pharmaceutical composition comprising a ligand, wherein the ligand binds to plectin-1 or a fragment thereof, and b) administering the treatment composition to the patient. In some embodiments, the pharmaceutical composition further comprises a therapeutic agent. In some embodiments, the therapeutic agent is selected from the group consisting of a fusion protein, a toxin, and a drug.

In an additional aspect, the present invention provides methods of treating a subject who has pancreatic cancer. The methods include identifying a subject in need of treatment, e.g., on the basis that they have pancreatic cancer, and administering a therapeutically effective amount of a pharmaceutical composition including a peptide including SEQ ID NO:1 linked to a cytotoxic agent, e.g., a toxin or a drug.

In another aspect, the present invention provides methods for identifying a cancer cell-binding partner (receptor) having selective affinity for a peptide ligand. The methods include selectively immobilizing a diverse population of binding molecules to a solid support, contacting (e.g., simultaneously contacting) the diverse population immobilized on the solid support with one or more peptide ligands and determining at least one binding molecule which selectively binds to one or more of the peptide ligands, including those expressed by a bacteriophage. Also provided are methods for identifying peptide ligands having selective affinity for a tumor antigen (binding molecule). The methods include selectively immobilizing a tumor antigen to a solid support, contacting (e.g., simultaneously contacting) the immobilized tumor antigen on the solid support with one or more peptide ligands and identifying at least one peptide ligand which selectively binds to one or more of the tumor antigens. Also provided are isolated binding peptides ("peptide ligands") that are selective for a tumor antigen, in particular peptide ligands for plectin-1.

Also described herein are rapid and efficient methods for the identification of binding molecules that exhibit selective affinity for one or more peptide ligands of interest. The methods are advantageous in that they allow the simultaneous screening of multiple binding molecules against multiple peptide ligands of interest. Moreover, very little information is required regarding the identity or function of either the binding molecule or the ligand for use in the present inventions. For example, diverse populations of binding molecules can be simultaneously screened against diverse populations of peptide ligands to rapidly identify numerous molecules exhibiting a desired binding specificity. The methods described herein can therefore be advantageously applied for the discovery of specific reagents, such as peptide ligands and biomarkers, for diagnosis and treatment of human diseases.

Definitions

To facilitate an understanding of the present invention, a number of terms and phrases are defined below:

The use of the article "a" or "an" is intended to include one or more. As used in this application, the singular form "a," "an," and "the" include plural references unless the context clearly dictates otherwise. For example, the term "an agent" includes a plurality of agents, including mixtures thereof.

As used herein, the term "patient" or "subject" is an individual having symptoms of, or at risk for, pancreatic cancer or other malignancy. Patients may be human or non-human and may include, for example, animal strains or species used as "model systems" for research purposes, such a mouse model as described herein. A patient may include either adults or juveniles (e.g., children). The term "patient", further refers to any living organism, preferably a mammal (e.g., human or non-human) that may benefit from the administration of compositions contemplated herein.

As used herein, the term "animal" refers to any animal, preferably a mammal, and more preferably, the mammal includes, without limitation, human and non-human animals such simians, rodents, ovines, bovines, ruminants, lagomorphs, porcines, caprines, equines, canines, felines, ayes, etc. Preferred non-human animals are members of the Order Rodentia (e.g., mouse and rat), sheep, pig, rabbit or cattle.

As used herein, the term "benefit" refers to but is not limited to a diagnostic assay, a diagnosis, a surgical tool, and the like.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease, from sub-clinical to full-blown disease, wherein the subject exhibits at least some of the indicia (e.g., signs and symptoms) associated with the particular disease.

As used herein, the terms "sample" and "specimen" are used in their broadest sense and encompass samples or specimens obtained from any source, including buffer solutions, saline solutions, cell culture media, etc.

As used herein, the term "biological samples" refers to samples or specimens obtained from animals (including humans, domestic animals, as well as feral or wild animals, such as ungulates, bear, fish, lagomorphs, rodents, etc.), and encompasses cells, fluids, solids, tissues, and gases. In preferred embodiments of this invention, biological samples include tissues (e.g., biopsy material), cell lines, cells isolated from tissue (whether or not the isolated cells are cultured after isolation from tissue), fixed cells (e.g., fixed for histological and/or immunohistochemical analysis), cerebrospinal fluid (CSF), serous fluid, blood, and blood products such as plasma, serum and the like. However, these examples are not to be construed as limiting the types of samples find use with the present invention.

As used herein, the term "biopsy tissue" refers to a sample of tissue that is removed from a subject for the purpose of determining if the sample contains cancerous tissue. In some embodiment, biopsy tissue is obtained because a subject is suspected of having cancer. The biopsy tissue is then examined for the presence or absence of cancer.

As used herein, the terms "peptide," "polypeptide" and "protein" all refer to a primary sequence of amino acids that are joined by covalent "peptide linkages." In general, a peptide consists of fewer amino acids than a full-length protein, typically from 2-50 amino acids.

As used herein, the term "polypeptide" may encompass both peptides and proteins. A peptide, polypeptide or protein may be synthetic, recombinant or naturally occurring. A synthetic peptide is a peptide that is produced by artificial means in vitro (e.g., was not produced in vivo). A "protein", "peptide", or "polypeptide" amino acid sequence may also comprise chemical compounds.

As used herein, the term "phage" or "φ" is synonymous to a "bacteriophage" refers to a virus, for example, a M13, T4, and the like, that infects a bacterium, such as an E. coli. Phage may also refer to an individual virion.

As used herein, the term "phage displayed peptide" or "bacteriophage displayed peptide" or "phage-displayed peptide" refer to a bacteriophage viron expressing one peptide nucleic acid sequence where the peptide is located on the outside surface of the virion. One virion may display one peptide or multiple copies of the peptide, such as five copies, seven copies, et cetera.

As used herein, the term "phage display" in reference to a library refers to a selection technique in which a library of peptides or protein or variants thereof expressed on the outside of a phage virion, while the genetic material encoding each variant resides on the inside variants, for example, a commercial Ph.D.™-7 Phage Display Peptide Library (New England Biolabs) provides 7 mer peptides in excess of two billion independent clones, a Ph.D.-12 Phage Display Peptide Library (New England Biolabs) provides 12 mer peptides, a noncommercial Phage Display Peptide Library provides a variety of peptide sizes from a several sources, randomly generated or chosen, such as for a certain cell type or ligand, and the like.

The terms "isolated" and "purified" in the context of "peptide sequences" refer to the separation of the desired peptide sequence(s) from non-desired peptide sequences and other contaminants (e.g. phage virions not expressing the desired peptide sequence, truncated or misformed synthetic peptides, lipids, carbohydrates, nuclei acids, etc.). The terms "isolated" and "purified" do not necessarily mean isolated and purified to 100% homogeneity, although this is also contemplated. Rather, the terms mean isolated and purified to at least 50% homogeneity. In a preferred embodiment, the peptide sequences are isolated and purified to at least 75% homogeneity. In a more preferred embodiment, the peptide sequences are isolated and purified to at least 90% homogeneity. After isolation and/or purification, the peptide sequences can then be conjugated to, mixed with or added to other compounds or molecules.

As used herein, the term "isolated" in reference to a "phage" or "phage virion" refers to a phage displaying a peptide obtained after one or more screening assays, such as a peptide-receptor screening assay of the present inventions, wherein a population of phage displayed peptides of a phage display library are screened for binding to a cancer cell receptor, such that a bound phage is "isolated" from a phage library upon binding to a cancer cell molecule. An "isolated phage" also refers to a phage virion eluted from a bound phage.

As used herein, the term "isolated" in reference to a peptide ligand refers to a peptide ligand encoded by an isolated phage expressing that peptide, such that the term includes but is not limited to the peptide ligand as expressed by and including the phage displayed peptide, the nucleic acid sequence of the isolated peptide, the amino acid sequence of the isolated peptide, natural and synthetic forms of the isolated peptide ligand and the like. Thus an exemplary "isolated peptide ligand" of the present inventions includes but is not limited to a peptide expressed by any one of Clones 4, 15 and 27.

As used herein, the term "derives from" or "derived from" in reference to a peptide ligand, in particular an isolated peptide ligand, refers to a peptide ligand sequence obtained from an isolated phage virion displaying that peptide. However, a peptide, peptide derivative, or peptide mimetic, analogues and mimetic compounds are also intended to be included within the definition of this term.

As used herein, the term "mimetic" refers to any molecule that mimics the binding of a ligand to a biomarker (receptor) including a peptide, a non-peptide mimetic, a small molecule mimetic and the like.

As used herein, the term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

As used herein, the term "desired" in reference to a peptide ligand refers to a peptide ligand capable of identifying a cancer cell. As used herein, the term "desired" in reference to a binding partner for a peptide ligand refers to a biomarker, including but not limited to a cancer cell biomarker.

As used herein, the term "fluorochrome derived from" in reference to a fluorochrome refers to any fluorochrome with a similarity of structure, for example, a fluorochrome with an ester group and the fluorochrome after loosing the charged ester group in a covalent linkage to a peptide, any of a family of fluorochrome compounds, such as a fluorescein (IUPAC: 3',6'-dihydroxyspiro[2-benzofuran-3,9'-xanthene]-1-one) family of compounds, including related and similar compounds, but not limited to fluorescein isothiocyanate, fluorescein isothiocyanate isomer I, and the like.

As used herein, the term "biomarker" refers to generally a molecule or substance that is an indicator of a biologic state, such as protein or chemical for distinguishing a specific stage of development, for example, distinguishing a pluripotent cell, a stem cell, a differentiated cell, such as a nerve cell, from other cells. A biomarker is an indicator of a normal biologic process, such as maturation, a pathogenic process, such as cancer cell development, or a pharmacological response to a therapeutic intervention, such as indication of the resolution of a disease or loss of cancer cells where a biomarker may be lost or gained. In particular, a biomarker of the present inventions refers to a molecule with altered expression, such as increased expression, altered location, in a cancer cell compared to a noncancer cell of a similar lineage. When referring to "distinguishing a cancer cell," in particular a cancer cell from a noncancer cell, distinguishing refers to reagents and assays used to detect the expression of one or more proteins, peptides, or genes in each cell type (e.g., including but not limited to, the cancer markers of the present invention). Examples of suitable reagents include but are not limited to, peptide ligands, nucleic acid probes capable of specifically hybridizing to the gene of interest, aptamers, PCR primers capable of specifically amplifying the gene of interest, and antibodies capable of specifically binding to proteins expressed by a gene of interest including but not limited to a biomarker. Other non-limiting examples can be found in the description and examples below. The term "biomarker" in reference to a cellular molecule refers to a molecule of the present inventions for identifying a subset of cells, for example, a biomarker for identifying a pancreatic cancer from a noncancer pancreatic cell, such as plectin-1.

As used herein, the term "plectin-1" refers to any molecule comprising a fragment or portion of plectin-1, such as a fragment of the plectin-1 amino acid sequence, for example, any one of SEQ ID NOs:8-23 or 24, and fragments thereof, as well as isolated nucleic acids encoding those amino acid sequences.

As used herein, the term "peptide ligand" (or the word "ligand" in reference to a peptide) refers to a protein fragment that specifically binds to a molecule, such as a protein, carbohydrate, and the like. A receptor can be essentially any type of molecule such as polypeptide, nucleic acid, carbohydrate, lipid, or any organic derived compound. Specific examples of ligands are peptide ligands of the present inventions.

As used herein, the term "selective" or "selectively" when referring to the binding of a receptor molecule to a ligand refers to an interaction that is discriminated from unwanted or non-specific interactions. Discrimination includes but is not limited to affinity of ligand for a receptor molecule, for example, determined by ligand-receptor binding assays, such as phage displayed peptide ligand-cell binding assays, phage displayed peptide ligand biopsy screening, affinity purification, such as High-performance liquid chromatography (HPLC) and the like, competitive binding assays, panning assays, affinity assays, avidity assays, ELISA assays, etc., either qualitatively or quantitatively. For example, affinity may be measured qualitatively by a panning assay, ELISA, and the like, as shown by heat maps where affinity was depicted as mean absorbance values of indicated clones in ELISA assay) and specificity was determined by a ratio of clones' affinity to tumor cells versus normal ductal cells, for example, a specific peptide ligand binding interaction showed a 2 fold higher ratio of absorbance for PDAC cells versus normal ductal cells.

Further, affinity may be measured quantitatively by calculating an affinity constant (association constant) (K$\alpha$) by measuring the strength of binding of the components in a complex, such that components A and B where a binding equilibrium is represented by A (ligand)+B (receptor molecule)=AB, the association constant is given by [AB]/[A][B], and becomes larger with tighter binding between A and B and smaller with looser binding between A and B. As opposed to a dissociation constant (Kd) referring to a measure of the tendency of a complex to dissociate such that a dissociation constant is represented by [A][B]/[AB], where a tighter binding results in a smaller Kd while a looser binding results in a larger Kd. For example, an association constant Kd for a selective binding molecule interaction with a ligand may range from $10^{-3}$ M to a picoM value, for example, an association constant Kd for a selective binding interaction is generally greater than $10^{-3}$ M, is preferably greater than $10^{-4}$ M, is more preferably greater than $10^{-5}$ M, and further more preferably greater than $10^{-6}$ M. High affinity interactions are generally greater than $10^{-8}$ M to $10^{-9}$ M, and more preferably greater than $10^{-9}$ M.

As used herein, the term "avidity" refers to a total binding strength of a ligand with a receptor molecule, such that the strength of an interaction comprises multiple independent binding interactions between partners, which can be derived from multiple low affinity interactions or a small number of high affinity interactions.

As used herein, the term "attach", or "attachment", or "attached", or "attaching", used herein interchangeably with "bind", or "binding" or "binds' or "bound" refers to any physical relationship between molecules that results in forming a stable complex, such as a physical relationship between a ligand, such as a peptide or small molecule, with a "binding partner" or "receptor molecule." The relationship may be mediated by physicochemical interactions including, but not limited to, a selective noncovalent association, ionic attraction, hydrogen bonding, covalent bonding, Van der Waals forces or hydrophobic attraction.

The terms "specific binding" or "specifically binding" when used in reference to the interaction of a peptide (ligand) and a receptor (molecule) also refers to an interaction that is dependent upon the presence of a particular structure (i.e., an amino sequence of a ligand or a ligand binding domain within a protein); in other words the peptide comprises a structure allowing recognition and binding to a specific protein structure within a binding partner rather than to molecules in general. For example, if a ligand is specific for binding pocket "A," in a reaction containing labeled peptide ligand "A" (such as an isolated phage displayed peptide or isolated synthetic peptide) and unlabeled "A" in the presence of a protein comprising a binding pocket A the unlabeled peptide ligand will reduce the amount of labeled peptide ligand bound to the binding partner, in other words a competitive binding assay.

"Specifically binds" means that one molecule, such as a binding moiety, e.g., an oligonucleotide or antibody, binds preferentially to another molecule, such as a target molecule, e.g., a nucleic acid or a protein, in the presence of other molecules in a sample.

As used herein, the term "amino acid sequence," as used herein, refers to the primary (i.e., linear) structure of a protein, peptide, or polypeptide wherein the individual amino acids are linked by peptide bonds.

As used herein, the term "receptor," as used herein, refers to any "binding molecule" or "binding partner" (e.g., a cancer cell protein "recognized" or "bound" or "eluted from" a peptide ligand) including but not limited to a peptide, protein or glycoprotein to which an amino acid peptide sequence of the present invention appears to interact with or to specifically bind. For example, a binding molecule may reside on a cell surface or within a cell. An exemplary binding molecule is a plectin-1 molecule that interacts with SEQ ID NO:1 of the present invention. As used herein, the term "binding molecule" also refers to a molecule of sufficient size and complexity expressed by a cancer cell or tumor cell so as to be capable of selectively binding a peptide ligand. Such molecules are generally macromolecules, such as polypeptides, however include nucleic acids, carbohydrates and lipids. The size of a binding molecule is not important so long as the molecule exhibits or can be made to exhibit binding activity with a peptide ligand.

As used herein, the term "target cell" in reference to a "cancer cell" or "cell" or "host cell" refers to any cell or molecule used as a target for a peptide ligand in any of the assays of the present invention. "Target cell" also refers to any cell that either naturally expresses particular biomarkers of interest or is genetically altered so as to produce normal or mutated biomarkers.

As used herein, the term "target binding molecule" or "target receptor" refers to a binding partner molecule, both known and unknown molecules, of a peptide ligand of interest, such as an isolated peptide ligand.

The terms "variant" and "mutant" when used in reference to a polypeptide refer to an amino acid sequence that differs by one or more amino acids from another, usually a related polypeptide. The variant may have "conservative" changes, wherein a substituted amino acid has similar structural or chemical properties. One type of conservative amino acid substitution refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, preferably less than 5% and still more preferably less than 2% changes (whether substitutions, deletions, and so on).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "gene" refers to a nucleic acid (e.g., DNA) sequence that comprises coding sequences necessary for the production of a polypeptide, precursor, or RNA (e.g., rRNA, tRNA and the like). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences.

As used herein, the term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

As used herein, the term "label" as used herein refers to any atom or molecule that can be used to provide a detectable (preferably quantifiable) signal, and that can be attached to a nucleic acid or protein. Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

As used herein, the term "linker" refers to a molecule or sequence, such as an amino acid sequence, that attaches, as in a bridge, one molecule or sequence to another molecule or sequence. "Linked," "conjugated," or "coupled" means attached or bound by covalent bonds, or non-covalent bonds, or other bonds, such as van der Waals forces.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used herein, the term "epithelial cell" refers to a cuboidal-shaped, nucleated cell generally located on the surface of a tissue, such as a pancreatic ductal cell. A layer of epithelial cells generally functions to provide a protective lining and/or surface that may also be involved in transport processes. An epithelial cell is readily distinguished from a non-epithelial cell (e.g., muscle cell, nerve cell, secretory cell, etc.) using histological methods well known in the art.

As used herein, the term "endothelial cells", as used herein, refers to any cell that may provide a lining for a bodily organ comprising a lumen (e.g., blood vessels, intestines, lymphatic vessels or ducts etc.). Usually, endothelial cells provide physical and chemical protection as well a selective absorption of nutrients or other metabolically active compounds.

As used herein, "ductal cell", in reference to a pancreas, refers to any cell that forms or has the capability to form or originated from the ductal lining of ducts within and exiting from the pancreas.

As used herein, "pancreas" in reference to an organ refers to a collection of a plurality of cell types held together by connective tissue, such that the plurality of cells include but are not limited to acini calls, ductal cells and islet cells. The "acini" produce many of the enzymes, such as lipase, which are needed to digest food in the duodenum. The enzymes produced by the acini are carried to the duodenum by small channels called ducts. Typically, ductal cells are held in place by connective tissue in close proximity to vascular cells and nerve cells. Islets of Langerhans are typically embedded between exocrine acini units of the pancreas. Examples of islet endocrine cells are Alpha cells that secrete glucagon which counters the action of insulin while Beta cells secrete insulin, which helps control carbohydrate metabolism.

As used herein, "pancreatic cancer" refers to cancers that originate in the tissue that comprises a pancreas, such as a pancreatic ductal adenocarcinoma cell.

As used herein, "adenocarcinoma" refers to a cancerous tumor as opposed to an "adenoma" which refers to a benign (non-cancerous) tumor made up of cells that form glands (collections of cells surrounding an empty space).

As used herein, "pancreatic ductal adenocarcinoma cell" refers to a cancerous cell that had the capability to form or originated from the ductal lining of the pancreas. A pancreatic ductal adenocarcinoma cell may be found within the pancreas forming a gland, or found within any organ as a metastasized cell or found within the blood stream of lymphatic system.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the term "stem cell cancer markers" refers to a gene or peptide expressed by the gene whose expression level, alone or in combination with other genes, is correlated with the presence of tumorigenic cancer cells. The correlation may relate to either an increased or decreased expression of the gene (e.g. increased or decreased levels of mRNA or the peptide encoded by the gene).

As used herein, the term "instructions for using the kit for detecting cancer in the subject" includes instructions for using the reagents contained in the kit for the detection and characterization of cancer in a sample from a subject.

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "post surgical tumor tissue" refers to cancerous tissue (e.g., biopsy tissue) that has been removed from a subject (e.g., during surgery).

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "non-cancerous" in reference to a pancreatic cell refers to a cell demonstrating regulatable cell growth and functional physiology relative to its developmental stage and activity.

As used herein, the term "tumor" refers to an abnormal mass of tissue that results from excessive cell division that is uncontrolled and progressive. It is also called a neoplasm. Tumors may be either benign (not cancerous) or malignant.

As used herein, the term "tumor cell", as used herein, refers to any mass of cells that exhibits any uncontrolled growth patterns or altered physiology. Tumor cells may be derived from any tissue within an organism (e.g., a pancreatic ductal tumor cell).

As used herein, the term "cancer" is a general term for more than 100 diseases that are characterized by an uncontrolled, abnormal growth of cells. Cancer cells can spread locally or can intravasate and spread via the bloodstream and lymphatic system to other parts of the body and form metastases. Cancer cells that spread are called "malignant."

As used herein, the terms "cancer" and "cancerous" in reference to a physiological condition in mammals is typically characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, the term "malignant" refers to having the properties of anaplasia, penetrance, such as into nearby areas or the vasculature, and metastasis.

As used herein, the term "invasive," or "metastasis" as used herein, refers to any migration of cells, especially to invasive cancer cells or tumor cells. The term applies to normally invasive cells such as wound-healing fibroblasts and also to cells that migrate abnormally. Although the term is not to be limited by any mechanistic rationale, such cells are thought to migrate by defeating the body's means for keeping them sufficiently "in place" to function normally. Such cells are "invasive" if they migrate abnormally within a tissue or tumor, or escape the tissue, or invade other tissues.

As used herein, the term "cell migration" refers to the movement of a population of cells from one place to another. Such movement of cells may be normal as in the movement of neural crest cells during morphogenesis or it may be not normal such as with the movement of malignant cancer cells away from primary sites into nearby areas, the vasculature and thence, into new or secondary sites in the originating or other organs.

As used herein, the term "in vitro" refers to an artificial environment and to processes or reactions that occur within an artificial environment. In vitro environments consist of, but are not limited to, controlled laboratory conditions.

As used herein, the term "in vivo" refers to the natural environment (e.g., within an organism or a cell) and to processes or reactions that occur within that natural environment. Alternatively the term "in vitro" refers to performing a given experiment in a controlled environment outside of a living organism, such as an experiment within a laboratory Petri dish.

As used herein, the term "inhibits" in reference to a peptide ligand, for example, "a peptide ligand which inhibits malignant cell migration" or "a peptide ligand which inhibits cancer cell growth" refers to the partial or total inhibition of migration or growth respectively.

As used herein, the term "reducing cancer in a patient" in reference to a treatment refers to any treatment for decreasing the number of cancer cells in a patient, slowing the growth of cancer cells in a patient, reducing the metastasis of cancer cells in a patient and includes any type of response for either relieving cancer symptoms or increasing the life-span of a patient.

As used herein, the term "ELISA" refers to enzyme-linked immunosorbant assay. Numerous methods and applications for carrying out an ELISA are well known in the art, and provided in many sources (See, e.g., Crowther, "Enzyme-Linked immunosorbant Assay (ELISA)," in Molecular Biomethods Handbook, Rapley et al. [eds.], pp. 595-617, Humana Press, Inc., Totowa, N.J. [1998]; Harlow and Lane (eds.), Antibodies: A Laboratory Manual, Cold Spring Harbor Laboratory Press [1988]; and Ausubel et al. (eds.), Current Protocols in Molecular Biology, Ch. 11, John Wiley & Sons, Inc., New York [1994]; and Newton, et al., (2006) Neoplasia. 8:772-780). In some embodiments of the present invention, a "direct ELISA" protocol is provided, where a target-binding molecule, such as a cell, cell lysate, or isolated protein, is first bound and immobilized to a microtiter plate well. In an alternative embodiment, a "sandwich ELISA" is provided, where a target-binding molecule is attached to the substrate by capturing it with an antibody that has been previously bound to the microtiter plate well. The ELISA method detects an immobilized ligand-receptor complex (binding) by use of fluorescent detection of fluorescently labeled ligands or an antibody-enzyme conjugate, where the antibody is specific for the antigen of interest, such as a phage virion, while the enzyme portion allows visualization and quantitation by the generation of a colored or fluorescent reaction product. The conjugated enzymes commonly used in the ELISA include horseradish peroxidase, urease, alkaline phosphatase, glucoamylase or O-galactosidase. The intensity of color development is proportional to the amount of antigen present in the reaction well.

As used herein, a "pharmaceutical composition" is a composition comprising a sequence or sequences of the present invention. The pharmaceutical composition may further comprise a carrier, a pharmaceutically acceptable excipient, and the like. The terms "pharmaceutical composition" and "therapeutic composition" are used herein interchangeably. It is not intended that the pharmaceutical compositions be limited to any particular carrier or excipient or other ingredient.

As used herein, the term "therapeutic agent" refers to chemicals or drugs or proteins that are able to inhibit cell function, inhibit cell replication or kill mammalian cells, preferably human cells.

As used herein, the term "kit" is used in reference to a combination of reagents, in particular a peptide ligand of the present inventions, and other materials. It is contemplated that the kit may include reagents such as phage displayed peptides, isolated peptide ligands, peptide ligands conjugated to any one of a fluorescent marker, a nanoparticle, a conjugate for MRI, a conjugate for therapeutics, antibodies, control proteins, as well as testing containers (e.g., microtiter plates, etc.). It is not intended that the term "kit" be limited to a particular combination of reagents and/or other materials.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF THE DRAWINGS

FIG. 4A is two panels. The left panel shows a silver stained gel of mouse PDAC cells incubated with either sulfo-SAED conjugated phage Clone 27 and biotin modified phage Clone 27 or control phage, exposed to light, lysates were incubated with streptavidin coated beads. Precipitated protein was eluted with (Dithiothreitol) DTT then run on an SDS PAGE gel. The right panel is a Far Western; PDAC lysates were loaded onto an SDS PAGE gel then transferred and analyzed with clone-27 or control (no insert) biotinylated phage.

FIG. 4B is a list of tryptic digest products. A band corresponding to clone-27 affinity purified protein from 4A was cut from the gel, digested with trypsin and analyzed via mass spectrometry (SEQ ID NOs: 9-23).

FIG. 4C is a blot of affinity purified protein from 4A that was run on a sodium dodecyl sulfate polyacrylamide (SDS) PAGE gel, transferred to PVDF membrane and analyzed for the presence of plectin-1.

FIG. 4D is a set of six blots of 293T cells, human umbilical vein endothelial cells (HUVECs), mouse PDAC cells, mouse normal duct cells, Paca-2 cells (human PDAC), and normal human duct cells that were subcellularly fractionated, and the components probed for the presence of plectin-1.

FIG. 4E is a set of three photomicrographs of pancreas tissue from wild type (left), 29-week old Kras/p16$^{1/-}$ (center), and 12-week old Kras/p53 (right) mice. The tissues were embedded in OCT, frozen and stained with anti-plectin-1 antibody.

FIG. 4F is a histogram showing the results of a competition experiment in which mouse PDAC cells were incubated with FITC labeled clone 27 and either plectin-1 or vehicle then analyzed via FACS.

FIG. 5A is a schematic of conjugation of PTP to NP. Control-NP is synthesized the same way with substitution of control peptide for PTP FIG. 5B is a set of four exemplary intravital confocal microscope images of early pancreatic lesions imaged using PTP-NP (top) or control-NP (bottom) and AF750-labeled bloodpool agent.

FIG. 5C is a pair of low-magnification views of pancreatic fluorescence shows distribution of PTP-NP in distinct areas of the pancreas. White light overlay provides anatomic correlation (left). Dotted line outlines the pancreas.

FIG. 5D is a histogram showing biodistribution of PTP-NP and control-NP.

FIG. 6A is a white light image of the abdominal cavity of injected 9-week old Kras/p53$^{L/+}$ animals showing anatomic detail.

FIG. 6B is an intravital confocal microscope image of early pancreatic lesions imaged using PTP-NP (dark grey) and AF750-labeled bloodpool agent (light grey) demonstrates focal uptake distinct from the vasculature.

FIG. 6C is a low magnification view of pancreatic fluorescence showing distribution of PTP-NP in distinct areas of the pancreas.

FIG. 6D is a white light overlay image providing anatomic correlation. Dotted line outlines the pancreas.

FIG. 10A is a set of three photomicrographs of Cy5.5-labeled phage clone 27 and RITC-labeled phage clone 15 that were coinjected into Kras/p53L/L, and tumor binding analyzed via intravital confocal microscopy.

FIG. 10B is a photomicrograph of an unrelated phage clone injected into Kras/p53L/⁺ and analyzed via intravital confocal microscopy.

FIG. 10C is a photomicrograph of Cy5.5-labeled phage clone 27 injected into a wild-type mouse and analyzed via intravital confocal microscopy.

FIGS. 11A-B show an exemplary amino acid sequence for human plectin-1, SEQ ID NO:24.

DETAILED DESCRIPTION OF THE INVENTION

Figures 1A, 1B, 1C:
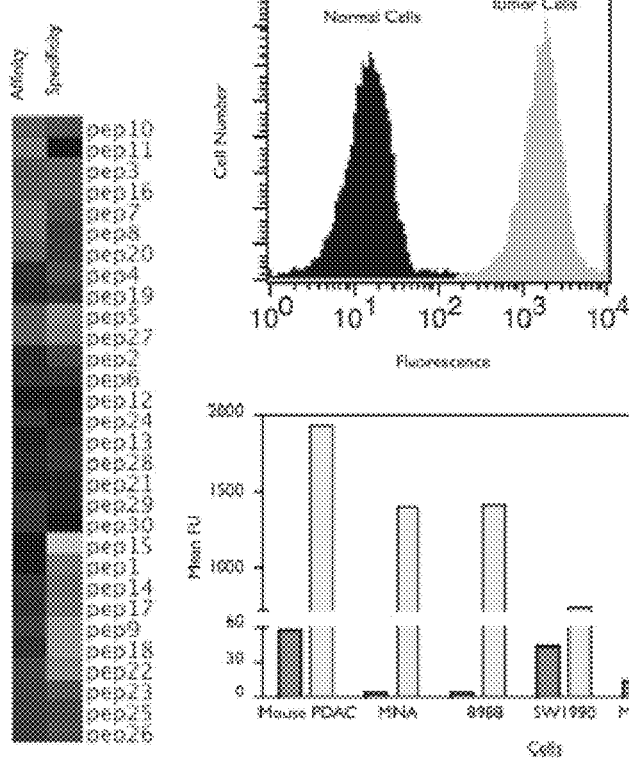
FIG. 1A is a heat map showing affinity (mean absorbance values of indicated clones in ELISA assay) and specificity (ratio of clones' affinity to tumor cells versus normal ductal cells) of selected clones. Data are displayed in terms of higher rankings (green) to lower rankings (red).
FIG. 1B is a histogram showing specificity of Clone 27 for pancreatic ductal adenocarcinoma cells validated via flow cytometry (FACS) showing FITC-labeled clone 27 bound specifically to mouse PDAC cells (FITC-27 was incubated with PDAC or normal mouse ductal cells then analyzed via FACS).
FIG. 1C is a bar graph showing FACS analysis of binding of FITC-27 or FITC unrelated phage clone (negative control) to the indicated cells. Data plotted are the mean fluorescence units obtained from FACS analysis.

The present invention relates, at least in part, to compositions and methods for providing cancer cell biomarkers, such as biomarkers of pancreatic ductal adenocarcinoma (PDAC) cell biomarkers, and binding molecules for diagnosis and treatment of cancer. "Accessible" proteomes are disclosed, and methods of use thereof for selecting biomarkers, such as plectin-1, for identifying PDACs. Imaging compositions that include magnetofluorescent nanoparticles conjugated to peptide ligands are described, and methods of use thereof for identifying PDACs. Finally, therapeutic compositions comprising antibodies and peptide ligands that bind go pletctin-1 coupled to cytotoxic agents, and methods of use thereof for the treatment of cancer, e.g., PDAC, are also described herein.

Specifically, as described herein a phage display screen and early passage PDAC cell lines isolated from mouse models were used to identify peptides that distinguish both human and murine PDAC cells from normal pancreatic ductal cells.

Described herein are peptide ligands identified using phage displayed peptides, and then developed targeted imaging agents through conjugation of the isolated peptides to a magnetofluorescent nanoparticle; the results set forth herein demonstrate that these agents can effectively detect emerging tumors in vivo and in vitro. In this approach, the binding partners of the phage displayed peptides represent a snapshot of the "accessible" proteome rather than an extensive list of overexpressed cellular proteins. Using these methods, the present inventors identified plectin-1 as a novel PDAC biomarker; expression levels of plectin-1 are modestly upregulated in cancer cells as compared to normal cells, and in addition the protein is aberrantly distributed to the cell membrane of cancerous cells and is thus accessible for probing with imaging agents as described herein.

As described herein, a multimodal nanoparticle-based targeted imaging agent (referred to herein as "PTP-NP") was developed that was capable of identifying PDAC cells in a background of normal, mucinous, and ductal metaplasia of the pancreas. In some embodiments, these imaging agents are contemplated for use in both MRI and endoscopy in high-risk patients.

I. Methods for Identifying Pancreatic Cancer Cells

Pancreatic cancer is a leading cause of cancer-related death in the United States. When pancreatic cancer is found early, surgical removal of the tumor can sometimes provide a cure. Unfortunately, this cancer rarely causes any symptoms in its early stages and the symptoms it does eventually cause include jaundice, abdominal pain, back pain, and weight loss, which are also seen in other illnesses, making early diagnosis difficult.

Magnetic resonance imaging (MRI) and other noninvasive imaging techniques are used to look at the pancreas, however by the time pancreatic tumors are large enough to show up on MRI scans, they have often already spread. Consequently, in most patients, pancreatic cancer is advanced by the time a diagnosis is made, hence surgery is no longer useful. These patients are given radiotherapy and chemotherapy but these treatments are rarely curative and most patients die within a year of diagnosis.

Thus, pancreatic ductal adenocarcinoma (PDAC) is often considered an intractable clinical problem, typically presenting with metastasis at the time of diagnosis and exhibiting profound resistance to existing therapies. Because current detection methods are unreliable, considerable ongoing efforts aimed at identifying new PDAC detection biomarkers are currently being pursued using a variety of approaches including serum proteomics, expression profiling of tumor tissue, genetic analysis of pancreatic fluid, and methods using combinatorial chemistry (see, e.g., Goggins, J Clin Oncol 23:4524-4531 (2005); Misek, et al., Methods Mol Med 103:175-187 (2005); Bloomston, et al., Cancer Res 66:2592-2599 (2006); Yates, et al., Anal Chem 67:1426-1436 (1995); and Joyce, et al., Cancer Cell 4:393-403 (2003)).

Early work to develop better diagnostic and therapeutic molecules focused on the use of antibodies for tumor recognition and drug delivery (see, e.g., Folli, et al., Cancer Res 54:2643-2649 (1994); Neri, et al., Nat Biotechnol 15:1271-1275 (1997)). However, antibody targeting in the case of molecular imaging often does not have ideal pharmacokinetics, has a limited target-to-background ratio, and furthermore has limited capacity for carrying magnetic resonance (MR)-detectable imaging agents unless extensively modified. Peptides are useful as targeting moieties with various high-throughput screening methods being utilized to select for ideal specificity, affinity, and pharmacokinetics. To their detriment as imaging agents, peptides generally have very short vascular half-lives (approximately 5 minutes) and a lower affinity than their multivalent counterparts. Therefore, a combination of multimodal nanoparticles with targeting peptides may circumvent some of these issues since they can be designed as platforms with optimized pharmacokinetics, pharmacokinetics, allow multivalent peptide attachment, are small enough for targeting, and can be internalized into the cell resulting in signal amplification through intracellular trapping (see, e.g., Kelly, et al., Circ Res 96: 327-336 (2005)).

Moreover, there is a substantial challenge in studying the early molecular changes in PDAC because of the typical presentation of PDAC at advanced stage and the corresponding lack of suitable tissue specimens. Therefore, the present discovery made use of a series of related genetically engineered mouse models of PDAC that harbor the signature gene mutations of the human disease, including Kras activation and deletion of the p53 or Ink4a/Arf tumor suppressors (see Bardeesy et al. Proc Natl Acad Sci U.S.A. 103: 5947-5952 (2006); and Aguirre et al., Genes Dev 17: 3112-3126 (2003)). The tumors in these models exhibit the characteristic multistage histopathological progression (from precursor pancreatic intraepithelial neoplasis (PanINs) (Hansel et al., Annu Rev Genomics Hum Genet 4:237-256 (2003)) to metastatic cancer) that defines PDAC in humans, providing tractable model systems for both biological and preclinical studies (Bardeesy et al., Proc. Natl. Acad. Sci. U.S.A. 103:5947-5952 (2006)). From these mouse models, primary cell lines were derived from emerging PDAC. These early-stage cancer cell lines, in conjunction with normal pancreatic ductal cells from wild-type mice (described in Schreiber et al., Gastroenterology 127:250-260 (2004)), facilitated screening for biomarkers and imaging agents using combinatorial chemistry-based approaches (see the Examples herein).

In order to overcome these limitations, the present methods include the use of novel molecular markers and imaging probes for incipient PDAC that enable earlier detection and guide the development of interventive therapies. Described herein are the use of peptide phage display and early passage PDAC cell lines isolated from mouse models to identify peptides that distinguish both human and murine PDAC cells from normal pancreatic ductal cells in vitro. In addition to the generation of imaging agents, the binding partners of the surface proteins identified in this approach represent a snapshot of the proteome in aberrant cells and may be useful for the delineation of the underlying signal transduction pathways important to disease progression. Further, these imaging probes are contemplated to provide effective treatments for pancreatic and other cancers. The methods described herein can be used for detecting tumors and pancreatic cancer cells at any stage, including early stages, prior to spreading.

Although biomarkers were reported for PDAC cells, these markers were problematic in that they appeared to extensively overlap with other cell types, were not conjugated to nanoparticles, or were not plectin-1. Numerous attempts for identifying PDACs were described in publications, for example, in methods for detecting and diagnosing pancreatic cancer, including but not limited to determining the expression level of pancreatic associated genes that discriminate between cancerous and normal cells both in vivo and in vitro, methods of screening therapeutic agents for treating pancreatic cancer, and methods of treating pancreatic cancer, (Nakamura, et al. "Method For Diagnosing Pancreatic Cancer," United States Patent Application Number 20050260639), a method of qualifying pancreatic cancer status in a subject by measuring at least one biomarker and correlating that measurement with the cancer's status (Chan et al. "Identification Of Biomarkers For Detecting Pancreatic Cancer," United States Patent Application Number 20050095611). None of these references describe plectin-1. Further, in methods and systems for identification of abnormal cell growth, particularly the presence of pancreatic cancer or susceptibility to pancreatic cancer where an identifying candidate agent for treatment of pancreatic cancer is obtained from Affymetrix GeneChip analysis (Hruban et al. "Pancreatic Cancer Diagnosis And Therapies," United States Patent Application Number 20030180747). In this last reference, plectin-1 was identified as one of 97 genes differentially overexpressed in pancreatic cancer cells compared to normal pancreatic cells however this reference does not discuss aberrant cell membrane distribution of plectin-1, or the detection of plectin-1 with a peptide. Moreover, previous attempts at using a peptide marker for identifying Pancreatic adenocarcinoma cells were published, where synthetic peptides of Peptide tyrosine tyrosine (termed "YY" or "PYY" or Pancreatic Peptide "PP"), a 36 amino acid residue peptide amide and fragments thereof, including PYY3-36 and YPIKPEAPGEDASPEELNRYYASL-RHYLNLVTRQRY (SEQ ID NO:25), peptide YY14-36, in particular, (U.S. Pat. No. 5,574,010) showed a high specific binding to pancreatic cancer cells and delivered fluorescent dyes to cancer cells. It was contemplated but not shown, that a strategy of using biotinylated peptides to deliver avidin-dye complexes to cancer cells will allow imaging of pancreatic tumors and delivery of therapeutic agents. However, further publications describe the use of these and similar peptides for identifying neuronal cells and used for both diagnosing and treating obesity (WO/2004/056314) and treating cancer, for example, colon adenocarcinoma, pancreatic adenocarcinoma, or breast cancer. Additionally, a receptor for PYY was reported as a Y2 receptor, (for example, U.S. Pat. No. 5,574,010; U.S. Pat. No. 5,604,203; U.S. Pat. No. 5,696,093; U.S. Pat. No. 6,046,167; Gehlert et. al., Proc Soc Exp Biol Med 218:7-22 (1998); Sheikh et al. Am J Physiol, 261:701-15 (1991); Fournier et al., Mol. Pharmacol. 45:93-101 (1994); Kirby et al., J Med Chem 38:4579-4586 (1995); Rist et al., Eur. J. Biochena 247:1019-1028 (1997); Kirby et al., J Med ClzeTn 36:3802-3808 (1993); Grundemar et al., Regulatory Peptides 62:131-136 (1996); U.S. Pat. No. 5,696,093 (examples of PYY agonists), and U.S. Pat. No. 6,046,167; all of which are herein incorporated by reference in their entirety). However, none of these references disclose the use of a peptide ligand that recognized plectin-1 for identifying pancreatic cancer cells.

As described herein, phage display was used to identify peptides that distinguish mouse and human PDAC cells from normal pancreatic duct cells in vitro. The inventors subsequently conjugated 2 peptides with the highest affinities and specificities for PDACs to magnetofluorescent nanoparticles (CLIO-VT680) and demonstrate that these agents can effectively detect emerging tumors and pre-neoplastic lesions in a relevant transgenic mouse model via intravital confocal microscopy (Olympus IV100) and optical/MR imaging (OV-100, Bruker Pharmascan). Correlative histology confirmed the specific temporal localization of the PDAC targeted agents. Additionally, the peptide-binding partners identified from this approach represent a snapshot of the proteome in aberrant cells and also potential PDAC biomarkers. Using affinity chromatography, binding partners for several phage displayed peptides were identified, and their validity as biomarkers was demonstrated, in particular for Clones 27 and 15. These specific and sensitive probes are contemplated to have clinical utility in the diagnosis and management of PDAC in humans.

II. Peptide Ligands for Identifying "Accessible" Receptors in Proteomes of Pancreatic Cancer Cells Differential protein processing and/or trafficking, which can be identified using proteomic approaches, represents a potential class of biomarkers that would be missed if looking at cDNA expression data only or using whole-cell proteomics methods. For example, the binding partners of clone 27 and clone 15 identified by the methods described herein represent cancer biomarkers and may shed light on aberrant molecular pathways contributing to PDAC pathogenesis.

Clone 27 permitted the identification of membrane-localized plectin-1 as a potential new biomarker for PDAC. As described herein, plectin-1 levels are low in normal pancreatic ductal cells, but expression of plectin-1 is upregulated in PanINs and remains elevated in PDAC. Plectin-1 exhibited distinct cytoplasmic and nuclear localization in normal fibroblasts, whereas aberrant expression on the cell membrane is observed in PDAC. In some embodiments, mechanisms of protein upregulation, differential trafficking, and whether a biomarker contributes to disease progression are contemplated for additional use in biomarker diagnostics and treatments of cancer cells. Notable in this regard, recent publications illustrate that plectin-1 can be recruited to the membrane during epithelial cell transformation (Raymond et al., Mol Biol Cell 18: 4210-4221 (2007)). Altered subcellular localization of plectin-1 is also observed in the autoimmune condition, paraneoplastic pemphigus, and in the associated lymphoproliferative neoplasm, Castleman disease (Aho et al., J Invest Dermatol 113: 422-423 (1999)). Plectin-1 has a number of important roles in signal transduction, influencing Rho activity (Andra et al., Genes Dev 12: 3442-3451 (1998)), and serving as a scaffold for proteins involved in protein kinase C (PKC) (Osmanagic-Myers et al., J Biol Chem 279: 18701-18710 (2004)) and AMP-activated protein kinase signaling pathways (Gregor et al., J Cell Sci 119: 1864-1875 (2006)). Thus, plectin-1 in PDAC may have an impact on signaling pathways that regulate cell migration, polarity, and energy metabolism.

Plectin-1 Expression in the Pancreas

Plectin-1 is a high molecular weight protein (500 kDa) that links intermediate filaments to microtubules and microfilaments, in addition to anchorin the cytoskeleton the plasma and nuclear membranes (reviewed in Sonnenberg, et al., Exp Cell Res 313:2189-2203 (2007)).

As described herein, plectin-1 levels are low in normal pancreatic ductal cells but its expression is upregulated in PanINs and remains elevated in PDACs. Plectin-1 exhibited distinct cytoplasm and nuclear localization in normal fibroblasts, whereas an aberrant expression on the cell membrane is observed in PDACs. Altered subcellular localization of plectin-1 was also observed in an autoimmune condition, parancoplastic pemphigus and in the associated lymphoproliferative neoplasm, Castleman's disease (Aho et al., J Invest Dermatol 113:422-423 (1999)).

Studying the mechanisms of plectin-1 protein upregulation, differential trafficking, and contributions to disease progression are important contemplated experiments. As noted above, plectin-1 has important roles in signal transduction. Thus, plectin-1 in PDACs may have an impact on signaling pathways that regulate cell migration, polarity and energy metabolism related to carcinogenesis.

Further, publications describe significant overexpression of plectin-1 in a variety of pancreatic cancer tissues and cells compared to their non-cancerous counterparts (such as Hruban, et al. "Pancreatic Cancer Diagnosis And Therapies," United States Patent Application Number 20030180747), where methods and systems were described for identification of abnormal cell growth, particularly the presence of pancreatic cancer or susceptibility to pancreatic cancer. This reference further discloses methods for identifying candidate agents for treatment of pancreatic cancers. Affymetrix GeneChip analysis identified plectin-1 as one of 97 genes differentially overexpressed in pancreatic cancer cells compared to normal pancreatic cells. Iacobuzio-Donahue et al., Am J Pathol. 160(4):1239-1249 (2002) discloses Affymetrix GeneChip arrays to identify genes differentially expressed in resected pancreas cancer tissues and pancreas cancer cell lines as compared to normal pancreas and gastrointestinal mucosa cells. Table 1 identifies plectin-1 as one of the 97 known genes expressed at least five-fold (6.69-fold) in pancreatic cancers. Sato et al., Am J Pathol. 164(3):903-914 (2004) discloses Affymetrix GeneChip analysis of intraductal papillary mucinous neoplasms (IPMNs) of the pancreas that identifies plectin-1 as one of 673 transcripts significantly overexpressed relative to nonneoplastic pancreatic ductal epithelium. Finally, Johnson et al., Molecular Carcinogenesis 45:814-827 (2006) employs DNA array technology to identify genes differentially expressed in pancreatic tumors (11 PDACs) as compared to non-malignant pancreatic tissues (14 non-malignant bulk pancreatic duct specimens). The results listed in Table 2, of Sato et al., supra, confirmed previous findings regarding plectin-1 overexpression (4.5-fold) in PDAC tissues compared to non-cancerous tissues. Further, a potential natural ligand for plectin was identified using anti-plectin antibodies for immunoprecipitation of plectin-periplakin complexes in Boczonadi et al., Experimental Cell Research 313(16):3579-3591 (2007)). However these references do not discuss aberrant cell membrane distribution of plectin-1, or the detection of plectin-1 with a peptide or using a fluorescently labeled peptide probe (e.g., conjugated to nanoparticles) specific for plectin-1 to detect emerging PDACs.

III. The "Accessible" Proteome as a Source of Cancer Cell Biomarkers

As described herein, a phage display approach was used to screen for peptides that specifically bind to cell surface antigens on PDAC cells. These screens yielded a motif that distinguishes PDAC cells from normal pancreatic duct cells in vitro which, upon proteomic analysis, identified plectin-1 as a novel biomarker of PDAC. To assess their utility for in vivo imaging, the plectin-1 targeted peptides (PTP) were conjugated to magnetofluorescent nanoparticles. In conjunction with intravital confocal microscopy and MRI, these nanoparticles enabled detection of small PDAC and precursor lesions in engineered mouse models. The inventors developed a specific imaging probe based upon a peptide ligand, Clone 27, and discovered plectin-1 as a biomarker for pancreatic cancer cells contemplated for clinical utility in the diagnosis, management and treatment of PDAC in humans.

Phage display was used to identify peptides that distinguish mouse and human PDAC cells from normal pancreatic duct cells in vitro. The two peptides with the highest affinities and specificities were conjugated to magnetofluorescent nanoparticles (CLIO-VT680), and were demonstrated to effectively detect emerging tumors and pre-neoplastic lesions in a relevant transgenic mouse model via intravital confocal microscopy (Olympus IV100) and optical/MR imaging (OV-100, Bruker Pharmascan). Correlative histology confirmed the specific temporal localization of the PDAC targeted agents. Additionally, the peptide-binding partners identified from this approach represent a snapshot of the proteome in aberrant cells and also potential PDAC biomarkers. Using affinity chromatography, the binding partners for several peptides were identified, and their validity as biomarkers was demonstrated. These specific and sensitive probes are useful in the diagnosis and management of PDAC, e.g., in humans.

Methods for determining the sequence of identified binding molecules are also described herein. For example, when the binding molecules are produced in an expression library, encoding nucleic acids can be isolated from selected clones expressing binding molecules identified in a screen, such a ligand-target receptor binding assay. The encoding nucleic acids of the virions that bound to a target can then be sequenced using methods known to those skilled in the art.

Also described herein are methods for characterizing biomarkers that are selectively bound by a binding molecule, such as a peptide ligand. Once a binding partner (e.g., a peptide ligand) has been identified that is selective for a biomarker, the biomarker can then be isolated by, for example, affinity methods known in the art, and characterized. This characterization can be beneficial if the biomarkers used in the screen are not well characterized. Characterization of the biomarker includes such techniques as determining its apparent molecular weight by gel electrophoresis. Other methods applicable for characterizing biomarkers include, for example, high performance liquid chromatography (HPLC), mass spectrometry, or other methods that provide information about the physical, biochemical or functional properties of the biomarker, e.g., sequence and identity. Numerous methods are available for such characterization of biomarkers.

In preferred embodiments, biomarkers are derived from the cell surface of tumor cells. Cell surface molecules can be labeled, for example, with a detectable moiety such as a radioisotope or biotin or a fluorescence label. This labeling provides a source of biomarker where the only characteristic that needs to be known is that it is on the surface of a cell. As described in the Examples, cancer cell peptide ligands were prepared by labeling bacteriophage expressing cell surface peptides with FITC and used to identify binding molecules selective for the cancer cell surface polypeptides. Biomarker populations derived from other cell or subcellular compartments can similarly be used in the methods of the invention to obtain a binding partner peptide ligand that exhibits selective affinity for at least one biomarker within the initial population. Thus, the methods of the invention are applicable to a large variety of biomarker populations in which selective binding affinity is required for the therapeutic treatment or diagnosis of a disease.

The methods of the invention comprise selectively immobilizing a diverse population of binding molecules to a solid support. For selective immobilization, either an inherent characteristic of the binding molecules that comprise the population is exploited to provide selective immobilization or, alternatively, the molecules are engineered to contain a specific characteristic to be used for selective immobilization. For example, a binding partner itself may contain a hydrophobic chemical group or domain or may be fused to a hydrophobic chemical group or domain that causes the binding partner to be immobilized to a hydrophobic solid support such as plastic. In another example, the solid support can be coated with a chemical moiety or a biomolecule such that it is able to bind to and selectively immobilize only the binding molecules that make up the binding partner population. For example, the solid support can be coated with a biomolecule that selectively binds to a domain or sequence that is common to the binding molecules. The use of such biomolecules as linkers or tethers should be selected so that they do not interfere with the biomarker binding to the peptide ligands.

IV. Engineered Mouse Models of PDAC

There is a significant challenge in studying the early molecular changes in PDAC due to the typical presentation of PDAC at advanced stage and the corresponding lack of suitable tissue specimens. Therefore, the inventors elected to exploit a series of related genetically engineered mouse models of PDAC that harbor the signature gene mutations of the human disease, including Kras activation and deletion of the p53 or In k4a/Arf tumor suppressors (Bardeesy et al., Proc. Natl. Acad. Sci. U.S.A. 103:5947-5952 (2006); Aguirre et al., Genes Dev 17:3112-3126 (2003)). The tumors in these models exhibit the characteristic multistage histopathological progression (from precursor pancreatic intraepithelial neoplasis (Pan1Ns) (Hansel et al., Annu Rev Genomics Hum Genet 4:237-256 (2003)) to metastatic cancer) that defines PDAC in humans, providing tractable model systems for both biological and preclinical studies (Bardeesy et al., (2006) supra). From these mouse models, the inventors have been able to generate primary cell lines derived from emerging PDAC. These early stage cancer cell lines, in conjunction with normal pancreatic ductal cells from wild-type mice (e.g., as described in Schreiber et al., Gastroenterology 127:250-260 (2004)), facilitate screening for biomarkers and imaging agents using combinatorial chemistry based approaches.

Genetically engineered mouse models of human cancers effectively recapitulate many of the molecular, biological, and clinical features of the human disease (Bardeesy et al., (2006) supra; Aguirre et al., (2003) supra).

Recent genomic studies of mouse and human cancers have established that cross-species in vivo analysis can serve as an effective filter in identifying recurrent chromosomal alterations associated with metastatic potential of melanoma and lymphoma-prone mice (Kim et al., Cell 125:1269-1281 (2006); Maser et al., Nature 447:966-971 (2007)). Using such an approach a 15-mer binding peptide ligand for identifying human prostate cancer cells was obtained by in vivo screening (Newton et al., Neoplasia 8:772-780 (2006)). Specifically, Newton describes identifying a phage clone displaying a 15 amino acid peptide, where the phage clone was labeled with the nearinfrared fluorophore (NIRF) AlexaFluor 680 (AF680), injected into a mouse at $10^9$ TU/ml (transducing/transfection units) of phage, and used for optical imaging of human prostate carcinoma in a mouse.

Studies described herein show the utility of mouse-human cancer models developed further for providing cancer cells at specific stages of development. Moreover phage clone screening methods were modified and extended to the development of assays for phage displaying smaller 7-mer peptides and use of such phage for sequencing and isolation of peptide ligands binding to molecules expressed by cancer cells at specific stages. These phage displaying 7-mer peptides and phage derived isolated 7-mer peptide ligands were used as molecularly targeted imaging agents while corresponding binding partners were identified and evaluated as biomarkers for pancreatic ductal adenocarcinoma.

Using these extended mouse models and phage displayed peptide binding screening methods, the inventors identified conserved biomarkers of early disease in screens that took advantage of mouse cell lines derived from early stages of cancer development and primary pancreatic ductal cells. Furthermore, the known kinetics of tumor progression of these mouse models facilitated testing of the imaging probes at defined stages of tumorigenesis. The approaches described herein are contemplated to be broadly applicable to the discovery of cancer biomarkers predictive of disease stage, prognosis, and the presence of specific genetic alterations associated with cancer cell development and prognosis.

V. Nanoparticle Based Imaging Labels and Diagnostic Methods for PDAC

Noninvasive imaging has particular applications in high risk groups, for example, hereditary PDAC kindreds and new-onset diabetes patients, who are candidates for screening for pancreatic cancer. Despite the increased cancer risk in these individuals, the incidence of actual pancreatic cancer is estimated to be only about 0.4%-0.6% (Chari, Semin Oncol 34: 284-294 (2007)), hence prophylactic surgery, which is associated with substantial morbidity and mortality, is not typically carried out. Traditional imaging methods such as CT scan or MRI often do not detect PDAC lesions until they have reached a size at which many tumors have already metastasized, thus rendering surgery ineffective. There is consequently a considerable need for a new imaging modality that would accurately identify the presence of PDAC at an earlier point in its development when surgery is effective.

Other settings for noninvasive imaging of incipient cancers include patients with cystic neoplasms, intraductal papillary mucinous neoplasms (IPMN) and mucinous cystic neoplasms (MCN). Thus in some embodiments, the inventors contemplate identifying peptide probes for biomarkers of incipient cancer cells. These tumors are often benign, however a subset of them progress to PDAC. Thus in some embodiments, the inventors contemplate methods for identifying and using peptide probes for biomarkers of neoplastic cells progressing to PDACs. New approaches using more accurate imaging molecules in postsurgical screening for recurrence and screening prior to surgery to determine exact tumor extension more accurately are contemplated. The new imaging molecules provided herein would be clinically valuable in differential diagnosis, i.e., patients presenting with pancreatitis, jaundice, or upper abdominal pain. Further, in screening of high-risk groups, the inventor contemplate an imaging molecule for distinguishing low-grade PanINs, which are present in many healthy individuals, from high-grade PanINs and carcinoma in situ. Probes are contemplated that would recognize lesions of PanIN-3 and higher since these are believed to have very high potential for progressing to invasive PDAC. Embodiments comprising translational studies are contemplated for conducting in patients undergoing resection because the rapid homing of the molecules described herein to tumors and subsequent clearance from the body makes this a technically feasible method.

In some embodiments, the peptide ligands described herein are linked to nanoparticle based imaging labels. These nanoparticles were developed and used for imaging cancer cells, such as the numerous types of magnetic nanoparticles and their magnetofluorescent analogues (see, e.g., Weissleder et al., Nat. Biotechnol., 19:316-317 (2001); McCarthy et al., Nanomedicine, 2:153-167 (2007); Hogemann et al., Bioconjug. Chem., 11:941-946 (2000), and Josephson et al., Bioconjug. Chem., 10:186-191 (1999)) which are contemplated for use with isolated peptide ligands and phage displayed peptides. Multimodal nanoparticles are known that incorporate both magnetic and fluorescent molecules within the same molecule (e.g., as described herein, i.e., PTP-NP) and used for fluorescent microscopy (which detects the fluorescent part of this very small particle) and MRI (which detects its magnetic portion). In some embodiments, the imaging probes/ligands described herein include optical imaging probes such as NanoSPARKS™ (VisEn Medical) and the like.

In some embodiments, the particles are conjugated to a fluorescent moiety, e.g., as described in U.S. Pat. No. 5,492,814; Hogemann et al., Bioconjug. Chem., 11:941-946 (2000).

The particles can be provided in any suitable form, e.g., lyophilized or in a liquid, e.g., a sterile carrier that is suitable for administration in vivo, e.g., sterile saline. Lyophilized particles can be reconstituted, e.g., in normal sterile saline, or in liquid carrier. In some embodiments, the methods use Combidex® (ferumoxtran-10), a molecular imaging agent consisting of iron oxide nanoparticles, available from Advanced Magnetics, Inc., Cambridge, Mass.

The multimodal nanoparticle imaging probes described herein home to neoplasms while showing no appreciable colocalization with adjacent areas or acinarductal metaplasia. This high level of specificity is expected to reduce false positives in diagnostic tests. Further, these new imaging probes bound to PanINs as well as to advanced cancer cells. The capacity to detect such premalignant lesions enable the development of new approaches in the management of this disease. Although liver and kidney uptake is high, the tomographic imaging techniques that would be used with this probe (e.g., MRI, single photon emission computed tomography (SPECT)/CT, optical, etc.) would allow the resolution of the pancreas in the context of both organs, allowing differentiation therebetween.

The contrast agents are administered to the subject, e.g., by intravenous, intraarterial, subcutaneous, intramuscular, intraparenchymal, intracavity, topical, ocular, oral or rectal administration, with intravenous injection being preferred.

In addition to the development of novel molecularly targeted imaging agents, phage displayed peptide screening for biding to molecules expressed by cancer cell and modified immunoprecipitation permitted the identification of membrane-localized plectin-1 as a new specific biomarker for PDAC. Significantly, differential protein processing and/or trafficking of plectin-1, identified using proteomic approaches, represents a potential class of biomarkers which is missed when merely evaluating cDNA expression data only or using whole-cell proteomics methods. In particular, although overexpression of plectin-1 was observed by gene chip analysis, it was one of 97 overexpressed genes and thus its relationship or use as a cancer cell biomarker was not known (see Iacobuzio-Donahue et al., Am J Pathol. 160: 1239-1249 (2002); and United States Patent Application Publication Number 20030180747). The binding partners of additional clones identified herein from screening methods represent additional biomarkers contemplated for use in diagnostic methods and treatments in addition to shedding light on aberrant molecular pathways contributing to PDAC pathogenesis.

Thus the peptide ligands described herein can include one or more detectable moieties linked to a plectin-1 binding moiety that binds specifically to plectin-1, e.g., a peptide consisting essentially of SEQ ID NO:1, 2, or 4-8. The detectable moiety can be or include a fluorophore, e.g., a near infrared fluorophore (NIRF). A number of NIRFs useful in the methods and compositions described herein are known in the art, e.g., including Cy5.5, Cy5 and Cy7 (Amersham, Arlington Hts., Ill.; IRD41 and TRD700 (LI-COR, Lincoln, Nebr.); NIR-1, (Dejindo, Kumamoto, Japan); LaJolla Blue (Diatron, Miami, Fla.); indocyanine green (ICG) and its analogs (Licha et al., 1996, SPIE 2927:192-198; Ito et al., U.S. Pat. No. 5,968,479); indotricarbocyanine (ITC; WO 98/47538); and chelated lanthanide compounds. Fluorescent lanthanide metals include europium and terbium. Fluorescence properties of lanthanides are described in Lackowicz, 1999, Principles of Fluorescence Spectroscopy, 2.sup.nd Ed., Kluwar Academic, New York. The fluorophores can be covalently linked to the plectin-1 binding moiety, or to a nanoparticle, e.g., via a fluorochrome attachment moiety, backbone, or spacer using any suitable reactive group on the fluorochrome and a compatible functional group on the fluorochrome attachment moiety, backbone, or spacer. For example, a carboxyl group (or activated ester) on a fluorochrome can be used to form an amide linkage with a primary amine such as the epsilon-amino group of the lysyl side chain on polylysine. Alternatively or in addition, the fluorophores can be linked directly to the backbone or linked to the backbone through nonbiodegradable spacers. See, e.g., US P.G. Pub. 20060275775.

The peptide ligands can be linked to the detectable moieties directly, e.g., as a fusion protein with protein or peptide detectable moieties (with or without an optional linking sequence, e.g., a flexible linker sequence) or via a chemical coupling moiety. A number of such coupling moieties are known in the art, e.g., a peptide linker or a chemical linker, e.g., as described in International Patent Application Publication No. WO 2009/036092.

VI. Ligands as a Targeting Moiety to Deliver Therapeutic Payloads

Ligand compositions, such as peptide ligands, used as therapeutics have advantages over other types of therapeutics, such as having a readily diffusible capability, low immunogenicity, and high specificity for target cells, in addition to flexibility in engineering novel additional elements, such as adding specific types of payloads, adding membrane permeabilizing factors, and the like. Thus, phage displaying peptide ligands and isolated peptide ligands as described herein are contemplated for use as a targeting moiety for selective delivery of therapeutic payloads, such as a radionuclide, cytokine, chemical drug, chemotherapy drug, and a therapeutic gene, to cancer cells. For the purposes of the present inventions, a "therapeutic payload" or "therapeutic cargo" includes a "therapeutic agent" and is intended to include any compound intended for extracellular or intracellular delivery to reduce the number of cancer cells or slow the growth of cancer cells or reduce the metastasis of cancer cells in a patient. Examples of types of payloads are drugs, small molecules, proteins, peptides, oligonucleotides, RNA and DNA, in other words any payload for reducing cancer in a patient.

A peptide ligand as described herein can be attached to a toxin, such as a diphtheria toxin (DTA) (for example, see, U.S. Pat. No. 5,827,934 for DT fragments, and an exemplary fusion protein $DAB_{389}EGF$ in Mishra, et al., 2003, Expert Opinion on Biological Therapy 3:1173-1180).

A drug attached to a peptide of the present invention can also include agents that are derived from, or that beneficially modulate host biological processes, such as interferons, tumor growth factors, tumor necrosis factors, growth factors such as GM-CSF and G-CSF and interleukins, for example, interleukin-2, interleukin-6, interleukin-7 and interleukin-12, and the like. A drug attached to a peptide of the present invention may comprise an agent which damages DNA and/or prevent cells from multiplying, such as genotoxins. A genotoxin includes but is not limited to alkylating agents, antimetabolites, DNA cutters, DNA binders, topoisomerase poisons and spindle poisons. Examples of alkylating agents are lomustine, carmustine, streptozocin, mechlorethamine, melphalan, uracil nitrogen mustard, chlorambucil, cyclosphamide, iphosphamide, cisplatin, carboplatin, mitomycin, thiotepa, dacarbazin, procarbazine, hexamethyl melamine, triethylene melamine, busulfan, pipobroman, mitotane and other platine derivatives.

The peptide ligand as described herein can be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g., via a viral coat protein), or mixtures thereof. The therapeutic agent can be an intracellularly active drug or other agent, such as short-range radiation emitters, including, for example, short-range, high-energy α-emitters, as described herein. In some embodiments, the peptide ligand can be coupled to a molecule of plant or bacterial origin (or derivative thereof), e.g., a maytansinoid (e.g., maytansinol or the DM1 maytansinoid). DM1 is a sulfhydryl-containing derivative of maytansine that can be linked to the peptide, e.g., via a disulfide linker that releases DM1 when inside target cells. The disulfide linkers display greater stability in storage and in serum than other linkers. Maytansine is a cytotoxic agent that effects cell killing by preventing the formation of microtubules and depolymerization of extant microtubules. It is 100- to 1000-fold more cytotoxic than anticancer agents such as doxorubicin, methotrexate, and vinca alkyloid, which are currently in clinical use. Alternatively, the peptide ligand as described herein can be coupled to a taxane, a calicheamicin, a proteosome inhibitor, or a topoisomerase inhibitor. [(1R)-3-methyl-1-[[(2S)-1-oxo-3-phenyl-2-[(3-mercaptoacetyl) amino]propyl]amino]butyl] Boronic acid is a suitable proteosome inhibitor. N,N'-bis[2-(9-methylphenazine-1-carboxamido)ethyl]-1,2-ethanediamine is a suitable topoisomerase inhibitor.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin. In some embodiments, the peptide ligand is conjugated to maytansinoids, e.g., maytansinol (see U.S. Pat. No. 5,208,020), CC-1065 (see U.S. Pat. Nos. 5,475,092, 5,585,499, 5,846, 545). Procedures for preparing enzymatically active polypeptides of the immunotoxins are described in WO84/03508 and WO85/03508, which are hereby incorporated by reference. Examples of cytotoxic moieties that can be conjugated to the antibodies include adriamycin, chlorambucil, daunomycin, methotrexate, neocarzinostatin, and platinum.

To kill or ablate cancerous cells, a peptide ligand can be conjugated with a prodrug that is activated only when in close proximity with a prodrug activator. The prodrug activator is conjugated with a second peptide ligand, e.g., a second peptide ligand according to the present invention, preferably one that binds to a non-competing site on the same receptor (e.g., plectin-1) or cell. Whether two peptide ligand bind to competing or non-competing binding sites can be determined by conventional competitive binding assays. Drug-prodrug pairs suitable for use are known in the art, see, e.g., in Blakely et al., Cancer Research 56:3287-3292 (1996).

Alternatively, the peptide ligand can be coupled to high energy radiation emitters, for example, a radioisotope, such as $^{131}I$, a γ-emitter, which, when localized at the tumor site, results in a killing of several cell diameters. See, e.g., Order, "Analysis, Results, and Future Prospective of the Therapeutic Use of Radiolabeled Antibody in Cancer Therapy", in *Monoclonal Antibodies for Cancer Detection and Therapy*, R. W. Baldwin et al. (eds.), pp 303-316 (Academic Press 1985). Other suitable radioisotopes include α-emitters, such as $^{212}Bi$, $^{213}Bi$, and $^{211}At$, and β-emitters, such as $^{186}Re$ and $^{90}Y$. $Lu^{117}$ may also be used as both an imaging and cytotoxic agent.

Radioimmunotherapy (RIT) using peptide ligand labeled with $^{131}I$, $^{90}Y$, and $^{177}Lu$ is under intense clinical investigation. There are significant differences in the physical characteristics of these three nuclides and as a result, the choice of radionuclide can be important in order to deliver maximum radiation dose to the tumor. The higher beta energy particles of $^{90}Y$ may be good for bulky tumors, but it may not be necessary for small tumors and especially bone metastases, (e.g. those common to prostate cancer). The relatively low energy beta particles of $^{131}I$ are ideal, but in vivo dehalogenation of radioiodinated molecules is a major disadvantage for internalizing peptide ligands. In contrast, $^{177}Lu$ has low energy beta particle with only 0.2-0.3 mm range and delivers much lower radiation dose to bone marrow compared to $^{90}Y$. In addition, due to longer physical half-life (compared to $^{90}Y$), the tumor residence times are higher. As a result, higher activities (more mCi amounts) of $^{177}Lu$ labeled agents can be administered with comparatively less radiation dose to marrow. There have been several clinical studies investigating the use of $^{177}Lu$ labeled antibodies in the treatment of various cancers (see, e.g., Mulligan et al., Clin Cancer Res. 1: 1447-1454 (1995); Meredith et al., J Nucl Med 37:1491-1496 (1996); Alvarez et al., Gynecologic Oncology 65: 94-101 (1997)).

The peptide ligands of the invention can also be conjugated or fused to viral surface proteins present on viral particles. For example, a peptide ligand could be fused (e.g., to form a fusion protein) to a viral surface protein. Alternatively, a peptide ligand could be chemically conjugated (e.g., via a chemical linker) to a viral surface protein. Preferably, the virus is one that fuses with endocytic membranes, e.g., an influenza virus, such that the virus is internalized along with the peptide ligand and thereby cancer cells. The virus can be genetically engineered as a cellular toxin. For example, the virus could express or induce the expression of genes that are toxic to cells, e.g., cell death promoting genes. Preferably, such viruses would be incapable of viral replication.

The peptide ligands can be linked to the therapeutic agent directly, e.g., as a fusion protein with protein or peptide toxins (with or without an optional linking sequence, e.g., a flexible linker sequence) or via a chemical coupling moiety. A number of such coupling moieties are known in the art, e.g., a peptide linker or a chemical linker, e.g., as described in International Patent Application Publication No. WO 2009/036092.

The peptide ligands (e.g., linked to an imaging moiety or a therapeutic agent) described herein can be incorporated into pharmaceutical compositions. Such compositions typically include the compound (i.e., as an active agent) and a pharmaceutically acceptable carrier. As used herein, "pharmaceutically acceptable carriers" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

For administration by inhalation, the compounds are typically delivered in the form of an aerosol spray from pressured container or dispenser which contains a suitable propellant, e.g., a gas such as carbon dioxide, or a nebulizer. Such methods include those described in U.S. Pat. No. 6,468,798.

The therapeutic compounds can also be prepared in the form of suppositories (e.g., with conventional suppository bases such as cocoa butter and other glycerides) or retention enemas for rectal delivery.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Concentration ranges of a drug in vitro in which peptide ligand targeting may enhance the ability of a drug to selectively kill cancer cells depend, usually, on the drug used. For example, genotoxin is used usually at a concentration in vitro between 0.1 to 100, µM, preferably between 0.15 to 30 µM/kg.

Therapeutic compositions of peptide ligands that deliver drugs to cancer cells may increase the sensitivity of cancer cells to additional anti-cancer treatments, for example, peptide ligands conjugated to paclitaxel, in the range of 150 mg/m$^2$ of body surface, increases cancer cell sensitivity to certain drugs, while cisplatin in the range of 20 mg/m$^2$/day increases cancer cell sensitivity to radiation.

Peptide ligands that bind to the external surface of cells may comprise a "membrane fusion component" intended to include a domain or molecule that facilitates transport of a payload into a cell. The membrane fusion component may contain a membrane permeant motif. The membrane fusion component can be isolated from a naturally occurring protein, or may be a synthetic molecule based in whole or in part on a naturally occurring domain, for example, human immunodeficiency virus type 1 (HIV-1) glycoprotein-120 (GP120), human immunodeficiency virus type 1 (HIV-1) glycoprotein-42 (GP41), human immunodeficiency virus (HIV-1) (transactivator of transcription (Tat)) protein), human parainfluenza virus, hemagglutinin (HA) of influenza virus (termed HA2), Ebola virus transmembrane fusion sequence, helical coil-coils, alpha-hemolysin, glyceraldehyde-3-phosphate dehydrogenase (GAPDH), Melittin (active component of bee venom), a hydrophobic segment, a synthetic membrane transporter, and the like. Suitable membrane fusion components are known in the art, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49.

The pharmaceutical compositions can be included in a container, pack, or dispenser together with instructions for administration.

VIII. Antibodies

The present invention provides isolated antibodies (e.g., polyclonal or monoclonal) having affinity for a cancer biomarker. In some embodiments, the cancer comprises pancreatic cancer. In other embodiments, the cancer includes, but is not limited to, lung cancer, breast cancer, prostate cancer, skin cancer, brain cancer, liver cancer, bone cancer, or kidney cancer. In some embodiments, the present invention provides monoclonal antibodies that specifically bind to an isolated polypeptide comprised of at least five amino acid residues of a plectin biomarker (e.g., SEQ ID NO:1). These antibodies find use in the imaging methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 (1975)). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

VIII. Designing Mimetics

Compounds mimicking the necessary conformation for recognition and binding to a biomarker, such as plectin-1, are contemplated as within the scope of this invention. For example, In some embodiments, mimetics of SEQ ID NOs: 1-8 and all of the peptides of the present invention are contemplated. A variety of designs for such mimetics are possible. U.S. Pat. No. 5,192,746 to Lobl, et al., U.S. Pat. No. 5,169,862 to Burke, Jr., et al., U.S. Pat. No. 5,539,085 to Bischoff, et al., U.S. Pat. No. 5,576,423 to Aversa, et al., U.S. Pat. No. 5,051,448 to Shashoua, and U.S. Pat. No. 5,559,103 to Gaeta, et al., all hereby incorporated by reference, describe multiple methods for creating such compounds.

Synthesis of nonpeptide compounds that mimic peptide sequences is also known in the art. Eldred, et al, (J. Med. Chem. 37:3882 (1994)) describe nonpeptide antagonists that mimic the Arg-Gly-Asp sequence. Likewise, Ku, et al, (J. Med. Chem. 38:9 (1995)) give further elucidation of the synthesis of a series of such compounds. Such nonpeptide compounds that mimic, for example, KTLLPTP [SEQ ID NO: 1] peptides (or, of any one or more of the polypeptides of the present invention) are specifically contemplated by the present invention.

The present invention also contemplates synthetic mimicking compounds that are multimeric compounds that repeat relevant peptide sequences. As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the α-amino group of the component containing the activated carboxyl group can be blocked with a tertbutyloxycarbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In some embodiments, the mimetics of the present invention are peptides having sequence homology to the above-described plectin protein ligands. One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. See, e.g., Pearson and Lipman, Proc. Natl. Acad. Sci. (USA) 85:2444-2448 (1988); Lipman and Pearson, Science 227:1435-1441 (1985). In the present invention, synthetic polypeptides useful in tumor therapy and in blocking invasion are those peptides with statistically significant sequence homology and similarity (Z value of Lipman and Pearson algorithm in Monte Carlo analysis exceeding 6).

The present invention also contemplates peptide sequence derivatives of SEQ ID NOS: 1-8 (or any one or more of the polypeptides sequences of the present invention) identified by means of an amino acid pairing technique. See, e.g., Root-Bernstein, J. Theor. Biol. 94:885-859 (1982); and Stefanowicz et al., Letters in Peptide Science 5:329-331 (1998). To identify peptide sequence derivates useful in the present invention, the methodology is adapted to identify sequences that are in some wise complementary to seprase, but that specifically inhibit seprase activity without, at the same time, themselves potentiating the migration of cells.

The peptide ligands described herein can be protease resistant and can include one or more types of protecting groups such as an acyl group, an amide group, a benzyl or benzoyl group, or a polyethylene glycol. More specifically, a peptide, including the modified peptides described above, can be N-terminally acetylated and/or C-terminally amidated.

Where non-naturally occurring or modified amino acid residues are included they can be selected from the following or many others available in the art: 4-hydroxyproline, gamma-carboxyglutamic acid, o-phosphoserine, o-phosphotyrosine, or delta-hydroxylysine. Other examples include naphthylalanine, which can be substituted for trytophan to facilitate synthesis, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl. Peptides having non-naturally occurring amino acid residues may be referred to as synthetic peptides and constitute one type of variant as described herein. Other variants include peptides in which a naturally occurring side chain of an amino acid residue (in either the L- or D-form) is replaced with a non-naturally occurring side chain.

In some embodiments, the peptides can have three extra amino acids (Met-Gly-Ser) at either terminus (or both) (e.g., at the N-terminus) and seven to eight extra amino acids (e.g., Thr-Ser-His-His-His-His-His-His-Cys (SEQ ID NO:26)) at either terminus (or both) (e.g., at the C-terminus).

In some embodiments, the peptides can be PEGylated by methods known in the art.

For guidance on peptide modification by reduction/alkylation and/or acylation, one can consult Tarr, *Methods of Protein Microcharacterization*, Silver ed., Humana Press, Clifton N.J. (1986) 155-194; for guidance on chemical coupling to an appropriate carrier, one can consult Mishell and Shiigi, eds, *Selected Methods in Cellular Immunology*, W H Freeman, San Francisco, Calif. (1980) and U.S. Pat. No. 4,939,239; and for guidance on mild formalin treatment, one can consult Marsh, Int. Arch. Allergy Appl. Immunol., (1971) 41:199-215.

Peptidomimetics of the peptide ligands can also be used. Peptide ligands disclosed herein can be modified according to methods known in the art for producing peptidomimetics. See, e.g., Kazmierski, W. M., ed., *Peptidomimetics Protocols*, Human Press (Totowa N.J. 1998); Goodman et al., eds., *Houben-Weyl Methods of Organic Chemistry: Synthesis of Peptides and Peptidomimetics*, Thiele Verlag (New York 2003); and Mayo et al., J. Biol. Chem., 278:45746, (2003). In some cases, these modified peptidomimetic versions of the peptides and fragments disclosed herein exhibit enhanced stability in vivo, relative to the non-peptidomimetic peptides. Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences. Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, i.e., an artificial amino acid analog. Artificial amino acid analogs include β-amino acids, β-substituted β-amino acids ("β$^3$-amino acids"), phosphorous analogs of amino acids, such as α-amino phosphonic acids and α-amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules. These sequences can be modified, e.g., by biotinylation of the amino terminus and amidation of the carboxy terminus.

Any of the peptides described herein, including the variant forms described herein, can further include a heterologous polypeptide. The heterologous polypeptide can be a polypeptide that increases the circulating half-life of the peptide to which it is attached (e.g., fused, as in a fusion protein). The heterologous polypeptide can be an albumin (e.g., a human serum albumin or a portion thereof) or a portion of an immunoglobulin (e.g., the Fc region of an IgG). The heterologous polypeptide can be a mitochondrial-penetrating moiety.

Compounds mimicking the necessary conformation of the peptides described herein are contemplated as within the scope of this invention. A variety of designs for such mimetics are possible. U.S. Pat. No. 5,192,746; U.S. Pat. No. 5,169,862; U.S. Pat. No. 5,539,085; U.S. Pat. No. 5,576,423; U.S. Pat. No. 5,051,448; and U.S. Pat. No. 5,559,103, all hereby incorporated by reference, describe multiple methods for creating such compounds. Non-peptidic compounds that mimic peptide sequences are known in the art (see, e.g., Meli et al. J. Med. Chem., 49:7721-7730 (2006), describing methods of identifying nonpeptide small molecule mimics of shepherdin). Synthesis of non-peptide compounds that mimic peptide sequences is also known in the art (see, e.g., Eldred et al. J. Med. Chem., 37:3882, (1994); Ku et al. J. Med. Chem., 38:9, (1995); Meli et al. J. Med. Chem., 49:7721-7730 (2006)). Such nonpeptide compounds that mimic the sequences described herein that bind plectin-1 are specifically contemplated by the present invention.

The present invention also contemplates synthetic mimicking compounds. As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the (α-amino group of the component containing the activated carboxyl group can be blocked with a tertbutyloxycarbonyl group. This protecting group can be subsequently removed by exposing the peptide to dilute acid, which leaves peptide bonds intact. With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In some embodiments, the mimetics of the present invention are peptides having sequence homology to the herein-described chaperone inhibitor peptides. These mimetics include, but are not limited to, peptides in which L-amino acids are replaced by their D-isomers. One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant (Pearson and Lipman, Proc. Natl. Acad. Sci. (USA), 85:2444-2448, (1988); Lipman and Pearson, Science, 227:1435-1441, (1985). More generally, the peptide ligands described herein and the mimetics described above can be synthesized using any known methods, including tea-bag methodology or solid phase peptide synthesis procedures described by Merrifield et al., Biochemistry, 21:5020-5031, (1982); Houghten Wellings, Proc. Natl. Acad. Sci. (USA), 82:5131-5135, (1985); Atherton, Methods in Enzymology, 289:44-66, (1997), or Guy and Fields, Methods in Enzymology, 289:67-83, (1997), or using a commercially available automated synthesizer.

IX. Small Molecule Drugs

In some embodiments, the present invention provides drugs (e.g., small molecule drugs) that reduce or eliminate cancer by binding to a cancer biomarker (e.g., plectin). In some embodiments, small molecule drugs are identified using the drug screening methods described herein. In preferred embodiments, the small molecule drugs of the present invention result in the death of cancer, but not normal cells. In some embodiments, small molecule drugs are identified using the drug screens described herein (e.g., in Section III above).

In some embodiments, the present invention provides drug screening assays (e.g., to screen for anticancer drugs). The present invention is not limited to a particular mechanism. Indeed, and understanding of the mechanism is not necessary to practice the present invention. The present invention provides drug screening methods for identifying compounds that bind to a cancer biomarker expressed on a cell surface membrane (e.g., a tumor tissue). The present invention further provides methods of identifying chemotherapeutic agents that are active in plectin-1 expressing cancers. In some embodiments, candidate compounds such as small molecules are directed against plectin-1.

In some embodiments, the invention contemplates a method for identifying an effective nonpeptide small-molecule inhibitor that blocks/inhibits/prevents/disrupts a cancer biomarker (e.g., plectin). These molecules may be discovered using any one of several high-throughput screening methods. See, e.g., Stockwell, Nature 432:846-854 (2004); Kay et al., Mol. Diversity 1:139-140 (1996); Pfleger et al., Cell Signaling 18:1664-1670 (2006); Jung et al., Proteomics 5: 4427-4431 (2005); Nieuwenhuijsen et al., J. Biomol. Screen 8:676-684 (2003); and Berg, Angew. Chem. Int. Ed. Engl. 42:2462-2481 (2003).

EXAMPLES

The following examples serve to illustrate certain embodiments and aspects of the present invention and are not to be construed as liming the scope thereof.

In the experimental disclosures which follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); pg (picograms); L and l (liters); ml (milliliters); μl (microliters); cm (centimeters); mm (millimeters); μm (micrometers); nm (nanometers); U (units); min (minute); s and sec (second); k (kilometer); deg (degree); ° C. (degrees Centigrade/Celsius), colony-forming units (cfu), plaque forming units (PFU), optical density (OD; o.d.), internal diameter (i.d.), and polymerase chain reaction (PCR).

Example 1

This example describes exemplary materials and methods for assays used during the development of the present inventions.
Cell Culture Primary mouse pancreatic ductal cells from wildtype mice were isolated and cultivated using published methods (Schreiber, et al., (2004) Gastroenterology 127:250-260). Early passage PDAC cell lines were isolated from tumors arising in Pdxl-Cre LSL-KrasG12D p53$^{L/L}$ mice (designated Kras/p53$^{L/L}$) (Bardeesy, et al. (2006) Proc. Natl. Acad. Sci. U.S.A. 103:5947-5952). For the phage display experiments, PDAC cells were first grown in the primary duct cell media (F12 medium supplemented with 5 mg/mL D-glucose (Sigma), 0.1 mg/mL soybean trypsin inhibitor type I (Sigma), 5 mL/L insulin-transferrin-selenium (ITS+; BD Biosciences, Palo Alto, Calif.), 25 μg/mL bovine pituitary extract (BD Biosciences), 20 ng/mL epidermal growth factor (BD Biosciences), 5 nmol/L 3,3',5-triiodo-L-thyronine (Sigma), 1 μmol/L dexamethasone (Sigma), 100 ng/mL cholera toxin (Sigma), 10 mmol/L nicotinamide (Sigma), 5% Nu-serum IV culture supplement (Collaborative Biomedical Products), and antibiotics (penicillin G 100 U/mL, streptomycin 100 μg/mL, amphotericin B 0.25 μg/mL; Gibco-BRL, Grand Island, N.Y.). Human PDAC cell lines (MNA, 8988, SW1990, MIA-PaCa-2, ASPC) were purchased from ATCC and cultured according to established protocols. NIH-3T3 cells (mouse fibroblasts) are purchased from ATCC. Murine heart endothelial cells (MHEC) were isolated from mice according to previously published protocols (Allport et al., J Leukoc Biol 71:821-828 (2002)) and used after the second subculture. Human umbilical vein endothelial cells (HUVECs) were purchased from Clonetics and cultured according to the manufacturer's protocol.
Mouse Cohorts Imaging studies were performed in Pdxl-Cre LSL-KrasG12Dp53$^{L/+}$ (Kras/p53$^{L/+}$), Pdxl-Cre LSL-KrasG12D p16$^{+/-}$ (Kras/p16$^{+/-}$), Pdxl-Cre LSL-KrasG12D (Kras), and wild type mice (Bardeesy et al., Proc. Natl. Acad. Sci. U.S.A. 103:5947-5952 (2006)). Breeding, genotyping and analysis were performed as previously published (Bardeesy, et al., Proc. Natl. Acad. Sci. U.S.A. 103:5947-5952 (2006); and Aguirre et al., Genes Dev 17:3112-3126 (2003)). Mice were housed in a pathogen-free environment at the Massachusetts General Hospital (MGH). The mice were handled in strict accord with good animal practice as defined by the Office of Laboratory Animal Welfare, and all animal work was done with Institutional Animal Care and Use Committee approval.
Phage Selection Phage positive selection and negative selection were achieved by incubating mouse PDAC cells isolated from the Kras/p53 mouse with phage (1×10$^{11}$ PFU), which displayed a randomized linear 7 amino acid peptide library (phD7, New England Biolabs, Beverly, Mass.) for 1 hour at 37° C. to allow time for phage to be internalized into the PDAC cells. Screening for cell-internalizing phage affords a type of signal amplification by concentrating the imaging agent inside the cell with the additional benefit that the agent is not subject to $k_{off}$ (off rate), further increasing the effective affinity (Kelly et al., Circ Res 96: 327-336 (2005)). To remove unbound phage and non-specific binding phage, the cells were first washed with DPBS supplemented with 1% BSA and 0.05% Tween-20. Cell surface bound phage were removed by washing with 0.1 M glycine (pH 2) for 8 minutes. Following a second glycine wash, the internalized phage were recovered by lysing the cells with 0.1% triethanolamine (Sigma, St. Louis, Mo.) in PBS (pH 7.6) for 5 min at room temperature. The internalized phage pool was neutralized with 100 μL of 0.5 M Tris-HCl (pH 7). The counter-selection was done by incubating the internalized phage pool with normal pancreatic cells for three 30 minute cycles to effectively subtract all clones that bind to both normal pancreatic ductal cells and PDAC (Kelly et al., Neoplasia 5: 437-444 (2003)). The internalized phage were amplified in *Escherichia coli*, titered, and subjected to three additional rounds for a total of 4 rounds of positive selection on the PDAC cells. From this selection, 30 clones were selected for sequencing and analyzed by ELISA (see below).
Enzyme-Linked ImmunoSorbent Assay (ELISA) and Multidimensional Analysis ELISA and multidimensional analysis were used to facilitate choosing appropriate clones for further study (Kelly et al., Mol Imaging 5:24-30 (2006)). Specifically, Pancreatic ductal adenocarcinoma (PDAC) and normal cells (noncancerous) were grown to 100% confluence in a 96-well plate and incubated sequentially at 37° C. with 30 phage clones (10$^7$ and 10$^{10}$ PFU, 1 h) in triplicate, washed with PBS containing 0.1% Tween-20, incubated with biotinylated anti-M13 antibody (1:40, 1 h), detected with streptavidin-Horseradish peroxidase (HRP) (1:500), developed with tetramethyl-benzidine and absorbance at 650 was determined (Emax, Molecular Devices).

Raw plate-reader outputs corresponding to PDAC or normal ductal cells were unpivoted to afford a denormalized table of values, and each well position was then associated with similar arrays of metadata labels. Values from each well were background subtracted using the median value of mock-treatment wells (wild-type phage) from each assay plate. Background-subtracted (Bsub) values for mock-treatment wells were accumulated across multiple assay plates to afford two mocktreatment distributions reflecting assay noise, one corresponding to PDAC cells and one corresponding to normal ductal cells, and trimmed according to Chauvenet's criterion as previously described (Kelly et al., Circ Res 96: 327-336 (2005)). These mock-treatment distributions were used to normalize independently each value corresponding to a phage-treated well, affording Z-normalized (Znorm) values for each well. All data formatting, manipulation, and normalization were implemented using Pipeline Pilot (Scitegic) and data visualizations (heat map) were prepared using DecisionSite (Spotfire).

Phage Labeling

For in vitro and in vivo validation experiments, phage were fluorochrome-labeled as previously described (Kelly et al., Neoplasia 8:1011-1018 (2006)). Briefly, approximately 1×10$^{12}$ PFU of phage was suspended in 100 μL of 0.3 M NaHCO$_3$ (pH 8.6) then depending upon the experiment the NaHCO$_3$ solution contained one of the following dyes: 1 mg/mL of fluorochrome-hydrosuccinimide ester (conjugated to either Cy5.5 or AF750), 0.25 mg/mL of FITC, 0.25 mg/mL of RITC (rhodamine isothiocyanate). The labeling reaction was allowed to continue in the dark at room temperature (RT) with gentle agitation. After 1 hour, the reaction mixture was diluted to 1 mL in DPBS and the labeled-phage was purified by PEG precipitation (3×). The fluorochrome-labeled phage was resuspended in 200 μL DPBS. Plaque-forming units were determined by titer analysis and the concentration of the fluorochrome was determined spectrophotometrically (Varian Cary 11, Varian, Palo Alto, C.A.).

Phage Detection by Fluorescent Microscopy and Flow Cytometry

Mouse Pancreatic ductal adenocarcinoma (PDAC) cells, human PDAC cells (i.e. MNA, 8988, SW1990, PaCa-2, ASPC), normal human ductal cells and normal pancreatic cells were incubated with 1 mM (FITC) FITC-labeled phage clone 27 or unrelated phage clone (amino acid sequence SNLHPSD, negative control (SEQ ID NO:XX)) for 1 hour at 37° C., washed 3× with DPBS and visualized by fluorescent microscopy (Nikon Eclipse TE2000-S, Insight QE, 40× objective). The cells were then harvested by incubation with trypsin, centrifuged, and analyzed (10,000 cells/sample) by flow cytometry on a Beckton Dickinson FACSCalibur (San Jose, Calif.). Samples of PDAC cells showed a single narrow peak of fluorescent intensity that was higher than from normal cells (e.g., FIG. 1B). Mean fluorescence was plotted against cell number to show relative uptake between cell types.

Ex Vivo Biopsy Specimens

Pancreatic ductal adenocarcinoma (PDAC)-specific peptides identified by phage studies were tested for binding on histology sections. In particular, ex vivo mouse and human tissue sections from biopsy specimens were snap frozen, embedded in OCT, cut into 5 μm sections, and then attached to slides. Slides with tissues were incubated with 1 μM of FITC labeled Phage Clone 27 or FITC labeled control phage (no insert) for 1 hour at 37° C., washed 3× with PBS, fixed with 2% paraformaldehyde, and then visualized by fluorescence microscopy (Nikon Eclipse TE2000-S, Insight QE, 40× objective).

Identification of a Binding Partner for a Phage Expressed Peptide

Phage were labeled with a photolinker (Sulfo-SAED (Sulfosuccinimidyl 2-[7-amino-4-methylcoumarin-3-acetamido]ethyl-1,3 dithiopropionate; Pierce, Waltham, Mass.) and biotin tag using the same NHS chemistry used to conjugate fluorochromes to phage (Kelly et al., Neoplasia 8: 1011-1018 (2006)). Two Petri dishes (10 cm, Fisher scientific, Waltham, Mass.) were plated with the target cell line and grown to until confluency where the cells covered the plate. One confluent plate was incubated with 1 mL of the modified phage (roughly 10$^{10}$ PFU/uL). For a negative control, the second plate was incubated with control (no insert) phage. Both plates were incubated in the dark at 4° C. for one hour. The cells were then again washed several times with DPBS, placed on ice, and photolyzed 30 min using a 15 watt 365 nm UV lamp (Spectroline, Westbury, N.Y.), and lysed using 1% triton x-100 in PBS with mammalian protease inhibitor cocktail added (Sigma, St. Louis, Mo.), The cell lysates were incubated 1 hr with 100 μL of Dynal Strepavidin beads (Invitrogen, Carlsbad, Calif.) which were pre-blocked with 5% BSA in PBS. The beads were washed twice with 1% triton x-100 in 10×PBS, then incubated overnight at 4° C. with a buffer containing DTT to reverse the chemical crosslink and release the precipitated protein. Half of the eluate was transferred to PVDF membrane and probed with plectin-1 antibody (Santa Cruz Biotechnology, Santa Cruz, Calif.). The other half of the eluate was loaded onto a SDS/PAGE gel (Biorad Criterion system, Hercules, Calif.) and stained using a mass spectroscopic compatible silver stain (Invitrogen, Carlesbad, Calif.).

The silver stained band was then excised and sent for tryptic digest/mass spec analysis (Tufts Peptide Core Facility). Nanobore electrospray columns were constructed from 360 mm o.d., 75 mm i.d. fused silica capillary with the column tip tapered to a 15 mm opening. The columns were packed with 200 A° Å 5 um C18 beads (Michrom Bioresearches, Auburn, Calif.), a reverse-phase packing material, to a length of 10 cm. The flow through the column was split precolumn to achieve a flow rate of 350 nL/min. The mobile phase used for gradient elution consisted of (A) 0.3% acetic acid 99.7% water and (B) 0.3% acetic acid 99.7% Acetonitrile. Tandem mass spectra were acquired on a Thermo LTQ ion trap mass spectrometer (Thermo Corp., San Jose, Calif.). Needle voltage was set at 3 kV. Ion signals above a predetermined threshold automatically triggered the instrument to switch from mass spectrometry (MS) to tandem mass spectrometry (MS/MS) mode for generating fragmentation spectra. The MS/MS spectra were searched against the NCBI nonredundant protein sequence database using the SEQUEST computer algorithm (Yates et al., Anal Chem 67: 1426-1436 (1995)).

Verification of Clone 27 (Panc 27) Binding to Plectin-1

Subcellular fractionation: PDAC, PaCa-2, NIH-293T, and the normal ductal cells were cultured overnight in two wells of a six well plate. The cells were harvested via scraping with 500 μL of cell lysis buffer (CLB; 10 mM HEPES/10 mM NaCl/1 mM KH$_2$PO$_4$J 5 mM NaHCO$_3$/1 mM CaCl$_2$/0.5 mM MgCl$_2$)/5 m MEDTA/10 μg/ml aprotinin+10 μg/ml leupeptin+1 ug/ml pepstatin. The harvested cells were allowed to swell for five minutes, homogenized 50 times then centrifuged at 7500 rpm for five minutes. The pellet was suspended in 1 ml TSE/0.1% NP40/PI and homogenized for 30 minutes followed with centrifugation at 5000 rpm for 5 minutes. The pellet was washed twice and suspended in 50 μl of TSE/0.1%/NP40/PI, leaving pure nuclei. The supernatant containing the cytosol with plasma membrane was centrifuged in a SWT0 rotor at 70,000 rpm for one hour. The pellet was resuspended and washed 2× with CLB to remove contaminating cytoplasmic proteins. Protein concentration of each fraction was determined via BCA assay (PIERCE Biotechnology), and equal amounts of protein from each fraction were size-fractionated by SDS-PAGE. Fractions were analyzed for plectin-1 expression via western blotting.

Competition experiments: mouse PDAC cells were incubated with FITC-labeled phage Clone 27 and either anti-plectin-1 antibody or vehicle for 1 hour at 37° C., washed, detached, then analyzed via flow cytometry (Becton Dickinson FACsCalibur (San Jose, Calif.)).

Peptide Synthesis

Plectin-1 Targeted Peptide (PTP) (amino acid sequence: KTLLPTP (SEQ ID NO:1)) and control peptide, see above, were synthesized with a GGSK(FITC)C (SEQ ID NO:27) linker for conjugation of the peptide to a model fluorescent nanoparticle (crosslinked iron oxides [CLIO]-Cy5.5).

Figure 8A:
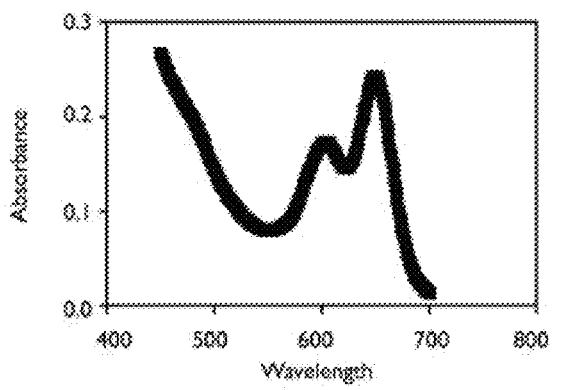
FIG. 8A is a line graph showing CLIO-Cy5.5 absorbance spectroscopy used for quantitation of number of Cy5.5/nanoparticle.
Figure 8B:
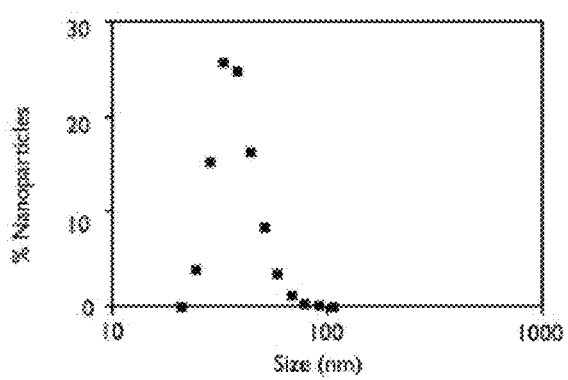
FIG. 8B is a dot graph of size distribution of CLIO via light scattering.

CLIO-Cy5.5 was synthesized in bulk using established procedures (see Montet et al., Bioconjug Chem 17:905-911 (2006); Reynolds et al., Bioconjug Chem 16:1240-1245 (2005); Wunderbaldinger et al., Acad Radiol 9 Suppl 2:S304-S306 (2002); and Schellenberger et al., Bioconjug Chem 15:1062-1067 (2004)), and aliquots used for the synthesis of the various nanoparticle conjugates. Briefly, T-10 dextran was dissolved in water mixed with ferric chloride and degassed by nitrogen purging. Ferric chloride solution was added to the mixture and the pH brought to 10 with ammonium hydroxide. The resulting particles were crosslinked with epichlorohydrin and ammonia to provide stability and amine groups for conjugation of fluorochromes and peptides. NHS-Cy5.5 was reacted with amino-CLIO in PBS overnight at 4° C. and purified by size exclusion chromatography. Determination of Cy5.5 loading onto CLIO was done by absorbance spectroscopy at 680 nm using unreacted CLIO as a reference (FIG. 8A). CLIO-Cy5.5 had the following physical properties: (a) size 38.7 nm (FIG. 8B), (b) relaxation time constants R1-21.1 and R2-62.6 mM/s, and (c) an average of 2.3 Cy5.5 per CLIO nanoparticle.

Figure 8C:
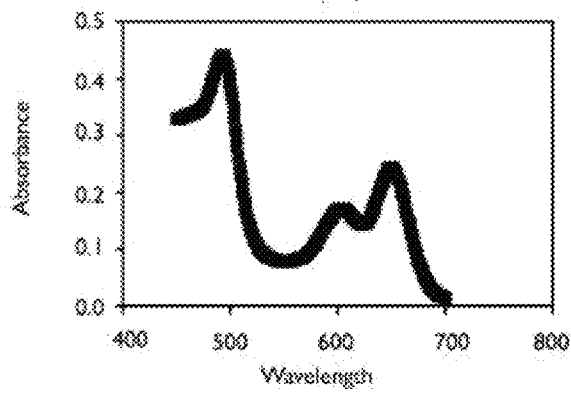
FIG. 8C is a line graph showing the results of absorbance spectroscopy of PTP-NP-Cy5.5 used to quantitate the number of peptides/nanoparticle. Notice background absorbance from nanoparticle below 500 nm, whose contribution is subtracted via reference to unreacted CLIO.

To produce plectin-1 targeted or control nanoparticles, succinimidyl iodoacetic acid was reacted with CLIO-Cy5.5 for 15 min, purified by size exclusion chromatography, then reacted with peptidyl-cysteine for 1 hour. Peptide-conjugated nanoparticles (PTP-NP) or controls (control-NP) were purified again using size exclusion chromatography and the ratio of peptides to nanoparticles was quantified at 497 nm by absorbance spectroscopy using unreacted CLIO as a reference (FIG. 8C).

Intravital Laser Scanning Microscopy

Laser scanning microscopes with far red and near infrared imaging capabilities (IV 100, Olympus, Tokyo) have been described in details elsewhere (see, e.g., Alencar et al., Int. J. Cancer 117:335-339 (2005)). During all imaging sessions, mice were anesthetized (2% isoflurane in 2 l/minute $O_2$) and a small midline incision performed to expose the pancreas. As an in vivo screening approach, the inventors have used phage as targeted nanoparticles for imaging by labeling the phage coat proteins with a near infrared fluorochrome (Kelly et al., Neoplasia 8:1011-1018 (2006); and Newton et al., Neoplasia 8:772-780 (2006)). The Cy5.5 labeled phage were injected I.V. 4 hours prior to imaging for both the distribution and tumor imaging studies. SYTOX green was injected 10 minutes prior to imaging (FIG. 3). Subsequent to imaging, tumors were removed for histological analysis. Serial frozen sections were hematoxylin and eosin (H&E) stained and also stained for the presence of M13 phage. For PTP-NP imaging (FIGS. 5 and 6), the agent was injected 24 hours prior to IV 100 imaging. Angiosense (Visen Medical, Woburn, Mass.) was injected 10 minutes prior to imaging to visualize microvasculature. Images were acquired using appropriate dual excitation (561 nm for RITC, 633 nm for Cy5.5 and 748 nm for Angiosense-750). After fluorescence imaging, the pancreas was removed and embedded in degassed 1% low melting point agar in PBS to prevent susceptibility interfaces subsequent MRI imaging.

Biodistribution

Mice were maintained on a nonfluorescent diet (Harlen-Teklad) for 3 days prior to imaging and received an intravenous injection of PTP-NP or control probe (15 mg Fe/kg body weight), coupled to Cy5.5 for fluorescent imaging, 24 hours before biodistribution studies were carried out. Excised tissues were rinsed in PBS and imaged on the Siemens Bonsai system and Olympus OV100 system using Cy5.5 filters. Probe accumulation in tissues was compared to free probe, and biodistribution data were expressed as a percentage of injected dose. Fluorescence differences between the tissues were corrected by imaging tissues/organs from animals with no probe injected then subtracting this background from the total signal.

Magnetic Resonance Imaging (MRI)

Pancreata imaged optically in vivo were then embedded, and ex vivo MRI studies performed to directly correlate intrapancreatic signal intensity changes with histology. Imaging of resected and agar-embedded specimen was performed using a Bruker 4.7T Pharmascan magnet, with a 38 mm diameter transmit-receive radiofrequency coil. Scout and localizer images were obtained, followed by high resolution fast spin echo (FSE) and gradient echo sequences (GE). Specifically, for the T2 weighted FSE sequence, the following parameters were used: FOV 4.94×5.46 cm, matrix size of 512×512, slice thickness of 0.5 mm, RARE factor of 8, TE (effective) of 40 ms, TR 2811 ms, NEX of 50 for a total acquisition time of 2 hr 29 minutes. For the T2*weighted GE sequence, the parameters were: FOV 3×3 cm, matrix size 512×512, slice thickness of 0.5 mm, TE of 6.8 ms, TR of 398 ms, flip angle of 30 degrees, NEX of 50, for a total acquisition time of 2 hours 49 minutes. Fiducial markers were included to subsequently co-register high resolution MRI data sets with histologic sections.

Histology and Immunohistochemistry

Pancreas and PDAC specimens were isolated and either fixed in 10% paraformaldehyde or frozen in optimum cutting temperature (O.C.T.) compound as previously described (Bardeesy et al., Proc Natl Acad Sci USA 103:5947-5952 (2006)). The histology and immunohistochemical analyses were done as previously-described (Bardeesy et al., (2006) supra).

Serial frozen sections were stained with H&E or for the presence of M 13 (Amersham Biosciences, Piscataway, N.J.) (FIG. 3) and plectin-1 (FIG. 4). Digital images were taken using a Nikon Eclipse E400 upright microscope (×20 and ×43 objective) equipped with an Insight color camera. Serial frozen sections were stained with HE or imaged via fluorescence microscopy for the presence of PTPNP-Cy5.5 using a Nikon Eclipse 80i inverted microscope (203 objective) equipped with a 512 Photometrics Cascade CCD camera (Nikon).

Example II

In Vitro Selection and Validation of PDAC-Specific Peptides

Figure 9:
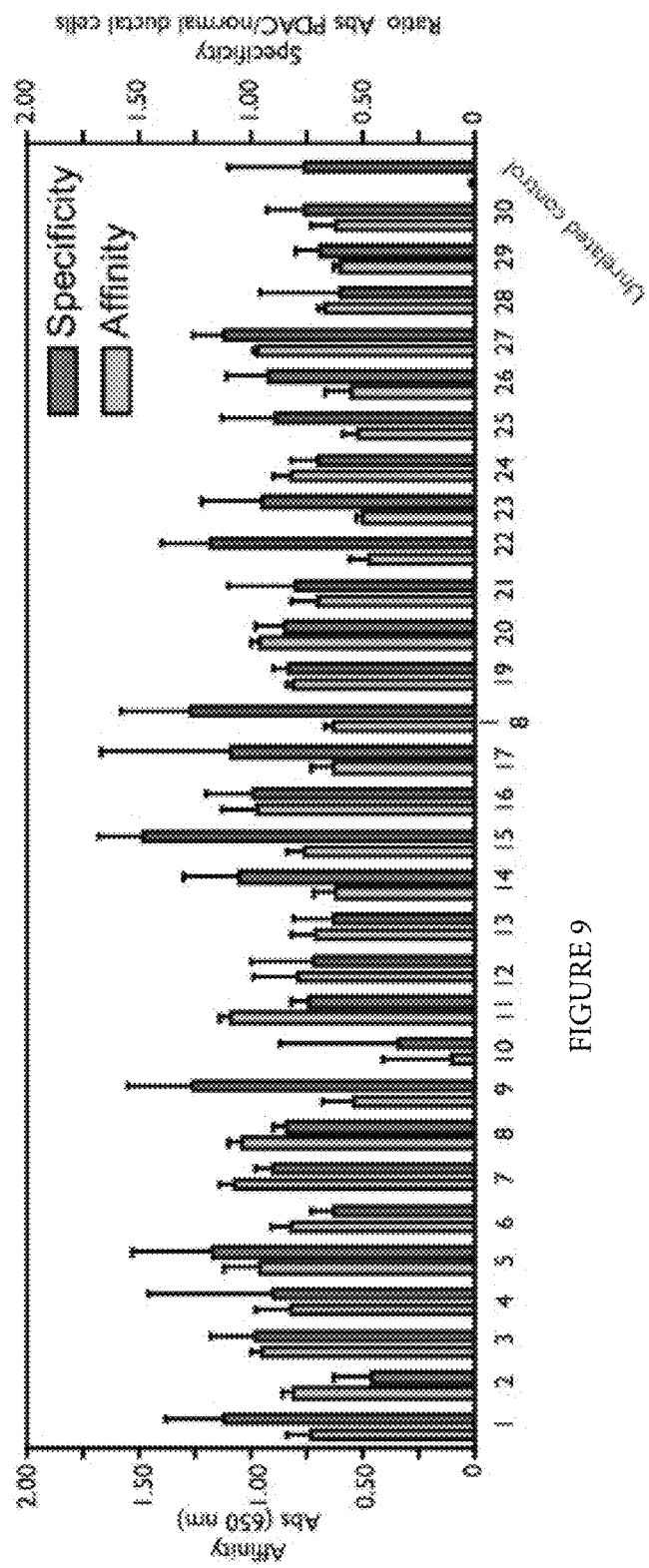
FIG. 9 is a bar graph showing an exemplary phage clone validation Via ELISA. After selection and subtraction, 30 individual phage clones were picked, amplified, and analyzed for affinity and specificity via ELISA.

A genetically engineered mouse model of PDAC that recapitulates many of the histopathological, genomic and molecular features of the human disease was used (Carrière et al., Proc Natl Acad Sci USA. 104(11):4437-42 (2007); and Bardeesy et al. Proc Natl Acad Sci USA 103:5947-5952 (2006)). The Kras/p53 L/L model (Bardeesy et al., Proc Natl Acad Sci USA 103:5947-5952 (2006)) and wildtype controls served as a source of well-defined early passage PDAC cell lines and normal pancreatic ductal cells, respectively, for use in phage display selection and subtraction procedures to identify a pool of phage peptides specific for PDAC cells. Subsequent to selection procedures, the inventors isolated thirty individual phage plaques and performed an ELISA to identify the most selective phage for PDAC cells. The results of two experiments performed in triplicate are presented in the heat map shown in FIG. 1A and in the bar graph shown in FIG. 9. The heat map depicts affinity (mean absorbance values of indicated clones from the ELISA assay) and specificity (ratio of absorbance for PDAC cells versus normal ductal cells). Of the thirty phage clones analyzed, 16 phage clones (53%) had specificity for PDAC cells greater than 2 fold. Seven clones (Nos. 1, 5, 9, 15, 17, 22, and 27) were chosen for sequencing on the basis of ELISA and multidimensional analysis. For exemplary ELISA and sequencing methods see, e.g., Kelly et al., Circ. Res. 96:327-336 (2005); Kelly et al., Neoplasia 8:1011-1018 (2006)). Sequence results showed that Clones 27 and 5 shared identical peptide sequences (KTLLPTP, SEQ ID NO:1) and demonstrated ideal high affinity and specificity for the target PDAC cells.

Validation of Clone 27 as a PDAC marker (FIG. 1B) was done in experiments described herein, in addition to testing clones 1 (SGVEFLH, SEQ ID NO:4), 9 (SKKDTHH, SEQ ID NO:5), 15 (TMAPSIK, SEQ ID NO:6), 17 (TQHQVTA, SEQ ID NO:7), and 22 (VNDRNVK, SEQ ID NO:8). The phage coat proteins were fluorescein labeled then the extent of phage clone binding and specificity quantified for mouse PDAC and normal ductal cells via flow cytometry (FIG. 1B). The results showed that Clone 27 was highly specific for mouse PDAC cells having a 112-fold specificity over normal ductal cells (FIG. 1C). Thus Clone 27 (SEQ ID NO:1—KTLLPTP) demonstrated ideal affinity and specificity for the target PDAC cells (Kelly, et al., (2006) Neoplasia 8:1011-1018; Kelly et al. (2005) Circ Res 96: 327-336, all of which are herein incorporated by reference). Phage clone 15 was second in affinity with the remainder having nearly identical specificity.

Together, these data demonstrate the effectiveness of a cancer model-based phage screen as described herein for the identification and validation of phage clones with high affinity and specificity for cancer cells, such as mouse PDACs.

Example III

Determining Specificity of Peptides for Human PDACs

The specificity of Clone 27 for human PDAC cells was evaluated as described in this example. Clone 27 and an unrelated phage clone were labeled with FITC, producing FITC-27 and a FITC-unrelated phage clone (negative control). Mouse PDAC cells as a positive control along with five human PDAC cell lines and with normal human ductal cells were incubated with each type of clone and then uptake of the clone was analyzed via fluorescence-activated cell sorter (FACS). FITC-27 (Clone 27) had an average specificity for PDAC cell lines of 141 (ratio of clone 27/unrelated clone mean fluorescence) when compared with unrelated phage. In addition, the two phage clones (FITC-27 and FITC-unrelated) showed nearly identical, weak binding to normal human ductal cells (specificity=0.85) (FIG. 1C).

Example IV

Utilizing Peptides for Identifying Human PDACs

Figure 2:
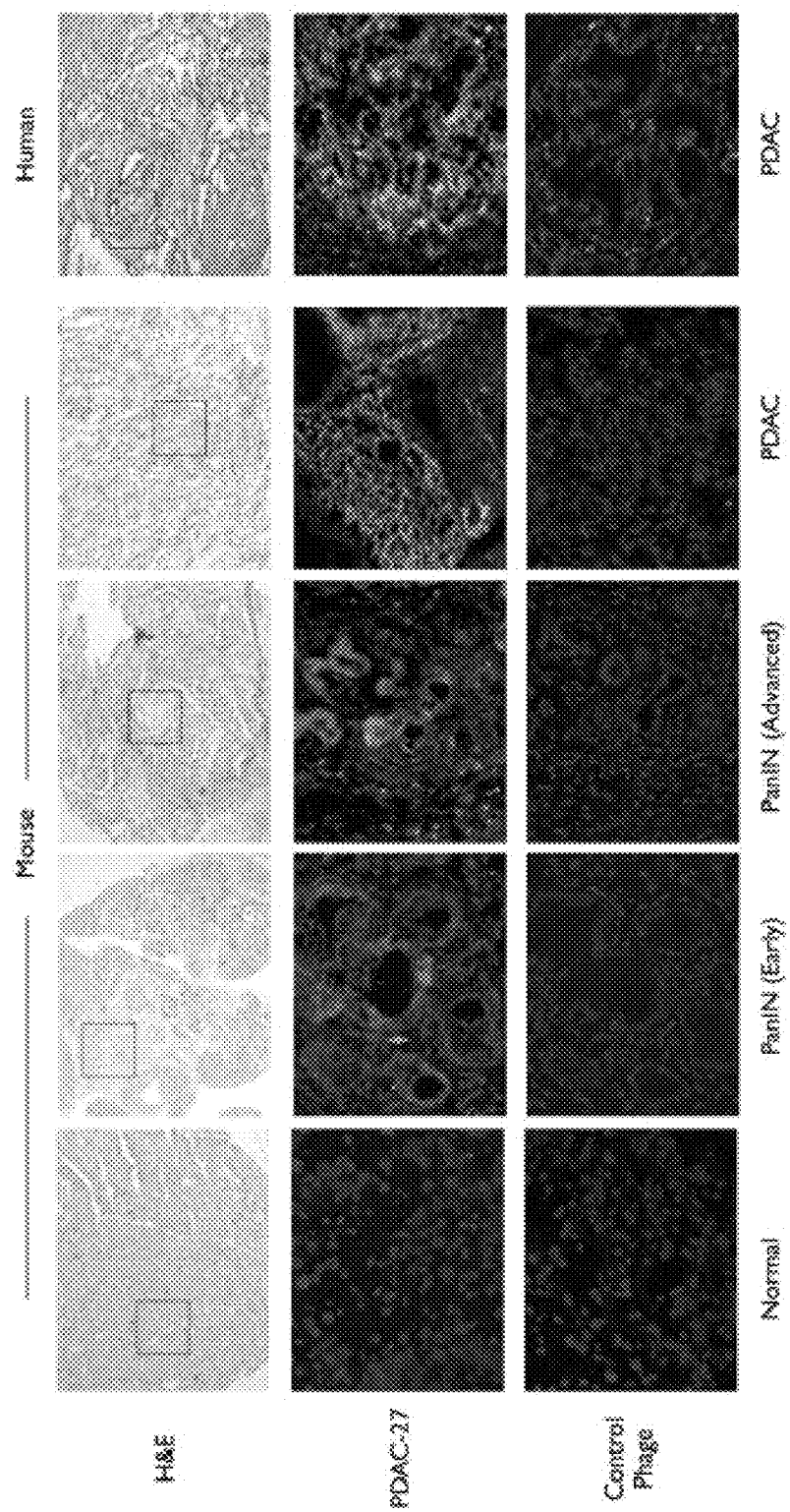
FIG. 2 is a set of 15 panels showing exemplary Clone 27 in vivo detection of human and mouse pancreatic ductal adenocarcinoma cells (PDAC). Fluorescein isothiocyanate (FITC) labeled-clone 27 or wild type phage (no peptide insert) were incubated with frozen sections of indicated tissue, mouse and human, pancreas sections stained with Hematoxylin and Eosin (H & E) Clone 27 (PDAC-27).

The use of the identified phage for the detection of mouse and human PDACs was demonstrated as follows. Phage 27 labeled with a fluorochrome was used as a probe to test binding to frozen sections of normal pancreas, pancreases containing focal PanINs, and pancreata with PDAC. While no binding was observed in wild-type mouse pancreata or in normal regions adjacent to lesions, prominent binding was observed in PanINs and PDAC lesions. Control phage failed to detect any lesions (FIG. 2, bottom row). Significantly, phage Clone 27 was able to specifically detect human PDAC, whereas control phage failed to stain human PDAC specimens (FIG. 2, (far right)). These results demonstrate that the phage probes bind to evolving mouse and human PDAC, supporting the utility of our models-based screening approach for the generation of candidate PDAC-specific diagnostic agents.

Example V

Tumor Localization of PDAC Targeted Phage

Figures 3A, 3B, 3C:
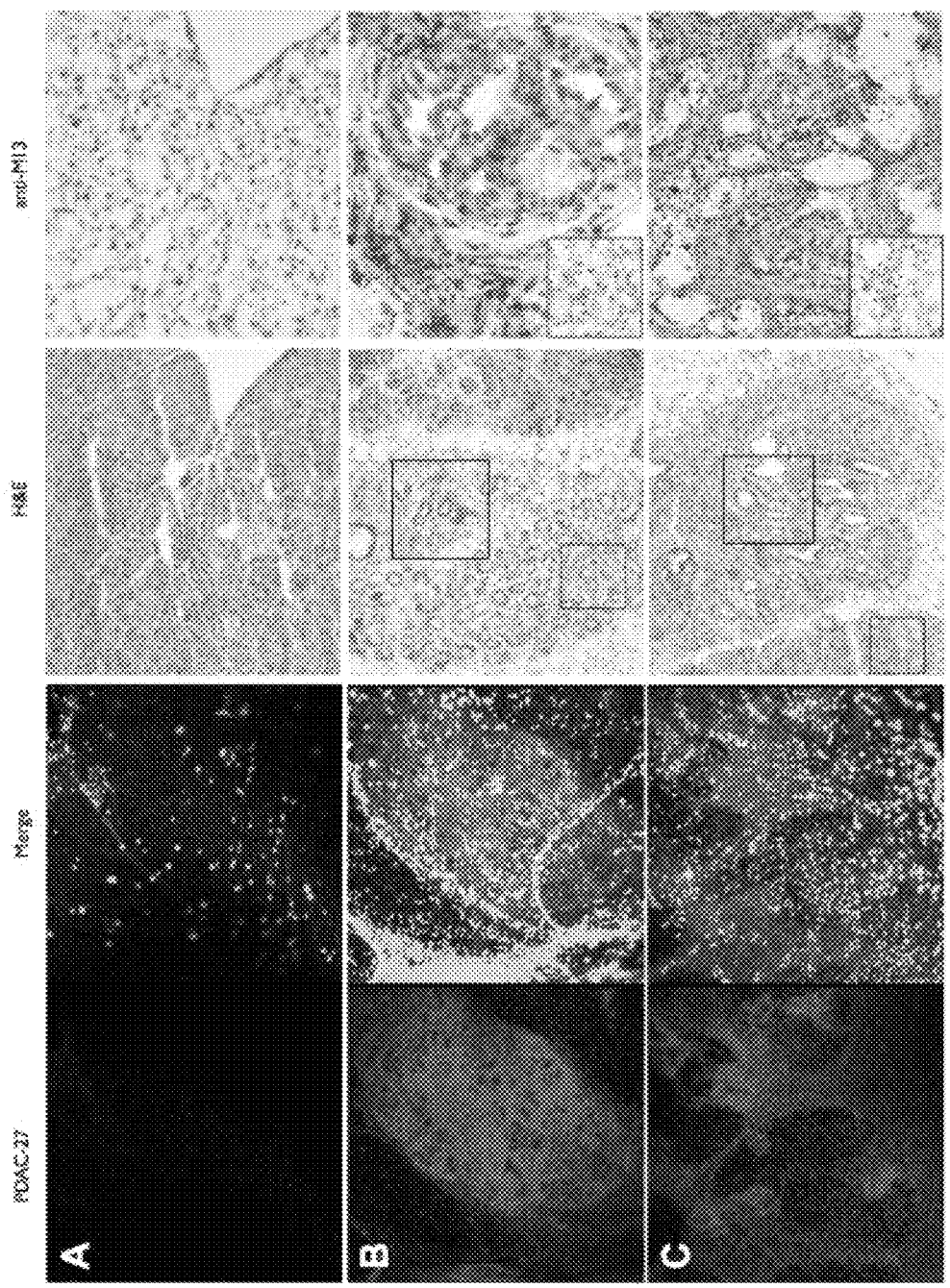
FIGS. 3A-C are each four panels showing exemplary in vivo validation of Clone-27. 3A, wild type; 3B, 29-week old Kras/p16+/−; and 3C, 12-week old Kras/p53$^{L/+}$ mice were injected with Cyanine 5.5 labeled phage Clone 27 and SYTOX green (nonspecific cell-labeling agent) then imaged via intravital confocal microscopy. Correlative Histology: Pancreata from intravital imaging experiments were embedded in Optimal Cutting Temperature (OCT) compound, frozen, and stained with anti-M13 antibody (third column) Hematoxylin and Eosin (H & E) (fourth column). Black boxes correspond to regions of PanINs (3B) or PDAC (3C) and are magnified in the anti-M13 photomicrograph. Upper boxes in 3B and 3C, HE and inset in anti-M13 photomicrograph (third and fourth columns) correspond to uninvolved adjacent regions.

Since phage clones 27 and 15 had the most favorable binding characteristics in vitro, these clones were further tested for in vivo binding in wild-type animals, animals harboring PanINs, and animals harboring palpable pancreatic tumors. These animals were injected via tail vein with 1 nanomole of fluorescently labeled phage clone 27 and phage clone 15—alone or in combination—and then imaged via intravital confocal microscopy 4 h postinjection (FIG. 10A). Clone 27 illuminated PanINs and PDAC with a strong fluorescent signal, suggesting phage binding to tumors cells, whereas only a weak scattered signal was observed in the pancreas of wild-type mice (FIGS. 3A, 3B, and FIG. 10C). The fluorescent signal was virtually absent when control phage was injected into animals harboring emerging or advanced PDAC (FIG. 10B). Clones 15 and 27 showed distinctly different distributions within the pancreas and also different peptide sequences (FIG. 10A), suggesting they target unique proteins. However while clone 15 did localize to the pancreas, total signal was less than that of clone 27, thus further experiments were focused on Clone 27.

Further documentation of the specificity of phage Clone 27 binding in vivo, pancreata from clone 27-injected animals were fixed and analyzed by immunohistochemistry using antibodies specific to phage coat proteins (FIG. 3). In areas with PanINs or PDAC (black boxes in FIGS. 3B and 3C), there was strong uptake of phage whereas in regions of ductal metaplasia or normal pancreas (red boxes in FIGS. 3B and 3C) phage were undetectable. These studies supported the specificity of Clone 27 for cancer cells showing that phage clone 27 was localized to PanINs and PDAC while absent in normal pancreatic tissues or regions of ductal metaplasia, which are low-grade neoplasms or reactive lesions associated with pancreatic damage (FIG. 3) (Murtaugh et al., Cancer Cell 11: 211-213 (2007)).

Example VI

Identification of Plectin-1 as the Binding Partner for Peptide 27

Since clone 27 showed specificity for human and mouse PDAC in vitro and in vivo, the next step was to determine its cellular binding partner. Using the phage as an affinity ligand, a unique 500 kDa band was identified in the mouse PDAC cell lysates via pulldown assay (FIG. 4A, left panel). In addition, far western analysis of PDAC lysates with biotinylated phage as the probe identified a band of similar molecular weight that was not recognized by control phage (FIG. 4A, right panel). Mass spectroscopic analysis of the isolated band revealed plectin-1, an intermediate, filament and important cross-linking element of the cytoskeleton (FIG. 4B) (Sonnenberg, et al. (2007) Exp Cell Res 313: 2189-2203). Western blot using lysates from the phage pull down confirmed the presence of a band that crossreacts with the plectin-1 antibody (FIG. 4C). Plectin-1 was found to be present in the cellular membrane as well as the nucleus and cytoplasm of both murine and human PDAC cells (FIG. 4D). Normal mouse pancreatic ductal cells showed low levels of plectin-1 expression, whereas normal human pancreatic ductal cells showed plectin-1 expression in the cytoplasm and nucleus but not on the membrane (FIG. 4D). In contrast, HUVECs showed very low levels of plectin-1 expression in the nucleus. NIH-3T3 cells were used as a control for cellular locations of plectin-1 expression because they were known to have plectin-1 in the cytoplasm and nucleus but not on the cell surface (Sonnenberg et al., Exp Cell Res 313: 2189-2203 (2007)). As was expected in the control cells, plectin-1 was absent from the membrane but present in the cytoplasmic and nuclear fractions of fibroblasts (FIG. 4D).

Immunohistochemical analysis of sections from normal, PanIN, and PDAC-harboring mice corroborated the Western analysis findings. Normal animals had scattered plectin-1 staining, whereas in PanINs and PDAC, plectin-1 was expressed in the lesions but not in the surrounding tissue (FIG. 4E). The plectin-1 staining patterns were nearly identical to that observed by PDAC-targeted phage shown in FIG. 3 and FIG. 4E. Finally, in a competition experiment, coincubation of anti-plectin-1 antibody and FITC-labeled phage clone 27 with PDAC cells resulted in 96.9% abrogation of binding (FIG. 4F).

Example VII

Development of Plectin-1 Targeted PDAC Imaging Agents

In order to develop a nonbiologic, synthetic imaging agent with translational potential, the inventors chemically synthesized and attached PTP to a magnetofluorescent nanoparticle (PTP-NP) (schematic, FIG. 5A).

The resultant MRI/optically detectable agent was tested in 9-wk-old Kras/p53L/⁺ mice (FIG. 6A). At that age, these mice do not exhibit outward signs of illness but typically harbor small, focal PDAC, as well as regions of normal pancreas, ductal metaplasia, and fibrosis. Twenty-four hours after IV administration of the targeted nanoparticle, intravital confocal microscopy detected discrete areas of fluorescence in the abdominal region of these mice, suggestive of agent uptake (FIG. 5B upper left and 6B, left). The agent was specifically present in the tumor tissue as a vasculature agent administered 10 min before injection failed to colocalize (FIG. 5B upper right and 6B, right). The in vivo fluorescence correlated with surface reflectance imaging of the excised pancreas where discrete foci of signal were found (FIGS. 5C, 6C and 6D). In contrast, control-NP failed to highlight any regions of the pancreas (FIG. 5B, lower left), although these tumors were similarly vascularized (FIG. 5B, lower right).

Biodistribution studies revealed specific uptake in tumors with minimal uptake in muscle or skin, two tissues with reported plectin-1 expression (FIG. 5D). In addition, tumor uptake relative to normal pancreas was 10.1-fold higher.

Figure 7A:
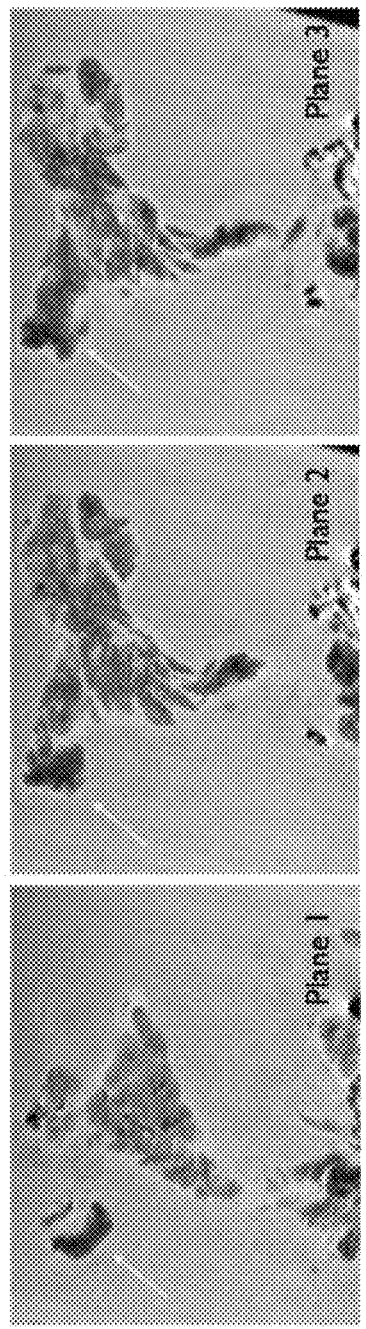
FIGS. 7A-C show an exemplary Magnetic resonance imaging (MRI) and correlative histology. 7A, Three adjacent slices from an ex vivo MRI of the pancreas from a 9-week old Kras/p53$^{L/+}$ mouse demonstrates focal nanoparticle uptake (yellow arrow), which corresponds to tumor seen on correlated Hematoxylin and Eosin (H & E) sections (7B) but not to regions of ductal metaplasia or normal pancreas (labeled). (7C) Fluorescence microscopy of adjacent sections demonstrate uptake of Cy5.5-labeled plectin-1 targeted peptide conjugated nanoparticles (PTP-NP) in regions of tumor (left) but not in adjacent tissue (right).

Similarly, MRI showed a reduction in magnetic resonance (MR) signal indicative of agent presence in focal regions of the pancreas (FIG. 7A). From the biodistribution data, 3.13%-injected dose of material was present in the tumors. Using previously established thresholds for direct MRI sensitivity of 10 ng of Fe/g of tissue (Weissleder et al. (1997) J Magn Reson Imaging 7: 258-263 (1997)), the resulting signal was calculated at 20-fold over the threshold of detection. In addition, it is likely that current sensitivity is higher than what was previously published given available motion correction and multi-echo chemical sequences.

Figure 7C:
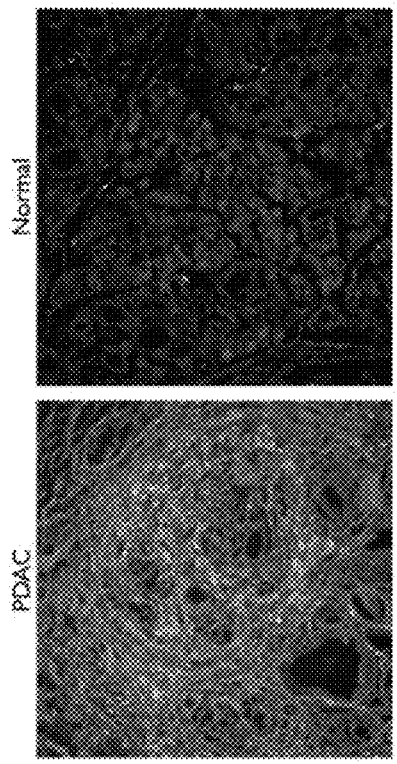
Figure 7B:
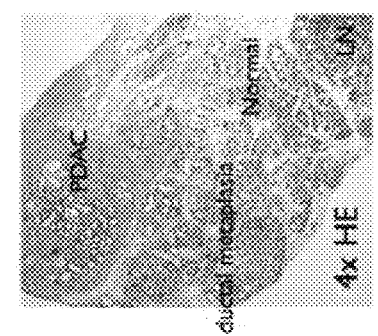

Histological analysis confirmed that the loss of signal associated with PTP-NP uptake was primarily in regions of PDAC but not in normal regions or regions of ductal metaplasia (FIG. 7B). Fluorescence microscopy of the sections demonstrated PTP-NP accumulation in areas of PDAC (FIG. 7C, left) but not in areas of normal pancreas (FIG. 7C, right).

Other Embodiments

All publications and patents mentioned in the above specification are herein incorporated by reference in their entirety. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in medicine, therapeutics, pharmaceuticals, MRI, in vivo imaging, molecular biology, biochemistry, chemistry, and cell biology or related fields are intended to be within the scope of the following claims. All references cited herein are incorporated in their entirety.

What is claimed is:

1. A method of treating cancer in a subject, the method comprising administering to the subject a therapeutically effective amount of a peptide ligand comprising:
   a first portion comprising a plectin-1 binding moiety, coupled to
   a second portion comprising a therapeutic agent.

2. The method of claim 1, wherein the therapeutic agent is a cytotoxic moiety or an immunomodulatory moiety.

3. The method of claim 1, wherein the plectin-1 binding moiety is an amino acid sequence selected from the group consisting of SEQ ID NOs: 1, 2, or 4-8, or a peptidomimetic thereof.

4. The method of claim 1, wherein the peptide ligand further comprises a linker between the first portion and the second portion.

5. The method of claim 4, wherein the linker is a flexible amino acid sequence.

6. The method of claim 4, wherein the linker is a photolinker.

7. The method of claim 1, wherein the peptide ligand further comprises a physiologically inert nanoparticle.

8. The method of claim 7, wherein the nanoparticle is magnetic, fluorescent, or radioactive.

9. The method of claim 1, wherein the cancer is pancreatic ductal adenocarcinoma (PDAC).

10. The method of claim 1, wherein the cancer is ovarian cancer.

* * * * *

SEQUENCE LISTING

```
<160> NUMBER OF SEQ ID NOS: 27

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Lys Thr Leu Leu Pro Thr Pro
1               5
```

```
<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Lys Thr Leu Leu Pro Thr Pro Gly Gly Ser Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: 11
<223> OTHER INFORMATION: Conjugated Fluorescein isothiocyanate (FITC)

<400> SEQUENCE: 3

Lys Thr Leu Leu Pro Thr Pro Gly Gly Ser Lys Cys
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Ser Gly Val Glu Phe Leu His
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Ser Lys Lys Asp Thr His His
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Thr Met Ala Pro Ser Ile Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7
```

Thr Gln His Gln Val Thr Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Val Asn Asp Arg Asn Val Lys
1               5

<210> SEQ ID NO 9
<211> LENGTH: 14
<212> TYPE: PRT
<213> ORGANISM: Artificial Sequence
<220> FEATURE:
<223> OTHER INFORMATION: Synthetic peptide

<400> SEQUENCE: 9

Asp Ser Gln Asp Ala Gly Gly Phe Pro Gly Pro Glu Asp Arg
1               5                   10

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide

<400> SEQUENCE: 10

Glu Ala Gln Ala Val Pro Ala Thr Leu Gln Glu Leu Glu Ala Thr Lys
1               5                   10                  15

<210> SEQ ID NO 11
<211> LENGTH: 14
<212> TYPE: PRT
<213> ORGANISM: Artificial Sequence
<220> FEATURE:
<223> OTHER INFORMATION: Synthetic peptide

<400> SEQUENCE: 11

Ala Gln Ala Glu Ala Gln Gln Pro Val Phe Asn Thr Leu Arg
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Gly Gly Ala Glu Gly Glu Leu Gln Ala Leu Arg
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

```
Leu Ala Ala Glu Gln Glu Leu Ile Arg
1               5
```

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide

<400> SEQUENCE: 14

```
Leu Arg Ala Glu Thr Glu Gln Gly Glu Gln Gln Arg
1               5                   10
```

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide

<400> SEQUENCE: 15

```
Ser Lys Glu Gln Ala Glu Leu Glu Ala Ala Arg
1               5                   10
```

<210> SEQ ID NO 16
<211> LENGTH: 11
<212> TYPE: PRT
<213> ORGANISM: Artificial Sequence
<220> FEATURE:
<223> OTHER INFORMATION: Synthetic peptide

<400> SEQUENCE: 16

```
Ala Gln Val Glu Gln Glu Leu Thr Thr Leu Arg
1               5                   10
```

<210> SEQ ID NO 17
<211> LENGTH: 11
<212> TYPE: PRT
<213> ORGANISM: Artificial Sequence
<220> FEATURE:
<223> OTHER INFORMATION: Synthetic peptide

<400> SEQUENCE: 17

```
Ser Gln Val Glu Glu Glu Leu Phe Ser Val Arg
1               5                   10
```

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

```
Leu Ser Val Ala Ala Gln Glu Ala Ala Arg
1               5                   10
```

<210> SEQ ID NO 19
<211> LENGTH: 11
<212> TYPE: PRT
<213> ORGANISM: Artificial Sequence
<220> FEATURE:
<223> OTHER INFORMATION: Synthetic peptide

<400> SEQUENCE: 19

```
Gln Leu Ala Glu Glu Asp Leu Ala Gln Gln Arg
```

-continued

```
1               5                   10
```

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

```
Leu Ser Val Tyr Thr Ala Leu Gln Arg
1               5
```

<210> SEQ ID NO 21
<211> LENGTH: 16
<212> TYPE: PRT
<213> ORGANISM: Artificial Sequence
<220> FEATURE:
<223> OTHER INFORMATION: Synthetic peptide

<400> SEQUENCE: 21

```
Leu Leu Asp Ala Gln Leu Ser Thr Gly Gly Ile Val Asp Pro Ser Lys
1               5                   10                  15
```

<210> SEQ ID NO 22
<211> LENGTH: 10
<212> TYPE: PRT
<213> ORGANISM: Artificial Sequence
<220> FEATURE:
<223> OTHER INFORMATION: Synthetic peptide

<400> SEQUENCE: 22

```
Leu Thr Ala Glu Asp Leu Tyr Glu Ala Arg
1               5                   10
```

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide

<400> SEQUENCE: 23

```
Val Ser Leu Asp Glu Ala Leu Gln Arg
1               5
```

<210> SEQ ID NO 24
<211> LENGTH: 4684
<212> TYPE: PRT
<213> ORGANISM: Homo sapiens

<400> SEQUENCE: 24

```
Met Val Ala Gly Met Leu Met Pro Arg Asp Gln Leu Arg Ala Ile Tyr
1               5                   10                  15

Glu Val Leu Phe Arg Glu Gly Val Met Val Ala Lys Lys Asp Arg Arg
                20                  25                  30

Pro Arg Ser Leu His Pro His Val Pro Gly Val Thr Asn Leu Gln Val
            35                  40                  45

Met Arg Ala Met Ala Ser Leu Arg Ala Arg Gly Leu Val Arg Glu Thr
        50                  55                  60

Phe Ala Trp Cys His Phe Tyr Trp Tyr Leu Thr Asn Glu Gly Ile Ala
65                  70                  75                  80

His Leu Arg Gln Tyr Leu His Leu Pro Pro Glu Ile Val Pro Ala Ser
                85                  90                  95
```

```
Leu Gln Arg Val Arg Arg Pro Val Ala Met Val Met Pro Ala Arg Arg
            100                 105                 110

Thr Pro His Val Gln Ala Val Gln Gly Pro Leu Gly Ser Pro Pro Lys
            115                 120                 125

Arg Gly Pro Leu Pro Thr Glu Glu Gln Arg Val Tyr Arg Arg Lys Glu
            130                 135                 140

Leu Glu Glu Val Ser Pro Glu Thr Pro Val Val Pro Ala Thr Thr Gln
145                 150                 155                 160

Arg Thr Leu Ala Arg Pro Gly Pro Glu Pro Ala Pro Ala Thr Asp Glu
                165                 170                 175

Arg Asp Arg Val Gln Lys Lys Thr Phe Thr Lys Trp Val Asn Lys His
                180                 185                 190

Leu Ile Lys Ala Gln Arg His Ile Ser Asp Leu Tyr Glu Asp Leu Arg
            195                 200                 205

Asp Gly His Asn Leu Ile Ser Leu Leu Glu Val Leu Ser Gly Asp Ser
            210                 215                 220

Leu Pro Arg Glu Lys Gly Arg Met Arg Phe His Lys Leu Gln Asn Val
225                 230                 235                 240

Gln Ile Ala Leu Asp Tyr Leu Arg His Arg Gln Val Lys Leu Val Asn
                245                 250                 255

Ile Arg Asn Asp Asp Ile Ala Asp Gly Asn Pro Lys Leu Thr Leu Gly
                260                 265                 270

Leu Ile Trp Thr Ile Ile Leu His Phe Gln Ile Ser Asp Ile Gln Val
            275                 280                 285

Ser Gly Gln Ser Glu Asp Met Thr Ala Lys Glu Lys Leu Leu Leu Trp
            290                 295                 300

Ser Gln Arg Met Val Glu Gly Tyr Gln Gly Leu Arg Cys Asp Asn Phe
305                 310                 315                 320

Thr Ser Ser Trp Arg Asp Gly Arg Leu Phe Asn Ala Ile Ile His Arg
                325                 330                 335

His Lys Pro Leu Leu Ile Asp Met Asn Lys Val Tyr Arg Gln Thr Asn
                340                 345                 350

Leu Glu Asn Leu Asp Gln Ala Phe Ser Val Ala Glu Arg Asp Leu Gly
            355                 360                 365

Val Thr Arg Leu Leu Asp Pro Glu Asp Val Asp Val Pro Gln Pro Asp
            370                 375                 380

Glu Lys Ser Ile Ile Thr Tyr Val Ser Ser Leu Tyr Asp Ala Met Pro
385                 390                 395                 400

Arg Val Pro Asp Val Gln Asp Gly Val Arg Ala Asn Glu Leu Gln Leu
                405                 410                 415

Arg Trp Gln Glu Tyr Arg Glu Leu Val Leu Leu Leu Gln Trp Met
                420                 425                 430

Arg His His Thr Ala Ala Phe Glu Glu Arg Arg Phe Pro Ser Ser Phe
            435                 440                 445

Glu Glu Ile Glu Ile Leu Trp Ser Gln Phe Leu Lys Phe Lys Glu Met
            450                 455                 460

Glu Leu Pro Ala Lys Glu Ala Asp Lys Asn Arg Ser Lys Gly Ile Tyr
465                 470                 475                 480

Gln Ser Leu Glu Gly Ala Val Gln Ala Gly Gln Leu Lys Val Pro Pro
                485                 490                 495

Gly Tyr His Pro Leu Asp Val Glu Lys Glu Trp Gly Lys Leu His Val
            500                 505                 510
```

```
Ala Ile Leu Glu Arg Glu Lys Gln Leu Arg Ser Glu Phe Glu Arg Leu
515                 520                 525

Glu Cys Leu Gln Arg Ile Val Thr Lys Leu Gln Met Glu Ala Gly Leu
530                 535                 540

Cys Glu Glu Gln Leu Asn Gln Ala Asp Ala Leu Leu Gln Ser Asp Val
545                 550                 555                 560

Arg Leu Leu Ala Ala Gly Lys Val Pro Gln Arg Ala Gly Glu Val Glu
                565                 570                 575

Arg Asp Leu Asp Lys Ala Asp Ser Met Ile Arg Leu Leu Phe Asn Asp
                580                 585                 590

Val Gln Thr Leu Lys Asp Gly Arg His Pro Gln Gly Glu Gln Met Tyr
            595                 600                 605

Arg Arg Val Tyr Arg Leu His Glu Arg Leu Val Ala Ile Arg Thr Glu
610                 615                 620

Tyr Asn Leu Arg Leu Lys Ala Gly Val Ala Ala Pro Ala Thr Gln Val
625                 630                 635                 640

Ala Gln Val Thr Leu Gln Ser Val Gln Arg Arg Pro Glu Leu Glu Asp
                645                 650                 655

Ser Thr Leu Arg Tyr Leu Gln Asp Leu Leu Ala Trp Val Glu Glu Asn
            660                 665                 670

Gln His Arg Val Asp Gly Ala Glu Trp Gly Val Asp Leu Pro Ser Val
            675                 680                 685

Glu Ala Gln Leu Gly Ser His Arg Gly Leu His Gln Ser Ile Glu Glu
            690                 695                 700

Phe Arg Ala Lys Ile Glu Arg Ala Arg Ser Asp Glu Gly Gln Leu Ser
705                 710                 715                 720

Pro Ala Thr Arg Gly Ala Tyr Arg Asp Cys Leu Gly Arg Leu Asp Leu
                725                 730                 735

Gln Tyr Ala Lys Leu Leu Asn Ser Ser Lys Ala Arg Leu Arg Ser Leu
                740                 745                 750

Glu Ser Leu His Ser Phe Val Ala Ala Ala Thr Lys Glu Leu Met Trp
            755                 760                 765

Leu Asn Glu Lys Glu Glu Glu Val Gly Phe Asp Trp Ser Asp Arg
770                 775                 780

Asn Thr Asn Met Thr Ala Lys Lys Glu Ser Tyr Ser Ala Leu Met Arg
785                 790                 795                 800

Glu Leu Glu Leu Lys Glu Lys Ile Lys Glu Leu Gln Asn Ala Gly
                805                 810                 815

Asp Arg Leu Leu Arg Glu Asp His Pro Ala Arg Pro Thr Val Glu Ser
                820                 825                 830

Phe Gln Ala Ala Leu Gln Thr Gln Trp Ser Trp Met Leu Gln Leu Cys
            835                 840                 845

Cys Cys Ile Glu Ala His Leu Lys Glu Asn Ala Ala Tyr Phe Gln Phe
850                 855                 860

Phe Ser Asp Val Arg Glu Ala Glu Gly Gln Leu Gln Lys Leu Gln Glu
865                 870                 875                 880

Ala Leu Arg Arg Lys Tyr Ser Cys Asp Arg Ser Ala Thr Val Thr Arg
                885                 890                 895

Leu Glu Asp Leu Leu Gln Asp Ala Gln Asp Glu Lys Glu Gln Leu Asn
                900                 905                 910

Glu Tyr Lys Gly His Leu Ser Gly Leu Ala Lys Arg Ala Lys Ala Val
            915                 920                 925

Val Gln Leu Lys Pro Arg His Pro Ala His Pro Met Arg Gly Arg Leu
```

```
            930             935             940
Pro Leu Leu Ala Val Cys Asp Tyr Lys Gln Val Glu Val Thr Val His
945                 950                 955                 960

Lys Gly Asp Glu Cys Gln Leu Val Gly Pro Ala Gln Pro Ser His Trp
                965                 970                 975

Lys Val Leu Ser Ser Gly Ser Glu Ala Ala Val Pro Ser Val Cys
                980                 985                 990

Phe Leu Val Pro Pro Asn Gln Glu Ala Gln Glu Ala Val Thr Arg
                995                1000                1005

Leu Glu Ala Gln His Gln Ala Leu Val Thr Leu Trp His Gln Leu His
            1010                1015                1020

Val Asp Met Lys Ser Leu Leu Ala Trp Gln Ser Leu Arg Arg Asp Val
1025                1030                1035                1040

Gln Leu Ile Arg Ser Trp Ser Leu Ala Thr Phe Arg Thr Leu Lys Pro
                1045                1050                1055

Glu Glu Gln Arg Gln Ala Leu His Ser Leu Glu Leu His Tyr Gln Ala
                1060                1065                1070

Phe Leu Arg Asp Ser Gln Asp Ala Gly Gly Phe Gly Pro Glu Asp Arg
                1075                1080                1085

Leu Met Ala Glu Arg Glu Tyr Gly Ser Cys Ser His His Tyr Gln Gln
                1090                1095                1100

Leu Leu Gln Ser Leu Glu Gln Gly Ala Gln Glu Glu Ser Arg Cys Gln
1105                1110                1115                1120

Arg Cys Ile Ser Glu Leu Lys Asp Ile Arg Leu Gln Leu Glu Ala Cys
                1125                1130                1135

Glu Thr Arg Thr Val His Arg Leu Arg Leu Pro Leu Asp Lys Glu Pro
                1140                1145                1150

Ala Arg Glu Cys Ala Gln Arg Ile Ala Glu Gln Gln Lys Ala Gln Ala
                1155                1160                1165

Glu Val Glu Gly Leu Gly Lys Gly Val Ala Arg Leu Ser Ala Glu Ala
                1170                1175                1180

Glu Lys Val Leu Ala Leu Pro Glu Pro Ser Pro Ala Ala Pro Thr Leu
1185                1190                1195                1200

Arg Ser Glu Leu Glu Leu Thr Leu Gly Lys Leu Glu Gln Val Arg Ser
                1205                1210                1215

Leu Ser Ala Ile Tyr Leu Glu Lys Leu Lys Thr Ile Ser Leu Val Ile
                1220                1225                1230

Arg Gly Thr Gln Gly Ala Glu Glu Val Leu Arg Ala His Glu Glu Gln
                1235                1240                1245

Leu Lys Glu Ala Gln Ala Val Pro Ala Thr Leu Pro Glu Leu Glu Ala
                1250                1255                1260

Thr Lys Ala Ser Leu Lys Lys Leu Arg Ala Gln Ala Glu Ala Gln Gln
1265                1270                1275                1280

Pro Thr Phe Asp Ala Leu Arg Asp Glu Leu Arg Gly Ala Gln Glu Val
                1285                1290                1295

Gly Glu Arg Leu Gln Gln Arg His Gly Glu Arg Asp Val Glu Val Glu
                1300                1305                1310

Arg Trp Arg Glu Arg Val Ala Gln Leu Leu Glu Arg Trp Gln Ala Val
                1315                1320                1325

Leu Ala Gln Thr Asp Val Arg Gln Arg Glu Leu Glu Gln Leu Gly Arg
                1330                1335                1340

Gln Leu Arg Tyr Tyr Arg Glu Ser Ala Asp Pro Leu Gly Ala Trp Leu
1345                1350                1355                1360
```

```
Gln Asp Ala Arg Arg Arg Gln Glu Gln Ile Gln Ala Met Pro Leu Ala
            1365                1370                1375

Asp Ser Gln Ala Val Arg Glu Gln Leu Arg Gln Glu Gln Ala Leu Leu
        1380                1385                1390

Glu Glu Ile Glu Arg His Gly Glu Lys Val Glu Cys Gln Arg Phe
    1395                1400                1405

Ala Lys Gln Tyr Ile Asn Ala Ile Lys Asp Tyr Glu Leu Gln Leu Val
    1410                1415                1420

Thr Tyr Lys Ala Gln Leu Glu Pro Val Ala Ser Pro Ala Lys Lys Pro
1425                1430                1435                1440

Lys Val Gln Ser Gly Ser Glu Ser Val Ile Gln Glu Tyr Val Asp Leu
        1445                1450                1455

Arg Thr His Tyr Ser Glu Leu Thr Thr Leu Thr Ser Gln Tyr Ile Lys
        1460                1465                1470

Phe Ile Ser Glu Thr Leu Arg Arg Met Glu Glu Glu Arg Leu Ala
    1475                1480                1485

Glu Gln Gln Arg Ala Glu Glu Arg Glu Arg Leu Ala Glu Val Glu Ala
    1490                1495                1500

Ala Leu Glu Lys Gln Arg Gln Leu Ala Glu Ala His Ala Gln Ala Lys
1505                1510                1515                1520

Ala Gln Ala Glu Arg Glu Ala Lys Glu Leu Gln Gln Arg Met Gln Glu
        1525                1530                1535

Glu Val Val Arg Arg Glu Glu Ala Ala Val Asp Ala Gln Gln Gln Lys
        1540                1545                1550

Arg Ser Ile Gln Glu Glu Leu Gln Gln Leu Arg Gln Ser Ser Glu Ala
        1555                1560                1565

Glu Ile Gln Ala Lys Ala Arg Gln Ala Glu Ala Ala Glu Arg Ser Arg
    1570                1575                1580

Leu Arg Ile Glu Glu Glu Ile Arg Val Val Arg Leu Gln Leu Glu Ala
1585                1590                1595                1600

Thr Glu Arg Gln Arg Gly Gly Ala Glu Gly Glu Leu Gln Ala Leu Arg
        1605                1610                1615

Ala Arg Ala Glu Glu Ala Glu Ala Gln Lys Arg Gln Ala Gln Glu Glu
    1620                1625                1630

Ala Glu Arg Leu Arg Arg Gln Val Gln Asp Glu Ser Gln Arg Lys Arg
    1635                1640                1645

Gln Ala Glu Val Glu Leu Ala Ser Arg Val Lys Ala Glu Ala Glu Ala
    1650                1655                1660

Ala Arg Glu Lys Gln Arg Ala Leu Gln Ala Leu Glu Glu Leu Arg Leu
1665                1670                1675                1680

Gln Ala Glu Glu Ala Glu Arg Arg Leu Arg Gln Ala Glu Val Glu Arg
        1685                1690                1695

Ala Arg Gln Val Gln Val Ala Leu Glu Thr Ala Gln Arg Ser Ala Glu
    1700                1705                1710

Ala Glu Leu Gln Ser Lys Arg Ala Ser Phe Ala Glu Lys Thr Ala Gln
        1715                1720                1725

Leu Glu Arg Ser Leu Gln Glu Glu His Val Ala Val Ala Gln Leu Arg
        1730                1735                1740

Glu Glu Ala Glu Arg Arg Ala Gln Gln Ala Glu Ala Glu Arg Ala
1745                1750                1755                1760

Arg Glu Glu Ala Glu Arg Glu Leu Glu Arg Trp Gln Leu Lys Ala Asn
        1765                1770                1775
```

-continued

Glu Ala Leu Arg Leu Arg Leu Gln Ala Glu Val Ala Gln Gln Lys
        1780                1785                1790

Ser Leu Ala Gln Ala Glu Ala Glu Lys Gln Lys Glu Glu Ala Glu Arg
    1795                1800                1805

Glu Ala Arg Arg Arg Gly Lys Ala Glu Glu Gln Ala Val Arg Gln Arg
        1810                1815                1820

Glu Leu Ala Glu Gln Glu Leu Glu Lys Gln Arg Gln Leu Ala Glu Gly
1825                1830                1835                1840

Thr Ala Gln Gln Arg Leu Ala Ala Glu Gln Leu Ile Arg Leu Arg
            1845                1850                1855

Ala Glu Thr Glu Gln Gly Glu Gln Gln Arg Gln Leu Leu Glu Glu Glu
        1860                1865                1870

Leu Ala Arg Leu Gln Arg Glu Ala Ala Ala Thr Gln Lys Arg Gln
        1875                1880                1885

Glu Leu Glu Ala Glu Leu Ala Lys Val Arg Ala Glu Met Glu Val Leu
        1890                1895                1900

Leu Ala Ser Lys Ala Arg Ala Glu Glu Glu Ser Arg Ser Thr Ser Glu
1905                1910                1915                1920

Lys Ser Lys Gln Arg Leu Glu Ala Glu Ala Gly Arg Phe Arg Glu Leu
        1925                1930                1935

Ala Glu Glu Ala Ala Arg Leu Arg Ala Leu Ala Glu Glu Ala Lys Arg
        1940                1945                1950

Gln Arg Gln Leu Ala Glu Glu Asp Ala Ala Arg Gln Arg Ala Glu Ala
        1955                1960                1965

Glu Arg Val Leu Ala Glu Lys Leu Ala Ala Ile Gly Glu Ala Thr Arg
        1970                1975                1980

Leu Lys Thr Glu Ala Glu Ile Ala Leu Lys Glu Lys Glu Ala Glu Asn
1985                1990                1995                2000

Glu Arg Leu Arg Arg Leu Ala Glu Asp Glu Ala Phe Gln Arg Arg
        2005                2010                2015

Leu Glu Glu Gln Ala Ala Gln His Lys Ala Asp Ile Glu Glu Arg Leu
        2020                2025                2030

Ala Gln Leu Arg Lys Ala Ser Asp Ser Glu Leu Glu Arg Gln Lys Gly
        2035                2040                2045

Leu Val Glu Asp Thr Leu Arg Gln Arg Arg Gln Val Glu Glu Glu Ile
        2050                2055                2060

Leu Ala Leu Lys Ala Ser Phe Glu Lys Ala Ala Ala Gly Lys Ala Glu
2065                2070                2075                2080

Leu Glu Leu Glu Leu Gly Arg Ile Arg Ser Asn Ala Glu Asp Thr Leu
        2085                2090                2095

Arg Ser Lys Glu Gln Ala Glu Leu Glu Ala Ala Arg Gln Arg Gln Leu
        2100                2105                2110

Ala Ala Glu Glu Glu Arg Arg Arg Arg Glu Ala Glu Glu Arg Val Gln
        2115                2120                2125

Lys Ser Leu Ala Ala Glu Glu Ala Ala Arg Gln Arg Lys Ala Ala
        2130                2135                2140

Leu Glu Glu Val Glu Arg Leu Lys Ala Lys Val Glu Glu Ala Arg Arg
2145                2150                2155                2160

Leu Arg Glu Arg Ala Glu Gln Glu Ser Ala Arg Gln Leu Gln Leu Ala
            2165                2170                2175

Gln Glu Ala Ala Gln Lys Arg Leu Gln Ala Glu Glu Lys Ala His Ala
        2180                2185                2190

Phe Ala Val Gln Gln Lys Glu Gln Glu Leu Gln Gln Thr Leu Gln Gln

-continued

```
              2195                2200                2205
Glu Gln Ser Val Leu Asp Gln Leu Arg Gly Glu Ala Glu Ala Arg
              2210                2215                2220
Arg Ala Ala Glu Glu Ala Glu Ala Arg Val Gln Ala Glu Arg Glu
2225                2230                2235                2240
Ala Ala Gln Ser Arg Gln Val Glu Ala Glu Arg Leu Lys Gln
              2245                2250                2255
Ser Ala Glu Glu Gln Ala Gln Ala Arg Ala Gln Ala Gln Ala Ala
              2260                2265                2270
Glu Lys Leu Arg Lys Glu Ala Glu Gln Glu Ala Ala Arg Arg Ala Gln
              2275                2280                2285
Ala Glu Gln Ala Ala Leu Arg Gln Lys Gln Ala Ala Asp Ala Glu Met
              2290                2295                2300
Glu Lys His Lys Lys Phe Ala Glu Gln Thr Leu Arg Gln Lys Ala Gln
              2305                2310                2315                2320
Val Glu Gln Glu Leu Thr Thr Leu Arg Leu Gln Leu Glu Glu Thr Asp
                        2325                2330                2335
His Gln Lys Asn Leu Leu Asp Glu Glu Leu Gln Arg Leu Lys Ala Glu
                        2340                2345                2350
Ala Thr Glu Ala Ala Arg Gln Arg Ser Gln Val Glu Glu Glu Leu Phe
              2355                2360                2365
Ser Val Arg Val Gln Met Glu Glu Leu Ser Lys Leu Lys Ala Arg Ile
              2370                2375                2380
Glu Ala Glu Asn Arg Ala Leu Ile Leu Arg Asp Lys Asp Asn Thr Gln
2385                2390                2395                2400
Arg Phe Leu Gln Glu Glu Ala Glu Lys Met Lys Gln Val Ala Glu Glu
              2405                2410                2415
Ala Ala Arg Leu Ser Val Ala Ala Gln Glu Ala Ala Arg Leu Arg Gln
              2420                2425                2430
Leu Ala Glu Glu Asp Leu Ala Gln Gln Arg Ala Leu Ala Glu Lys Met
              2435                2440                2445
Leu Lys Glu Lys Met Gln Ala Val Gln Glu Ala Thr Arg Leu Lys Ala
              2450                2455                2460
Glu Ala Glu Leu Leu Gln Gln Gln Lys Glu Leu Ala Gln Glu Gln Ala
2465                2470                2475                2480
Arg Arg Leu Gln Glu Asp Lys Glu Gln Met Ala Gln Gln Leu Ala Glu
              2485                2490                2495
Glu Thr Gln Gly Phe Gln Arg Thr Leu Glu Ala Glu Arg Gln Arg Gln
              2500                2505                2510
Leu Glu Met Ser Ala Glu Ala Glu Arg Leu Lys Leu Arg Val Ala Glu
              2515                2520                2525
Met Ser Arg Ala Gln Ala Arg Ala Glu Glu Asp Ala Gln Arg Phe Arg
              2530                2535                2540
Lys Gln Ala Glu Glu Ile Gly Glu Lys Leu His Arg Thr Glu Leu Ala
2545                2550                2555                2560
Thr Gln Glu Lys Val Thr Leu Val Gln Thr Leu Glu Ile Gln Arg Gln
              2565                2570                2575
Gln Ser Asp His Asp Ala Glu Arg Leu Arg Glu Ala Ile Ala Glu Leu
              2580                2585                2590
Glu Arg Glu Lys Glu Lys Leu Gln Gln Glu Ala Lys Leu Leu Gln Leu
              2595                2600                2605
Lys Ser Glu Glu Met Gln Thr Val Gln Gln Glu Gln Leu Leu Gln Glu
              2610                2615                2620
```

```
Thr Gln Ala Leu Gln Gln Ser Phe Leu Ser Glu Lys Asp Ser Leu Leu
2625                2630                2635                2640

Gln Arg Glu Arg Phe Ile Glu Gln Glu Lys Ala Lys Leu Glu Gln Leu
            2645                2650                2655

Phe Gln Asp Glu Val Ala Lys Ala Gln Gln Leu Arg Glu Glu Gln Gln
        2660                2665                2670

Arg Gln Gln Gln Gln Met Glu Gln Glu Arg Gln Arg Leu Val Ala Ser
        2675                2680                2685

Met Glu Glu Ala Arg Arg Gln His Glu Ala Glu Glu Gly Val Arg
2690                2695                2700

Arg Lys Gln Glu Glu Leu Gln Gln Leu Glu Gln Arg Arg Gln Gln
2705                2710                2715                2720

Glu Glu Leu Leu Ala Glu Glu Asn Gln Arg Leu Arg Glu Gln Leu Gln
                2725                2730                2735

Leu Leu Glu Glu Gln His Arg Ala Ala Leu Ala His Ser Glu Glu Val
            2740                2745                2750

Thr Ala Ser Gln Val Ala Ala Thr Lys Thr Leu Pro Asn Gly Arg Asp
        2755                2760                2765

Ala Leu Asp Gly Pro Ala Ala Glu Ala Glu Pro Glu His Ser Phe Asp
2770                2775                2780

Gly Leu Arg Arg Lys Val Ser Ala Gln Arg Leu Gln Glu Ala Gly Ile
2785                2790                2795                2800

Leu Ser Ala Glu Glu Leu Gln Arg Leu Ala Gln Gly His Thr Thr Val
            2805                2810                2815

Asp Glu Leu Ala Arg Arg Glu Asp Val Arg His Tyr Leu Gln Gly Arg
        2820                2825                2830

Ser Ser Ile Ala Gly Leu Leu Leu Lys Ala Thr Asn Glu Lys Leu Ser
        2835                2840                2845

Val Tyr Ala Ala Leu Gln Arg Gln Leu Leu Ser Pro Gly Thr Ala Leu
    2850                2855                2860

Ile Leu Leu Glu Ala Gln Ala Ala Ser Gly Phe Leu Leu Asp Pro Val
2865                2870                2875                2880

Arg Asn Arg Arg Leu Thr Val Asn Glu Ala Val Lys Glu Gly Val Val
            2885                2890                2895

Gly Pro Glu Leu His His Lys Leu Leu Ser Ala Glu Arg Ala Val Thr
        2900                2905                2910

Gly Tyr Lys Asp Pro Tyr Thr Gly Gln Gln Ile Ser Leu Phe Gln Ala
        2915                2920                2925

Met Gln Lys Gly Leu Ile Val Arg Glu His Gly Ile Arg Leu Leu Glu
    2930                2935                2940

Ala Gln Ile Ala Thr Gly Gly Val Ile Asp Pro Val His Ser His Arg
2945                2950                2955                2960

Val Pro Val Asp Val Ala Tyr Arg Arg Gly Tyr Phe Asp Glu Glu Met
            2965                2970                2975

Asn Arg Val Leu Ala Asp Pro Ser Asp Asp Thr Lys Gly Phe Phe Asp
        2980                2985                2990

Pro Asn Thr His Glu Asn Leu Thr Tyr Leu Gln Leu Leu Glu Arg Cys
        2995                3000                3005

Val Glu Asp Pro Glu Thr Gly Leu Cys Leu Leu Pro Leu Thr Asp Lys
    3010                3015                3020

Ala Ala Lys Gly Gly Glu Leu Val Tyr Thr Asp Ser Glu Ala Arg Asp
3025                3030                3035                3040
```

-continued

```
Val Phe Glu Lys Ala Thr Val Ser Ala Pro Phe Gly Lys Phe Gln Gly
                3045                3050                3055
Lys Thr Val Thr Ile Trp Glu Ile Ile Asn Ser Glu Tyr Phe Thr Ala
            3060                3065                3070
Glu Gln Arg Arg Asp Leu Leu Arg Gln Phe Arg Thr Gly Arg Ile Thr
        3075                3080                3085
Val Glu Lys Ile Ile Lys Ile Ile Ile Thr Val Val Glu Glu Gln Glu
    3090                3095                3100
Gln Lys Gly Arg Leu Cys Phe Glu Gly Leu Arg Ser Leu Val Pro Ala
3105                3110                3115                3120
Ala Glu Leu Leu Glu Ser Arg Val Ile Asp Arg Glu Leu Tyr Gln Gln
                3125                3130                3135
Leu Gln Arg Gly Glu Arg Ser Val Arg Asp Val Ala Glu Val Asp Thr
            3140                3145                3150
Val Arg Arg Ala Leu Arg Gly Ala Asn Val Ile Ala Gly Val Trp Leu
        3155                3160                3165
Glu Glu Ala Gly Gln Lys Leu Ser Ile Tyr Asn Ala Leu Lys Lys Asp
    3170                3175                3180
Leu Leu Pro Ser Asp Met Ala Val Ala Leu Leu Glu Ala Gln Ala Gly
3185                3190                3195                3200
Thr Gly His Ile Ile Asp Pro Ala Thr Ser Ala Arg Leu Thr Val Asp
                3205                3210                3215
Glu Ala Val Arg Ala Gly Leu Val Gly Pro Glu Phe His Glu Lys Leu
            3220                3225                3230
Leu Ser Ala Glu Lys Ala Val Thr Gly Tyr Arg Asp Pro Tyr Thr Gly
        3235                3240                3245
Gln Ser Val Ser Leu Phe Gln Ala Leu Lys Lys Gly Leu Ile Pro Arg
    3250                3255                3260
Glu Gln Gly Leu Arg Leu Leu Asp Ala Gln Leu Ser Thr Gly Gly Ile
3265                3270                3275                3280
Val Asp Pro Ser Lys Ser His Arg Val Pro Leu Asp Val Ala Cys Ala
                3285                3290                3295
Arg Gly Cys Leu Asp Glu Glu Thr Ser Arg Ala Leu Ser Ala Pro Arg
            3300                3305                3310
Ala Asp Ala Lys Ala Tyr Ser Asp Pro Ser Thr Gly Glu Pro Ala Thr
        3315                3320                3325
Tyr Gly Glu Leu Gln Gln Arg Cys Arg Pro Asp Gln Leu Thr Gly Leu
    3330                3335                3340
Ser Leu Leu Pro Leu Ser Glu Lys Ala Ala Arg Ala Arg Gln Glu Glu
3345                3350                3355                3360
Leu Tyr Ser Glu Leu Gln Ala Arg Glu Thr Phe Glu Lys Thr Pro Val
                3365                3370                3375
Glu Val Pro Val Gly Gly Phe Lys Gly Arg Thr Val Thr Val Trp Glu
            3380                3385                3390
Leu Ile Ser Ser Glu Tyr Phe Thr Ala Glu Gln Arg Gln Glu Leu Leu
        3395                3400                3405
Arg Gln Phe Arg Thr Gly Lys Val Thr Val Glu Lys Val Ile Lys Ile
    3410                3415                3420
Leu Ile Thr Ile Val Glu Val Glu Thr Leu Arg Gln Glu Arg Leu
3425                3430                3435                3440
Ser Phe Ser Gly Leu Arg Ala Pro Val Pro Ala Ser Glu Leu Leu Ala
                3445                3450                3455
Ser Gly Val Leu Ser Arg Ala Gln Phe Glu Gln Leu Lys Asp Gly Lys
```

-continued

```
                3460            3465            3470
Thr Thr Val Lys Asp Leu Ser Glu Leu Gly Ser Val Arg Thr Leu Leu
        3475            3480            3485
Gln Gly Ser Gly Cys Leu Ala Gly Ile Tyr Leu Glu Asp Thr Lys Glu
        3490            3495            3500
Lys Val Ser Ile Tyr Glu Ala Met Arg Arg Gly Leu Leu Arg Ala Thr
3505            3510            3515            3520
Thr Ala Ala Leu Leu Leu Glu Ala Gln Ala Ala Thr Gly Phe Leu Val
        3525            3530            3535
Asp Pro Val Arg Asn Gln Arg Leu Tyr Val His Glu Ala Val Lys Ala
        3540            3545            3550
Gly Val Val Gly Pro Glu Leu His Glu Gln Leu Leu Ser Ala Glu Lys
        3555            3560            3565
Ala Val Thr Gly Tyr Arg Asp Pro Tyr Ser Gly Ser Thr Ile Ser Leu
        3570            3575            3580
Phe Gln Ala Met Gln Lys Gly Leu Val Leu Arg Gln His Gly Ile Arg
3585            3590            3595            3600
Leu Leu Glu Ala Gln Ile Ala Thr Gly Gly Ile Ile Asp Pro Val His
        3605            3610            3615
Ser His Arg Val Pro Val Asp Val Ala Tyr Gln Arg Gly Tyr Phe Ser
        3620            3625            3630
Glu Glu Met Asn Arg Val Leu Ala Asp Pro Ser Asp Asp Thr Lys Gly
        3635            3640            3645
Phe Phe Asp Pro Asn Thr His Glu Asn Leu Thr Tyr Arg Gln Leu Leu
        3650            3655            3660
Glu Arg Cys Val Glu Asp Pro Glu Thr Gly Leu Arg Leu Leu Pro Leu
3665            3670            3675            3680
Lys Gly Ala Glu Lys Ala Glu Val Val Glu Thr Thr Gln Val Tyr Thr
        3685            3690            3695
Glu Glu Glu Thr Arg Arg Ala Phe Glu Glu Thr Gln Ile Asp Ile Pro
        3700            3705            3710
Gly Gly Gly Ser His Gly Gly Ser Thr Met Ser Leu Trp Glu Val Met
        3715            3720            3725
Gln Ser Asp Leu Ile Pro Glu Glu Gln Arg Ala Gln Leu Met Ala Asp
        3730            3735            3740
Phe Gln Ala Gly Arg Val Thr Lys Glu Arg Met Ile Ile Ile Ile
3745            3750            3755            3760
Glu Ile Ile Glu Lys Thr Glu Ile Ile Arg Gln Gln Gly Leu Ala Ser
        3765            3770            3775
Tyr Asp Tyr Val Arg Arg Arg Leu Thr Ala Glu Asp Leu Phe Glu Ala
        3780            3785            3790
Arg Ile Ile Ser Leu Glu Thr Tyr Asn Leu Leu Arg Glu Gly Thr Arg
        3795            3800            3805
Ser Leu Arg Glu Ala Leu Glu Ala Glu Ser Ala Trp Cys Tyr Leu Tyr
        3810            3815            3820
Gly Thr Gly Ser Val Ala Gly Val Tyr Leu Pro Gly Ser Arg Gln Thr
3825            3830            3835            3840
Leu Ser Ile Tyr Gln Ala Leu Lys Lys Gly Leu Leu Ser Ala Glu Val
        3845            3850            3855
Ala Arg Leu Leu Leu Glu Ala Gln Ala Ala Thr Gly Phe Leu Leu Asp
        3860            3865            3870
Pro Val Lys Gly Glu Arg Leu Thr Val Asp Glu Ala Val Arg Lys Gly
        3875            3880            3885
```

```
Leu Val Gly Pro Glu Leu His Asp Arg Leu Leu Ser Ala Glu Arg Ala
    3890                3895                3900

Val Thr Gly Tyr Arg Asp Pro Tyr Thr Glu Gln Thr Ile Ser Leu Phe
3905                3910                3915                3920

Gln Ala Met Lys Lys Glu Leu Ile Pro Thr Glu Glu Ala Leu Arg Leu
            3925                3930                3935

Leu Asp Ala Gln Leu Ala Thr Gly Gly Ile Val Asp Pro Arg Leu Gly
            3940                3945                3950

Phe His Leu Pro Leu Glu Val Ala Tyr Gln Arg Gly Tyr Leu Asn Lys
        3955                3960                3965

Asp Thr His Asp Gln Leu Ser Glu Pro Ser Glu Val Arg Ser Tyr Val
    3970                3975                3980

Asp Pro Ser Thr Asp Glu Arg Leu Ser Tyr Thr Gln Leu Leu Arg Arg
3985                3990                3995                4000

Cys Arg Arg Asp Asp Gly Thr Gly Gln Leu Leu Leu Pro Leu Ser Asp
                4005                4010                4015

Ala Arg Lys Leu Thr Phe Arg Gly Leu Arg Lys Gln Ile Thr Met Glu
            4020                4025                4030

Glu Leu Val Arg Ser Gln Val Met Asp Glu Ala Thr Ala Leu Gln Leu
            4035                4040                4045

Arg Glu Gly Leu Thr Ser Ile Glu Glu Val Thr Lys Asn Leu Gln Lys
        4050                4055                4060

Phe Leu Glu Gly Thr Ser Cys Ile Ala Gly Val Phe Val Asp Ala Thr
4065                4070                4075                4080

Lys Glu Arg Leu Ser Val Tyr Gln Ala Met Lys Lys Gly Ile Ile Arg
            4085                4090                4095

Pro Gly Thr Ala Phe Glu Leu Leu Glu Ala Gln Ala Ala Thr Gly Tyr
            4100                4105                4110

Val Ile Asp Pro Ile Lys Gly Leu Lys Leu Thr Val Glu Glu Ala Val
            4115                4120                4125

Arg Met Gly Ile Val Gly Pro Glu Phe Lys Asp Lys Leu Leu Ser Ala
    4130                4135                4140

Glu Arg Ala Val Thr Gly Tyr Lys Asp Pro Tyr Ser Gly Lys Leu Ile
4145                4150                4155                4160

Ser Leu Phe Gln Ala Met Lys Lys Gly Leu Ile Leu Lys Asp His Gly
            4165                4170                4175

Ile Arg Leu Leu Glu Ala Gln Ile Ala Thr Gly Gly Ile Ile Asp Pro
            4180                4185                4190

Glu Glu Ser His Arg Leu Pro Val Glu Val Ala Tyr Lys Arg Gly Leu
        4195                4200                4205

Phe Asp Glu Glu Met Asn Glu Ile Leu Thr Asp Pro Ser Asp Asp Thr
    4210                4215                4220

Lys Gly Phe Phe Asp Pro Asn Thr Glu Glu Asn Leu Thr Tyr Leu Gln
4225                4230                4235                4240

Leu Met Glu Arg Cys Ile Thr Asp Pro Gln Thr Gly Leu Cys Leu Leu
            4245                4250                4255

Pro Leu Lys Glu Lys Lys Arg Glu Arg Lys Thr Ser Ser Lys Ser Ser
            4260                4265                4270

Val Arg Lys Arg Arg Val Val Ile Val Asp Pro Glu Thr Gly Lys Glu
        4275                4280                4285

Met Ser Val Tyr Glu Ala Tyr Arg Lys Gly Leu Ile Asp His Gln Thr
    4290                4295                4300
```

Tyr Leu Glu Leu Ser Glu Gln Glu Cys Glu Trp Glu Glu Ile Thr Ile
4305                4310                4315                4320

Ser Ser Ser Asp Gly Val Val Lys Ser Met Ile Ile Asp Arg Arg Ser
            4325                4330                4335

Gly Arg Gln Tyr Asp Ile Asp Asp Ala Ile Ala Lys Asn Leu Ile Asp
        4340                4345                4350

Arg Ser Ala Leu Asp Gln Tyr Arg Ala Gly Thr Leu Ser Ile Thr Glu
    4355                4360                4365

Phe Ala Asp Met Leu Ser Gly Asn Ala Gly Gly Phe Arg Ser Arg Ser
4370                4375                4380

Ser Ser Val Gly Ser Ser Ser Tyr Pro Ile Ser Pro Ala Val Ser
4385                4390                4395                4400

Arg Thr Gln Leu Ala Ser Trp Ser Asp Pro Thr Glu Glu Thr Gly Pro
        4405                4410                4415

Val Ala Gly Ile Leu Asp Thr Glu Thr Leu Glu Lys Val Ser Ile Thr
            4420                4425                4430

Glu Ala Met His Arg Asn Leu Val Asp Asn Ile Thr Gly Gln Arg Leu
    4435                4440                4445

Leu Glu Ala Gln Ala Cys Thr Gly Gly Ile Ile Asp Pro Ser Thr Gly
4450                4455                4460

Glu Arg Phe Pro Val Thr Asp Ala Val Asn Lys Gly Leu Val Asp Lys
4465                4470                4475                4480

Ile Met Val Asp Arg Ile Asn Leu Ala Gln Lys Ala Phe Cys Gly Phe
            4485                4490                4495

Glu Asp Pro Arg Thr Lys Thr Lys Met Ser Ala Ala Gln Ala Leu Lys
        4500                4505                4510

Lys Gly Trp Leu Tyr Tyr Glu Ala Gly Gln Arg Phe Leu Glu Val Gln
    4515                4520                4525

Tyr Leu Thr Gly Gly Leu Ile Glu Pro Asp Thr Pro Gly Arg Val Pro
4530                4535                4540

Leu Asp Glu Ala Leu Gln Arg Gly Thr Val Asp Ala Arg Thr Ala Gln
4545                4550                4555                4560

Lys Leu Arg Asp Val Gly Ala Tyr Ser Lys Tyr Leu Thr Cys Pro Lys
            4565                4570                4575

Thr Lys Leu Lys Ile Ser Tyr Lys Asp Ala Leu Asp Arg Ser Met Val
        4580                4585                4590

Glu Glu Gly Thr Gly Leu Arg Leu Leu Glu Ala Ala Ala Gln Ser Thr
    4595                4600                4605

Lys Gly Tyr Tyr Ser Pro Tyr Ser Val Ser Gly Ser Gly Ser Thr Ala
4610                4615                4620

Gly Ser Arg Thr Gly Ser Arg Thr Gly Ser Arg Ala Gly Ser Arg Arg
4625                4630                4635                4640

Gly Ser Phe Asp Ala Thr Gly Ser Gly Phe Ser Met Thr Phe Ser Ser
            4645                4650                4655

Ser Ser Tyr Ser Ser Ser Gly Tyr Gly Arg Arg Tyr Ala Ser Gly Ser
        4660                4665                4670

Ser Ala Ser Leu Gly Gly Pro Glu Ser Ala Val Ala
    4675                4680

<210> SEQ ID NO 25
<211> LENGTH: 36
<212> TYPE: PRT
<213> ORGANISM: Artificial Sequence
<220> FEATURE:
<223> OTHER INFORMATION: Synthetic peptide

```
<400> SEQUENCE: 25

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

<400> SEQUENCE: 26

Thr Ser His His His His His His Cys
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic peptide

<400> SEQUENCE: 27

Gly Gly Ser Lys Cys
1               5
```